US006991594B2

(12) United States Patent
Holcomb

(10) Patent No.: US 6,991,594 B2
(45) Date of Patent: *Jan. 31, 2006

(54) METHOD AND APPARATUS FOR ALTERING THE CHARGE DISTRIBUTION UPON LIVING MEMBRANES WITH FUNCTIONAL STABILIZATION OF THE MEMBRANE PHYSICAL ELECTRICAL INTEGRITY

(75) Inventor: Robert R. Holcomb, Nashville, TN (US)

(73) Assignee: Holcomb Healthcare Services, LLC, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/265,921

(22) Filed: Oct. 7, 2002

(65) Prior Publication Data

US 2003/0092960 A1 May 15, 2003

Related U.S. Application Data

(63) Continuation of application No. 09/484,801, filed on Jan. 18, 2000, now Pat. No. 6,461,288, which is a continuation-in-part of application No. 08/926,633, filed on Sep. 10, 1997, now abandoned.
(60) Provisional application No. 60/025,176, filed on Sep. 10, 1996, now abandoned.

(51) Int. Cl.
  *A61N 2/00* (2006.01)
  *A61B 19/00* (2006.01)

(52) U.S. Cl. .......................................... 600/9; 128/897
(58) Field of Classification Search ............... 600/9–15; 607/3; 128/897
See application file for complete search history.

(56) References Cited

U.S. PATENT DOCUMENTS

| 5,312,321 | A | 5/1994 | Holcomb |
| 5,707,333 | A | 1/1998 | Bakst |
| 5,738,624 | A | 4/1998 | Zablotsky et al. |
| 5,782,743 | A | 7/1998 | Russell |
| 5,941,902 | A | 8/1999 | Holcomb |
| 6,245,006 | B1 | 6/2001 | Olson |
| 6,461,288 | B1 | 10/2002 | Holcomb |

FOREIGN PATENT DOCUMENTS

WO 99/12605 3/1999

*Primary Examiner*—Samuel G. Gilbert
*Assistant Examiner*—Nikita R. Veniaminov
(74) *Attorney, Agent, or Firm*—Garvey, Smith, Nehrbass & Doody, L.L.C.; Gregory C. Smith

(57) ABSTRACT

A method and apparatus for altering the charge distribution upon living membranes with functional stabilizational of the membrane physical electrical integrity further comprising a method for using submicroscopic, quadripolar, circular, center charged, energy balanced magnetic device in a four (4) magnet array of alternating polarity in which the magnetic poles are separated only by a distance which will allow a magnetic sphere of influence on all adjacent poles to suppress the firing of action potentials of mammalian sensory neurons. The method and apparatus further provides a static magnetic device for production of a magnetic field for treatment of various disorders. Further there is provided a static magnetic device for production of a magnetic field for treatment of disorders wherein the device provides a static magnetic pole of like polarity on the outer surface of the flux focusing ring adjacent to each of the 4 poles of the invention (focusing magnet) such that the end r top of the focusing magnet is oriented to the geometric side of the pole such that the asix of the two magnets form a 45 to 90 degree angle.

10 Claims, 71 Drawing Sheets

FIG. 1
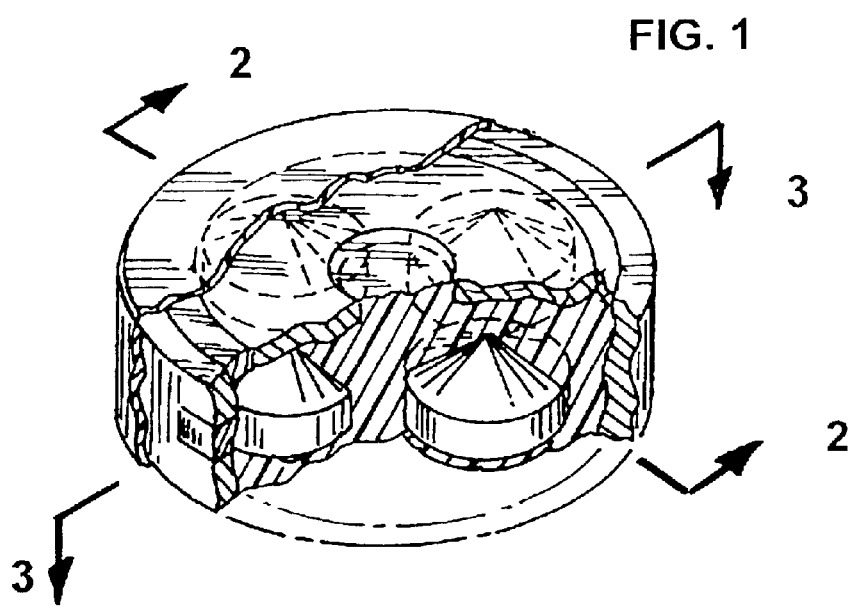
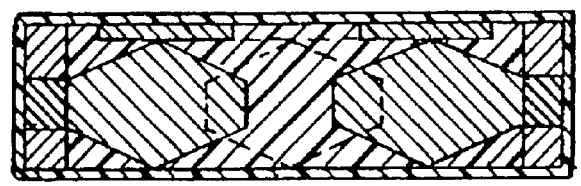
FIG. 2
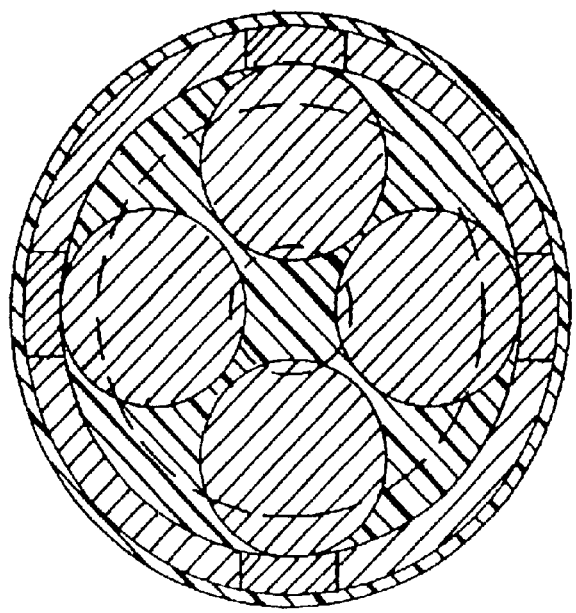
FIG. 3

The device should be placed on the skin with the smooth side facing the skin and the orientation marker pointing upward and parallel with the body or extremity. The device is held in place with a double adhesive device and may be reinforced with a non-allergenic tape.

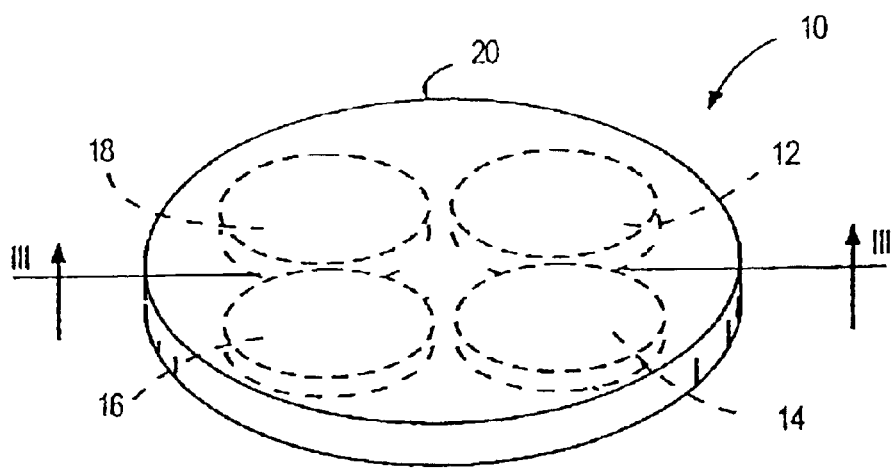
FIG. 23
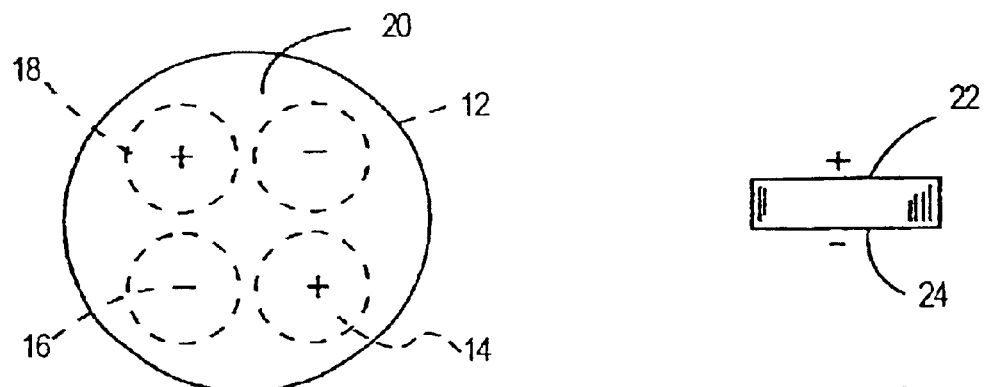
FIG. 25
FIG. 26
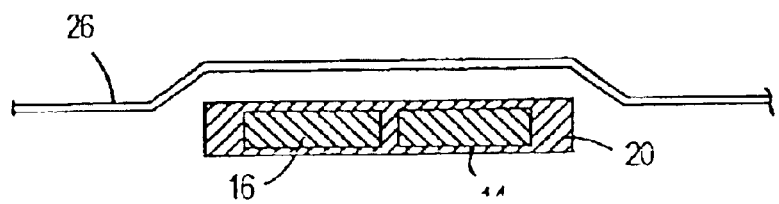
FIG. 24

| 0 | 0 | 0 | 0 | 0 | 0 | 0 | 0 | 0 | 0 | 0 | 0 |
|---|---|---|---|---|---|---|---|---|---|---|---|
| 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 |
| 0 | 0 | 0 | -1 | -1 | -2 | +10 | +20 | +10 | +10 | 0 | 0 |
| 0 | 0 | -1 | -1 | -10 | +18 | -19 | +23 | +10 | +3 | +2 | 0 |
| 0 | 0 | -1 | -5 | +39 | N +1928 | S -1800 | -36 | +8 | +1 | 0 | 0 |
| 0 | 0 | +1 | +3 | -9 | -1988 S | +1900 N | +61 | -5 | -1 | 0 | 0 |
| 0 | +1 | +2 | +6 | +16 | -20 | -6 | -25 | -8 | -1 | 0 | 0 |
| 0 | -1 | +1 | +3 | +6 | +5 | -4 | -6 | -3 | 0 | 0 | 0 |
| 0 | 0 | 0 | +1 | +1 | 0 | -1 | -2 | -2 | -1 | 0 | 0 |
| 0 | 0 | 0 | 0 | +1 | +1 | -1 | -2 | -1 | -1 | 0 | 0 |
| 0 | 0 | 0 | 0 | 0 | 0 | 0 | 0 | 0 | 0 | 0 | 0 |

FIG. 30
(SURFACE)

| 0 | 0 | 0 | 0 | 0 | 0 | 0 | 0 | 0 | 0 | 0 | 0 |
|---|---|---|---|---|---|---|---|---|---|---|---|
| 0 | 0 | 0 | 0 | 0 | 0 | 0 | 0 | 0 | 0 | +1 | 0 |
| 0 | 0 | 0 | 0 | 0 | 0 | 0 | +1 | +2 | +1 | +1 | 0 |
| 0 | 0 | 0 | 0 | +2 | +3 | -1 | -1 | +1 | +1 | +1 | 0 |
| 0 | 0 | +1 | +2 | +12 | +33 | -33 | -18 | -1 | +1 | +1 | 0 |
| 0 | 0 | +1 | -2 | +43 | N +149 | S -118 | -82 | -2 | +1 | +1 | 0 |
| 0 | 0 | -1 | -3 | -19 | -133 S | +118 N | +98 | +4 | +1 | 0 | 0 |
| 0 | 0 | 0 | -1 | -22 | -196 | +28 | +33 | +2 | 0 | 0 | 0 |
| 0 | 0 | 0 | 0 | -2 | -8 | 0 | 0 | 0 | 0 | 0 | 0 |
| 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 |

FIG. 31
(.4 INCH ABOVE)

| 0 | 0 | 0 | 0 | 0 | 0 | 0 | 0 | 0 | 0 | 0 | 0 |
|---|---|---|---|---|---|---|---|---|---|---|---|
| 0 | 0 | 0 | 0 | 0 | 0 | 0 | 0 | 0 | 0 | 0 | 0 |
| 0 | 0 | 0 | 0 | 0 | 0 | 0 | -1 | 0 | 0 | 0 | 0 |
| 0 | 0 | 0 | +1 | +3 | +2 | -2 | -4 | -2 | 0 | 0 | 0 |
| 0 | 0 | 0 | +2 | +10 | +17 | -11 | -19 | -4 | -1 | 0 | 0 |
| 0 | 0 | 0 | +3 | +16 | N +27 | S -18 | -17 | -3 | 0 | 0 | 0 |
| 0 | 0 | 0 | -2 | -6 | S -21 | N +11 | +14 | +3 | 0 | 0 | 0 |
| 0 | 0 | -1 | -3 | -14 | -23 | +6 | +13 | +3 | 0 | 0 | 0 |
| 0 | 0 | -1 | -2 | -5 | -6 | -1 | +2 | +1 | 0 | 0 | 0 |
| 0 | 0 | 0 | 0 | -1 | -2 | 0 | 0 | 0 | -1 | 0 | -1 |
| 0 | 0 | 0 | 0 | 0 | -1 | 0 | 0 | 0 | 0 | 0 | 0 |
| 0 | 0 | 0 | 0 | 0 | 0 | 0 | 0 | 0 | 0 | 0 | 0 |

FIG. 32

(.8 INCH ABOVE)

| 0 | 0 | 0 | 0 | 0 | 0 | 0 | 0 | 0 | 0 | 0 | 0 |
|---|---|---|---|---|---|---|---|---|---|---|---|
| 0 | 0 | 0 | 0 | 0 | 0 | 0 | 0 | 0 | 0 | 0 | 0 |
| 0 | 0 | 0 | 0 | 0 | 0 | 0 | 0 | -1 | 0 | 0 | 0 |
| 0 | 0 | 0 | +1 | +2 | +1 | -2 | -2 | -2 | 0 | 0 | 0 |
| 0 | 0 | 0 | +2 | +5 | +3 | -9 | -5 | -2 | -1 | 0 | 0 |
| 0 | 0 | 0 | +2 | +5 | N +4 | S -4 | -4 | -2 | 0 | 0 | 0 |
| 0 | 0 | 0 | -1 | -3 | S -2 | +1 N | +2 | 0 | 0 | 0 | 0 |
| 0 | 0 | -1 | -3 | -6 | -6 | +2 | +4 | +1 | 0 | 0 | 0 |
| 0 | 0 | -1 | -3 | -4 | -3 | 0 | +2 | +1 | 0 | 0 | 0 |
| 0 | 0 | 0 | -1 | -2 | -2 | 0 | 0 | 0 | 0 | 0 | 0 |
| 0 | 0 | 0 | 0 | 0 | -1 | 0 | 0 | 0 | 0 | 0 | 0 |
| 0 | 0 | 0 | 0 | 0 | 0 | 0 | 0 | 0 | 0 | 0 | 0 |

FIG. 33
(1.2 INCHES ABOVE)

| 0 | 0 | 0 | 0 | 0 | 0 | 0 | 0 | 0 | 0 | 0 | 0 |
|---|---|---|---|---|---|---|---|---|---|---|---|
| 0 | 0 | 0 | 0 | 0 | 0 | 0 | 0 | 0 | 0 | 0 | 0 |
| 0 | 0 | 0 | 0 | 0 | 0 | 0 | -1 | 0 | 0 | 0 | 0 |
| 0 | 0 | 0 | 0 | +1 | +1 | 0 | -1 | -1 | 0 | 0 | 0 |
| 0 | 0 | 0 | +1 | +2 | +1 | -1 | -2 | -1 | -1 | 0 | 0 |
| 0 | 0 | 0 | 0 | +1 | N +1 | S -1 | -1 | -1 | 0 | 0 | 0 |
| 0 | 0 | 0 | 0 | -1 | S 0 | 0 N | 0 | 0 | 0 | 0 | 0 |
| 0 | 0 | -1 | -1 | -2 | -2 | 0 | +1 | 0 | 0 | 0 | 0 |
| 0 | 0 | 0 | -1 | -2 | -2 | 0 | 0 | 0 | 0 | 0 | 0 |
| 0 | 0 | 0 | 0 | -1 | -1 | 0 | 0 | 0 | 0 | 0 | 0 |
| 0 | 0 | 0 | 0 | -1 | 0 | 0 | 0 | 0 | 0 | 0 | 0 |
| 0 | 0 | 0 | 0 | 0 | 0 | 0 | 0 | 0 | 0 | 0 | 0 |

FIG. 34
(1.6 INCHES ABOVE)

| 0 | 0 | 0 | 0 | 0 | 0 | 0 | 0 | 0 | 0 | 0 | 0 |
|---|---|---|---|---|---|---|---|---|---|---|---|
| 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 |
| 0 | 0 | 0 | 0 | 0 | 0 | 0 | -1 | 0 | 0 | 0 | 0 |
| 0 | 0 | 0 | +1 | 0 | 0 | 0 | -1 | -1 | 0 | 0 | 0 |
| 0 | 0 | 0 | 0 | 0 | N 0 | S 0 | 0 | 0 | 0 | 0 | 0 |
| 0 | 0 | 0 | 0 | 0 | S -1 | N 0 | 0 | 0 | 0 | 0 | 0 |
| 0 | 0 | 0 | 0 | -1 | 0 | 0 | 0 | 0 | 0 | 0 | 0 |
| 0 | 0 | 0 | 0 | -1 | 0 | 0 | 0 | 0 | 0 | 0 | 0 |
| 0 | 0 | 0 | 0 | 0 | 0 | +1 | 0 | 0 | 0 | 0 | 0 |
| 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 |

FIG. 35
(2 INCHES ABOVE)

FIG. 36
(2.75 INCHES ABOVE)

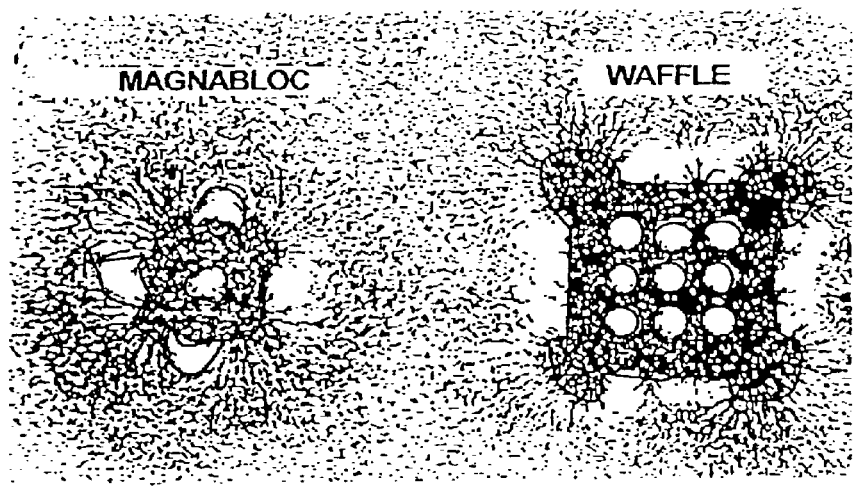
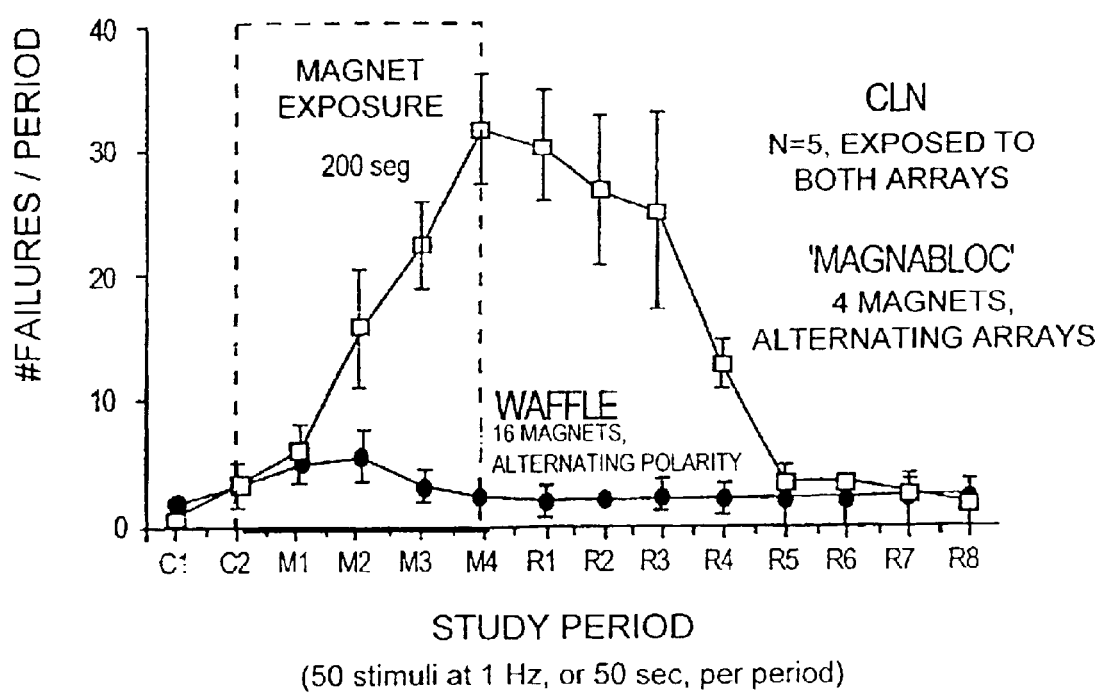
FIG. 46

| A | | A-B | | | |
|---|---|---|---|---|---|
| | | A | | B | |
| 1. 118+ | 5. 238+ | 1. (356+) | 5. (469+) | 1. (250+) | 5. (313+) |
| 2. 148- | 6. 256- | 2. (256-) | 6. (277-) | 2. (418-) | 6. (416-) |
| 3. 218+ | 7. 369+ | 3. (250+) | 7. (401+) | 3. (389+) | 7. (403+) |
| 4. 189- | 8. 330- | 4. (418-) | 8. (378-) | 4. (252-) | 8. (360-) |
| B | | | | | |
| 1. 124+ | 5. 250+ | | | | |
| 2. 130- | 6. 260- | | | | |
| 3. 180+ | 7. 240+ | | | | |
| 4. 160- | 8. 310- | | | | |

PLEASE SEE GRAPH OF LINE A-A' FOR A & B CALCULATED AS MEASURED IN PHYSICAL PROXIMITY ON AB ACTUALLY IN 'PHYSICAL CONTACT', FIGURE 4

FIG. 49
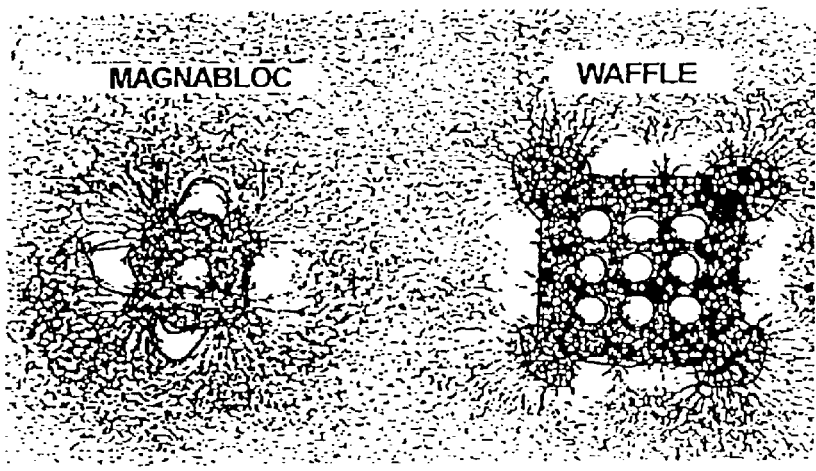
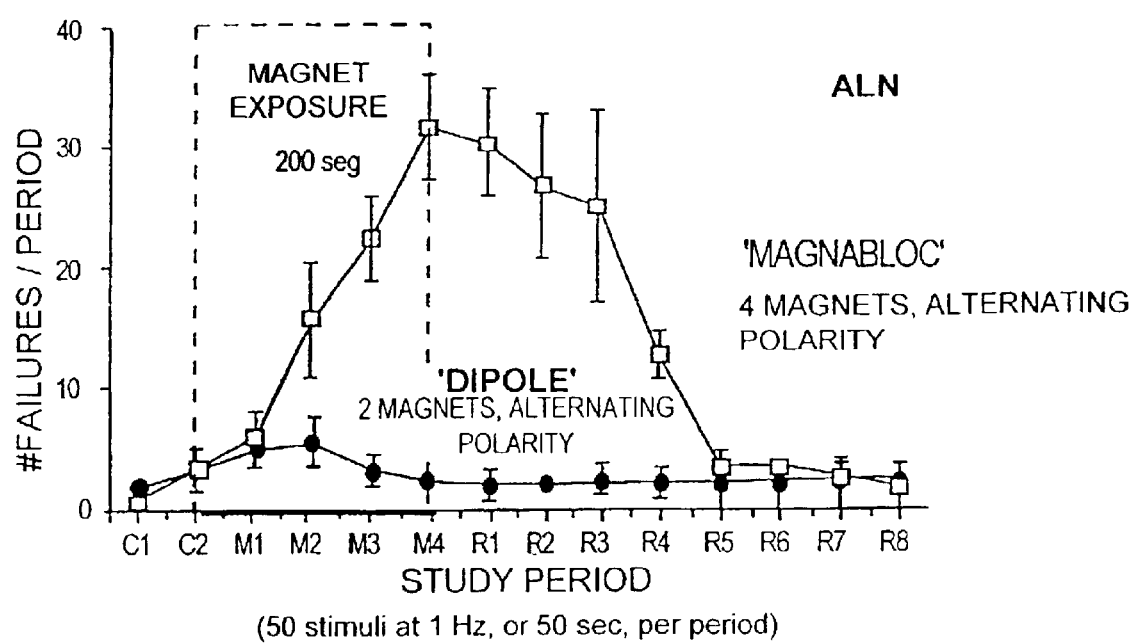
(50 stimuli at 1 Hz, or 50 sec, per period)

THIS FIGURE REPRESENTS THE PHYSICAL ARRANGEMENT OF THE GAUSS METER AND THE HALL EFFECT PROBE WHICH WAS USED TO COLLECT THE DATA OF FIGURES 20 AND 28

TRANSPORT BOX FOR PROTECTION OF CELL DEATH DURING TRANSPORT. TEMPERATURE CONTROLLED SALINE BATH UNDER CONSTANT EXPOSURE TO STECP FIELD

FIG. 65

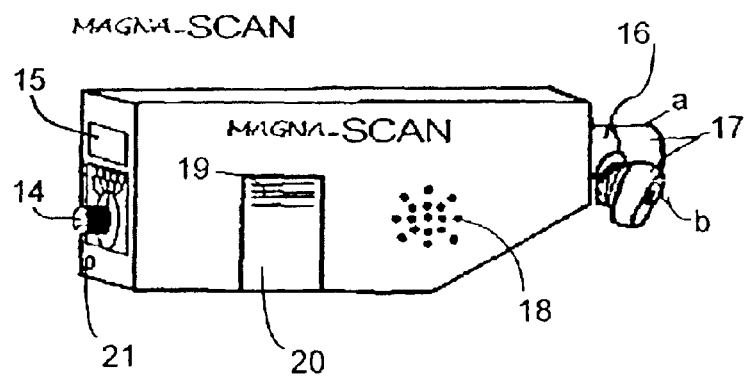

FIG. 66
FRONT VIEW

FIG. 67
REAR VIEW

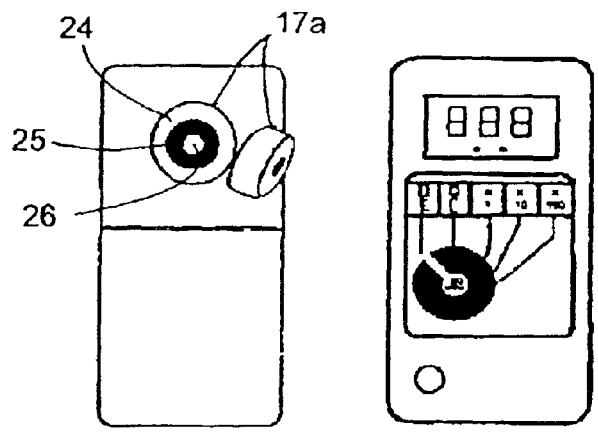

14 Function Control Switch
15. Liquid Crystal Display
16. Electrode Turrent
17 Removable Electrodes
18 Speaker
19. Battery Cover (Press to Remove)
20. Battery Cover 21. Earphone Jack
22. Battery Connector (see "Battery Compartment")
23. Battery (see "Battery Compartment")
24. Outer Electrode Ring
25. Insulator
26 Inner Electrode
17a. Conductance Annular Electrode
17b. Stimulating Annular Electrode containing the quadripolar

SCHEMATIC REPRESENTATION OF ANATOMICAL CONNECTIONS WITH PAIN PERCEPTION

METHOD AND APPARATUS FOR ALTERING THE CHARGE DISTRIBUTION UPON LIVING MEMBRANES WITH FUNCTIONAL STABILIZATION OF THE MEMBRANE PHYSICAL ELECTRICAL INTEGRITY

CROSS-REFERENCE TO RELATED APPLICATIONS

This is a continuation of U.S. patent application Ser. No. 09/484,801, filed Jan. 18, 2000, which has now issued as U.S. Pat. No. 6,461,288, which was a continuation-in-part of U.S. patent application Ser. No. 08/926,633, filed Sep. 10, 1997 now abandoned, incorporated herein by reference, which application claims priority of U.S. Provisional Patent Application Ser. No. 60/025,176, filed Sep. 10, 1996, now abandoned. That provisional application is also incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to magnetic devices for therapeutic application to the human body, and more particularly to a static field, quadripolar magnetic treatment device with flux return means and a focusing means to increase the intensity, focus and gradient of the field for placement against or in proximity to the human or other animal body. The present invention further relates to methods of use and construction of such magnetic treatment devices for the treatment of various animal diseases, complications and disorders such as, but not limited to, a) acute and chronic pain, b) cardiac dysfunction, c) seizure disorders, d) pain and edema sustained in minor burns, insect bites and bee stings) potentiation of pharmaceuticals and focusing and for concentrating the drug to the active site, f) protection of transplant organs, g) treatment of movement disorders, h) control of edema and pain as well as speed healing following surgical procedures, i) control of pain and sludging of sickled cells in sickle cell disease, j) foot pain and discomfort, k) Magna Scan device in the treatment of pain and other dysfunctions, l) potentiation of epidural anesthesia and epidural analgesia, m) Protection from cell injury and death following cell insults such as contusion, hypoxic stroke and infection, n) control of nausea and vomiting associated with pregnancy, motion, and chemotherapy, o) prevention of fertilization of ovum by sperm, p) cumulative trauma disorder in the workplace, q) a magnetic placebo which has no biological activity yet is magnetic and has all characteristics of the authentic device except the alternating poles and a significant field gradient.

2. General Background of the Invention

Magnetic fields have been applied to the human body for various therapeutic purposes for many centuries. For example, magnetic medical treatment devices for application against selected portions of the human body are disclosed in U.S. Pat. No. 3,921,620; method and apparatus for suppressing neuron action potential firings U.S. Pat. No. 5,312,321; magnetic plasters for improving circulation are disclosed in U.S. Pat. No. 4,489,711; magnetic fields for stimulation of bone growth are disclosed in U.S. Pat. No. 4,105,017; and magnetic stimulation of nerve cells has been accomplished with devices such as the Cadwell Magneto-Electric Stimulator (MES-10) manufactured by Cadwell Laboratories, Inc. Of Kennewick, Wash.

Various disease states, tissue and organ malfunction may be the result of loss of membrane stability and normal permeability. These membranes may be cellular of intracellular, but in any case represent malfunction of excitable tissue. This malfunction of excitable tissue may be due to alteration of ion channel function. These various disease and states of malfunction may also be related to alteration of receptor sites or agonist sites of enzymes and/or other such dynamic systems within living organisms and more particularly the human animal. A great variety of symptoms and malfunctions may occur, such as, but not limited to, the above listed disease and/or disorder states.

Unfortunately, many types of ailments, including chronic pain, poor localized blood flow, cerebral edema and certain seizures and injuries cannot be successfully treated with conventional drug, physical therapy or surgical therapies. Because such ailments are often untreatable with conventional therapies, there is a need for alternative therapies that relieve these previously untreatable or poorly treatable conditions.

U.S. Pat. No. 5,312,321 (issued May 17, 1994) and U.S. Pat. No. 5,941,902 (issued Aug. 24, 1999) are also incorporated herein by reference.

BRIEF SUMMARY OF THE INVENTION

The apparatus of the present invention solves the problems confronted in the art in a simple and straightforward manner. What is provided is a therapeutic static magnetic treatment device adapted for placement of at least four magnetic flux generator poles is applied such that they may be applied to the animal or human body as described for the various applications revealed herein. The device comprises a plurality of static magnetic bodies in each head of the applications, having at least two positive and two negative magnetic poles substantially in a single plane, the magnetic poles being oriented to define the four vertices of a quadrilateral shape, the two positive poles defining opposite diagonal vertices, and the two negative poles defining opposite diagonal vertices of the quadrilateral shape, each of the magnetic poles being magnetically attracted by the oppositely charged poles and being magnetically repelled by the like charged poles.

An object of the invention is to provide a static magnetic device for production of a magnetic field for treatment of pain disorders, such a device being powered by a particular static magnetic field and having, inter alia, an alternating polarity, quadripolar array which generates a 3 dimensional, steep field gradient (greater than 0.25 mt/mm) with a homogenous field.

It is a further object of this invention to provide an alternating, quadripolar array in which each of the poles is in the shape of two cones joined at the directrix of the cone with the vertex of the two cones lying in a perpendicular axis of a circular directrix.

Furthermore, there is taught a method and apparatus for altering the charge distribution upon living membranes with functional stabilization of the membrane physical electrical integrity.

An object of this invention to provide a device that alters the stability of excitable membranes and other charged structures and systems in order to treat ailments in animals.

Another object of this invention is to present a global technique for controlling the physical and electrical stability of irritable membranes (either cell walls or intra-cellular organelles) and altering receptor sites, i.e. enzymes, hormones and/or drugs.

There is further taught a device in which the desired biological effects are directly related to the magnitude of the gradient in the x, y and z axis and therefore the magnitude of the vector or summation gradient.

In the Detailed Description an array of containment means, support means, energizing means and control means of the embodiments will be presented for a variety of therapeutic purposes along with support data for the application.

The accompanying drawings, which are incorporated herein and constitute a part of this specification, illustrate presently preferred embodiments of the invention, and together with the description, serve to explain the principles of the invention.

BRIEF DESCRIPTION OF THE DRAWINGS

Device

FIG. 1 is a perspective view of an embodiment of a magnetic device in accordance with the principles of the invention.

FIG. 2 is a cross section of the magnetic device in FIG. 1 along the line 2—2.

FIG. 3 is a plan view of the magnetic device in FIG. 1.

A. Pain and Swelling

Figure 4:
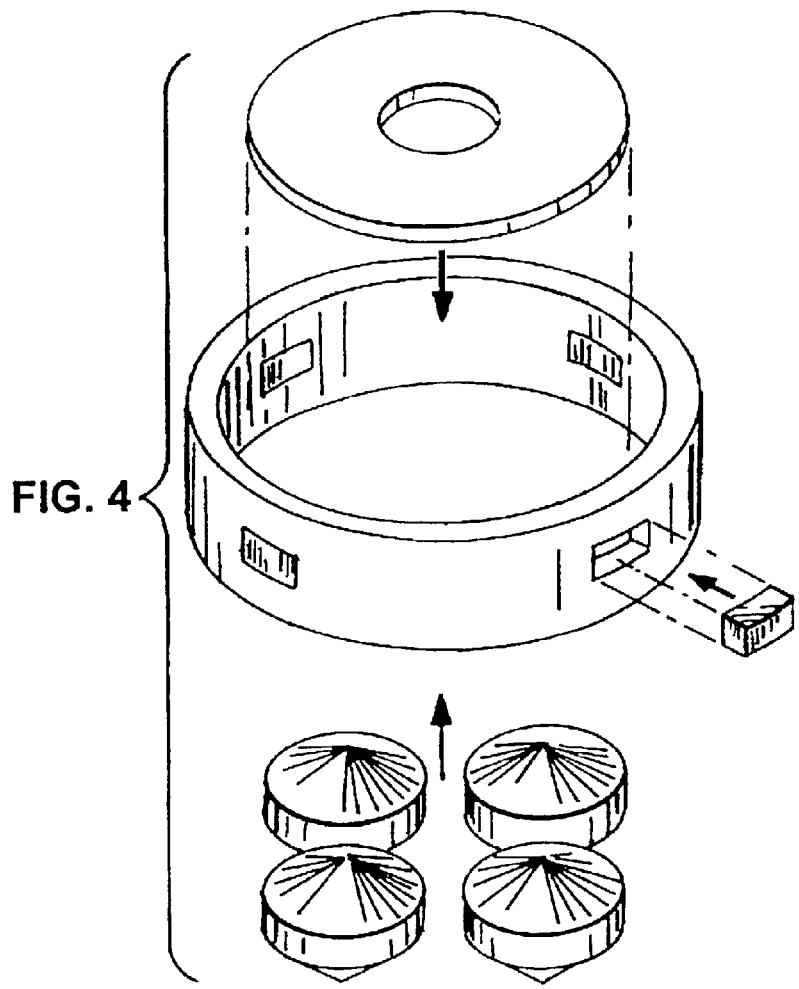
FIG. 4 is an exploded diagram of the magnetic device in FIG. 1.
Figure 5:
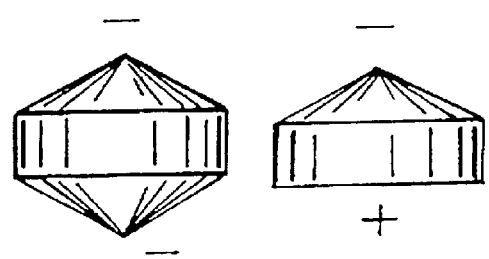
FIG. 5 is a side view of a "coned" magnet from the magnetic device in FIG. 1. Also included is a "single coned" magnet.
Figure 6:
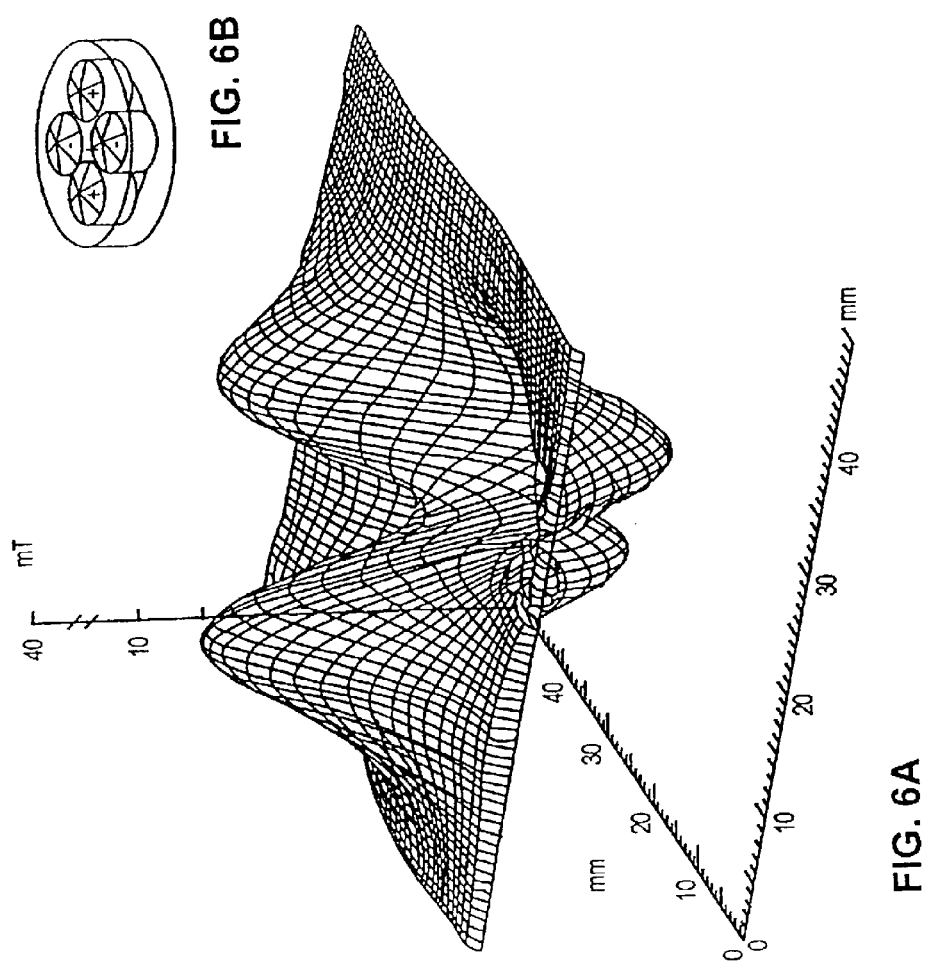
FIGS. 6A–6B are illustrations of the magnetic field of magnetic device of FIG. 1, and another illustration of that device respectively.
Figure 7:
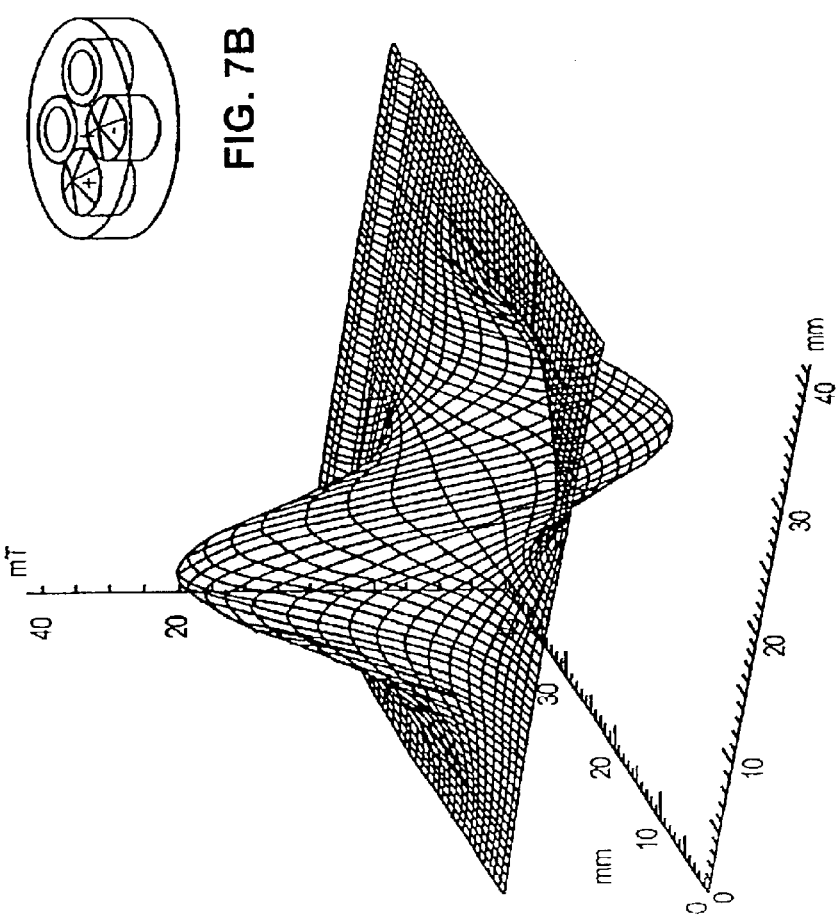
FIGS. 7A–7B are illustrations of the magnetic field of another magnetic device (with only two "coned" magnets) and an illustration of that device respectively.
Figure 8:
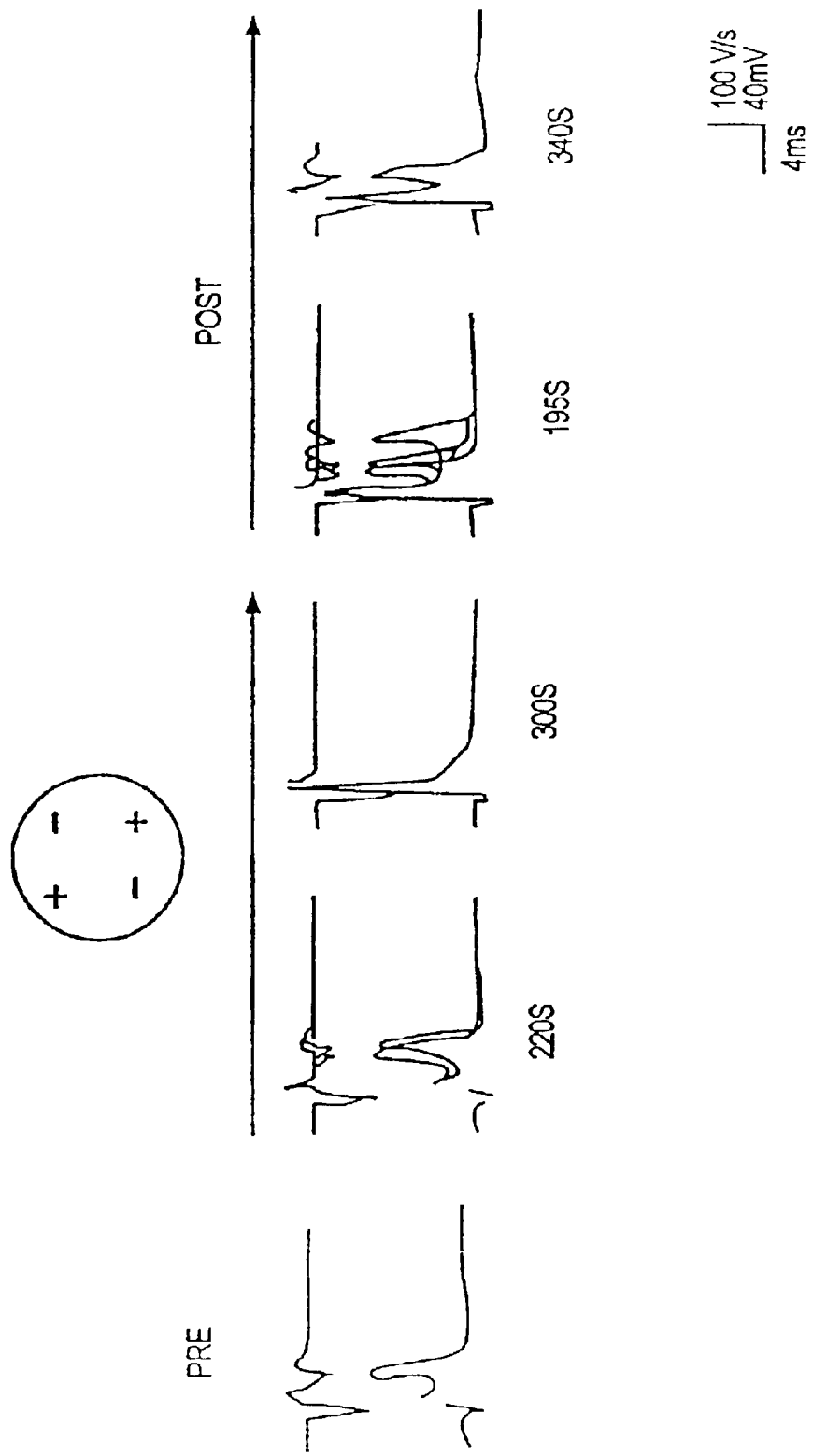
FIG. 8 shows oscilloscope traces from texts on mammalian nerve cells conducted using the magnetic device of FIG. 1.
Figure 9:
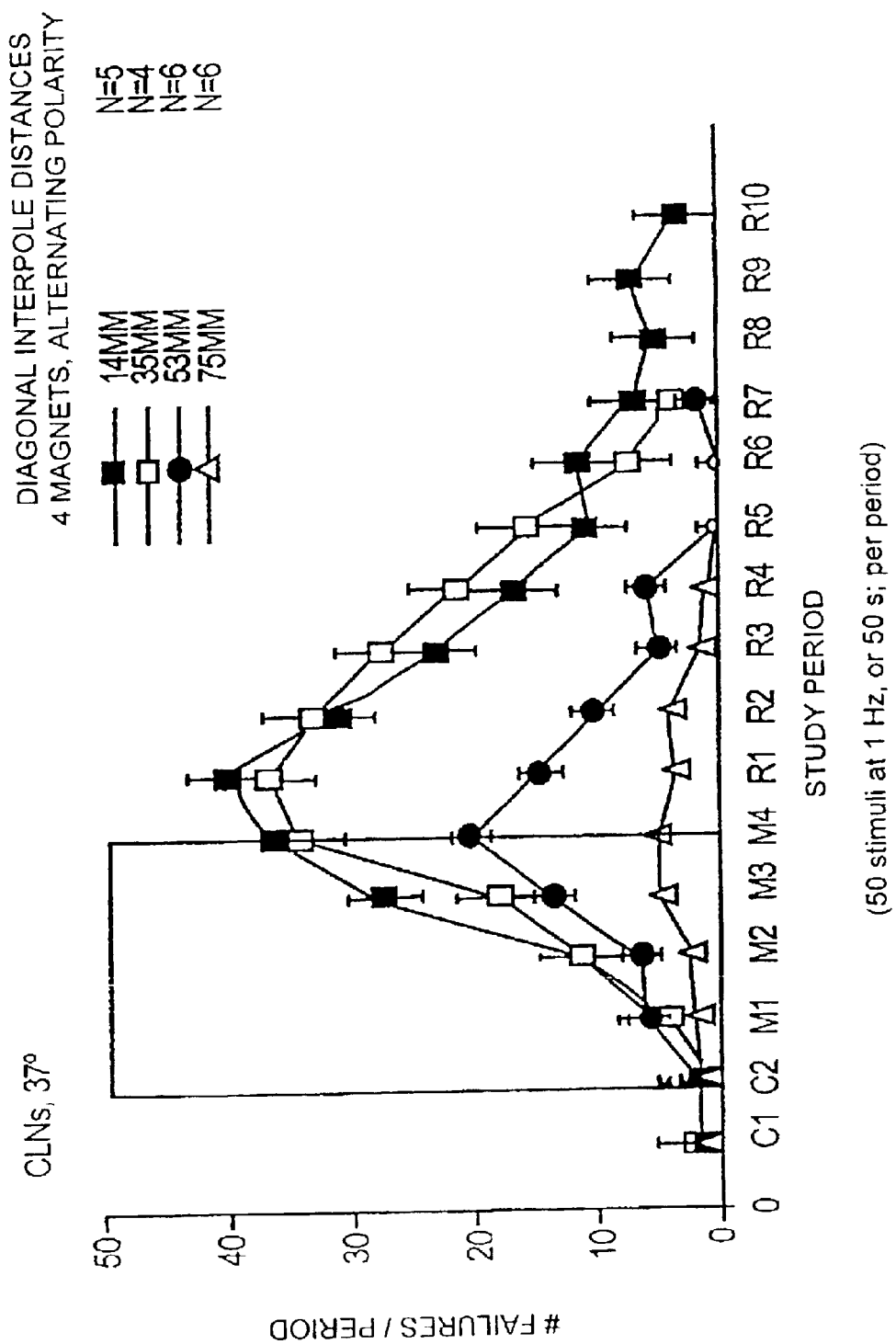
FIG. 9 is a graph comparing the average number of times neurons failed to elicit action potentials in response to applied stimuli before, during and after exposure to the magnetic device of FIG. 1 and to similar magnetic devices in which the magnets were spaced from each other at various distances.
Figure 10:
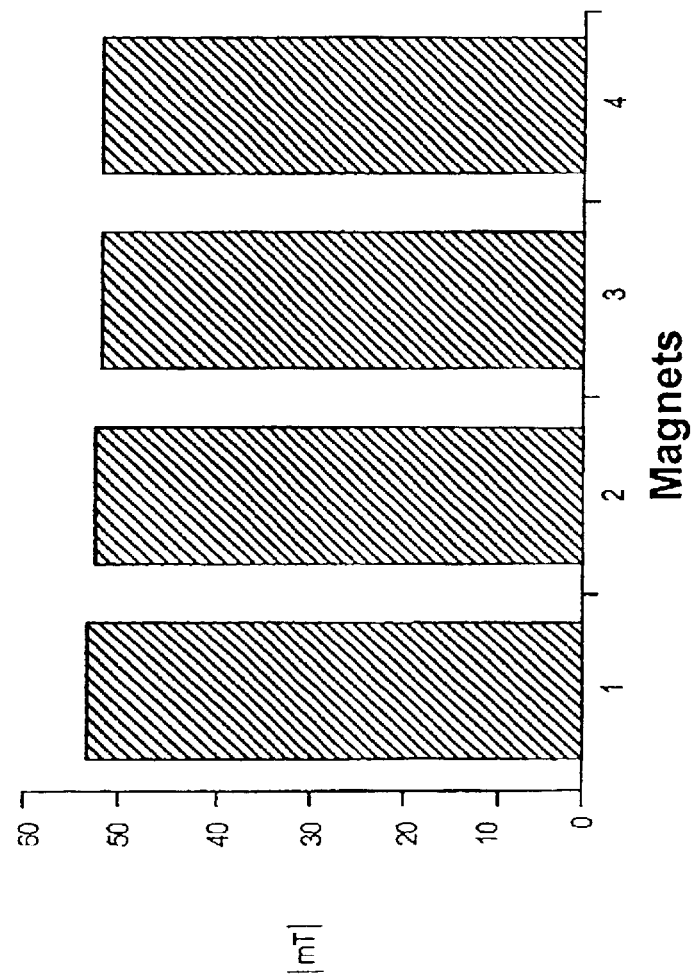
FIG. 10 is a bar graph representing the magnetic energy in milli Tesla (mT) as measured over the center of the pole in each of the 4 poles of a device as in FIG. 1 soon after it was manufactured in 1993.
Figure 11:
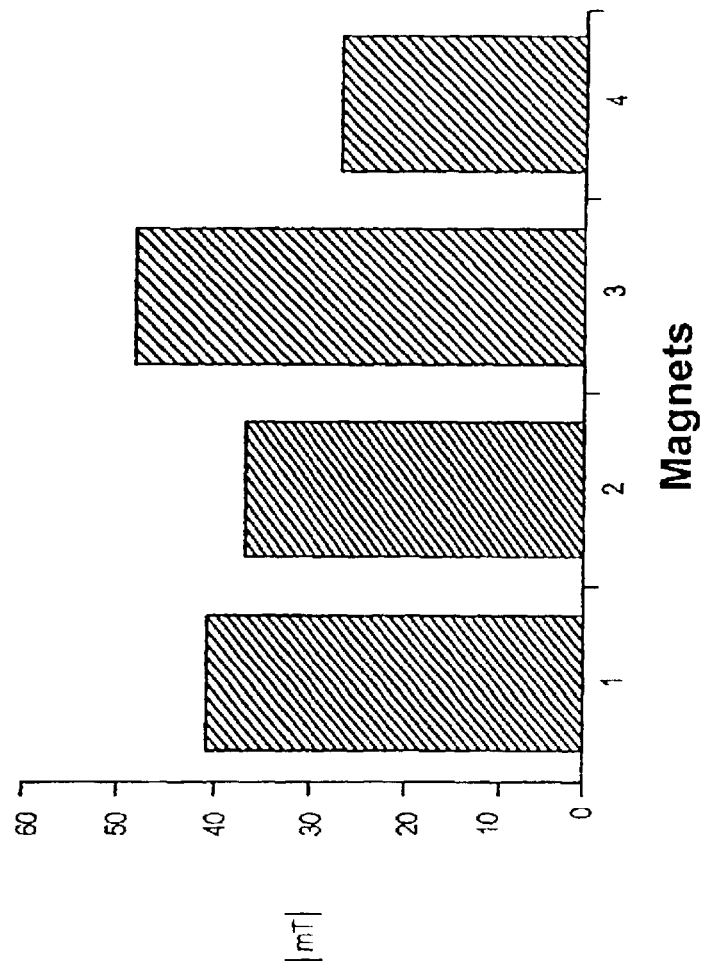
FIG. 11 is a bar graph representing the magnetic energy in milli Tesla (mT) as measured over the center of the pole in each of the 4 poles of a device as in FIG. 1 in 1993, the device being manufactured in 1989.
Figure 12:
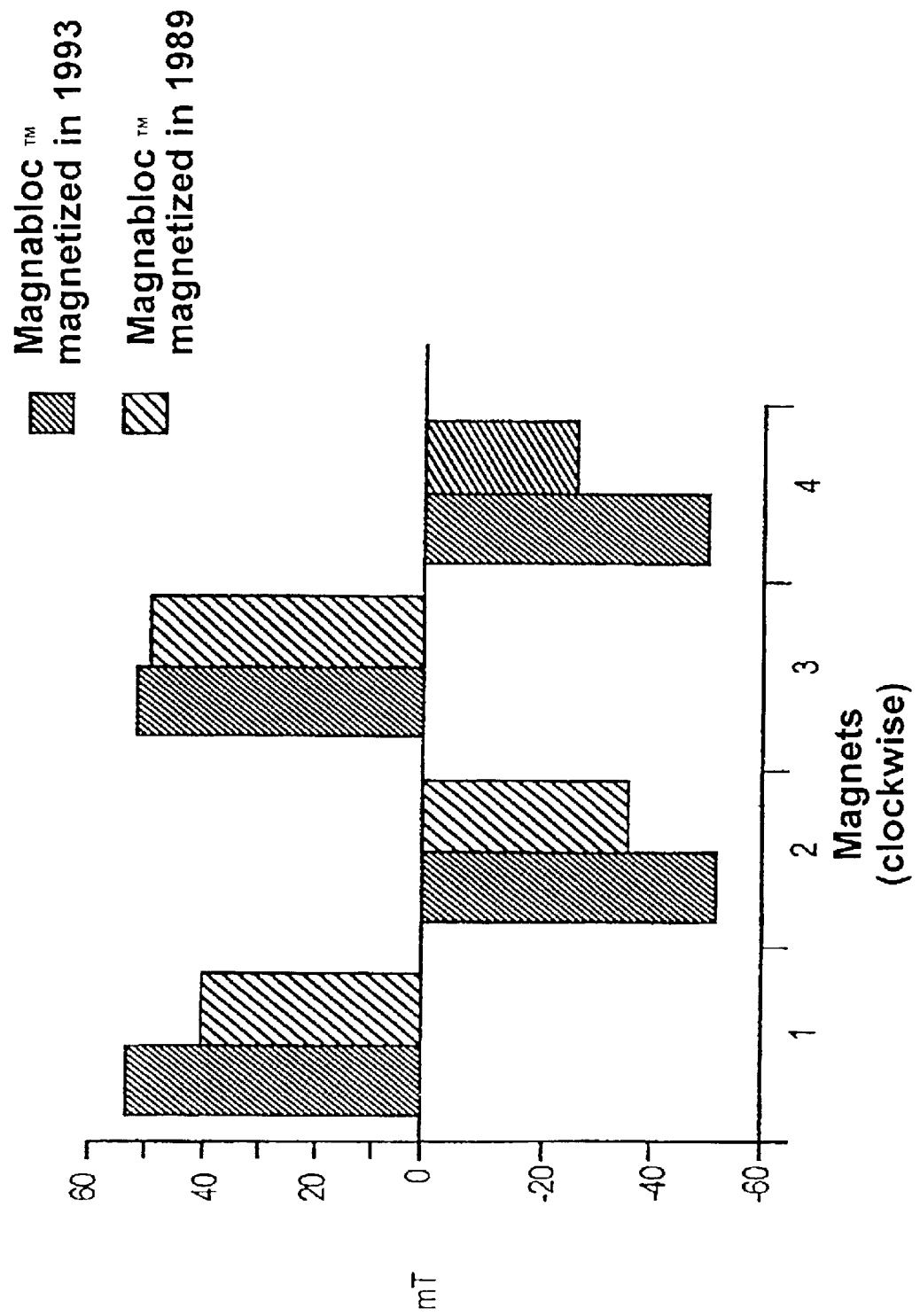
FIG. 12 is a bar graph representing the magnetic energy in milli Tesla (mT) as measure in clockwise fashion over each pole of a device in FIG. 1 which was manufactured in 1989 and 1993—measurement was done in 1993.
Figure 13:
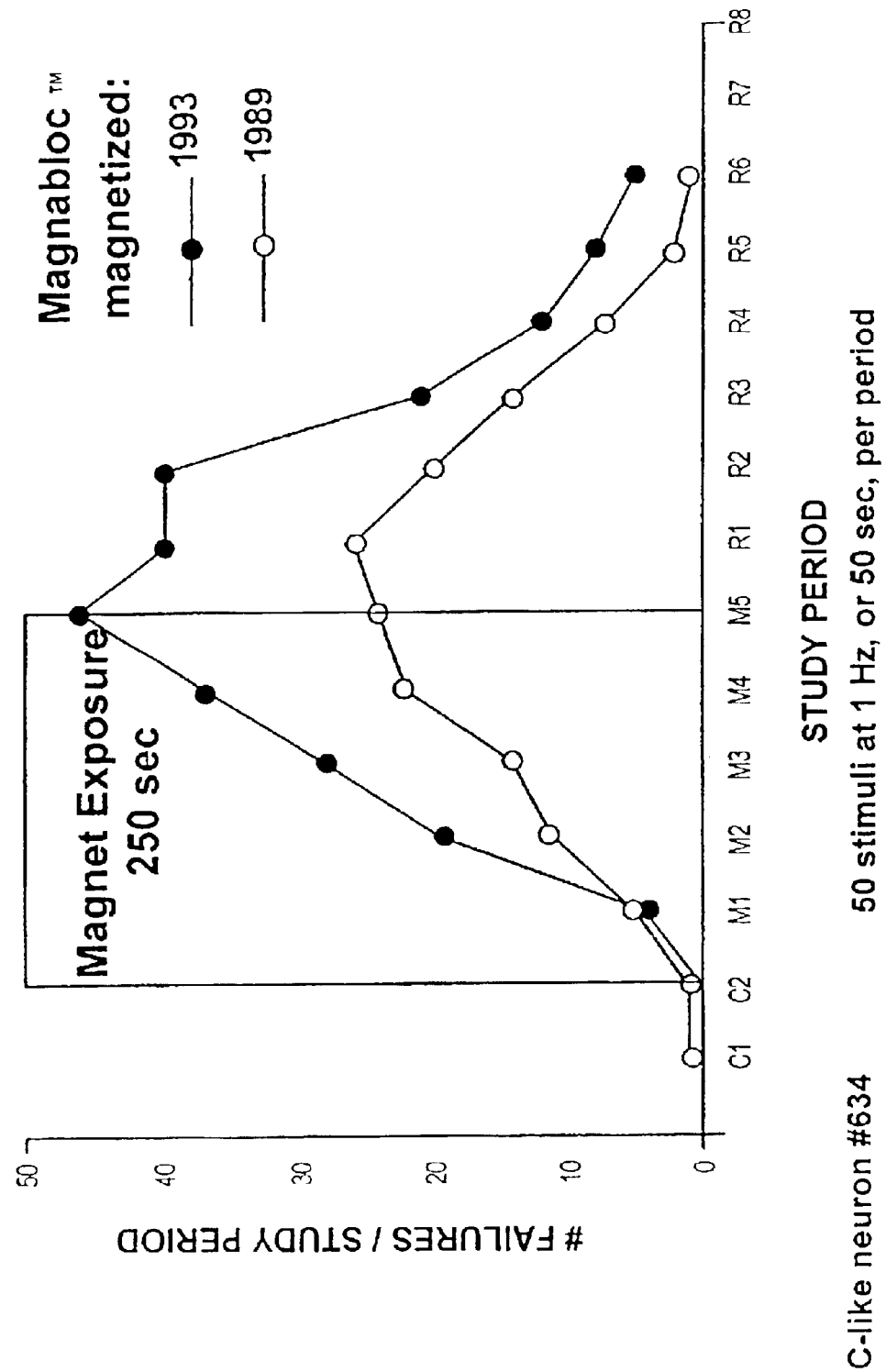
FIG. 13 is a graph comparing the average number of times neurons failed to elicit action potentials in response to applied stimuli during exposure to the magnetic device of FIG. 1 for devices manufactured in 1989 (50% loss of energy in one pole) and 1993 (full energy in each of 4 poles).
Figure 14:
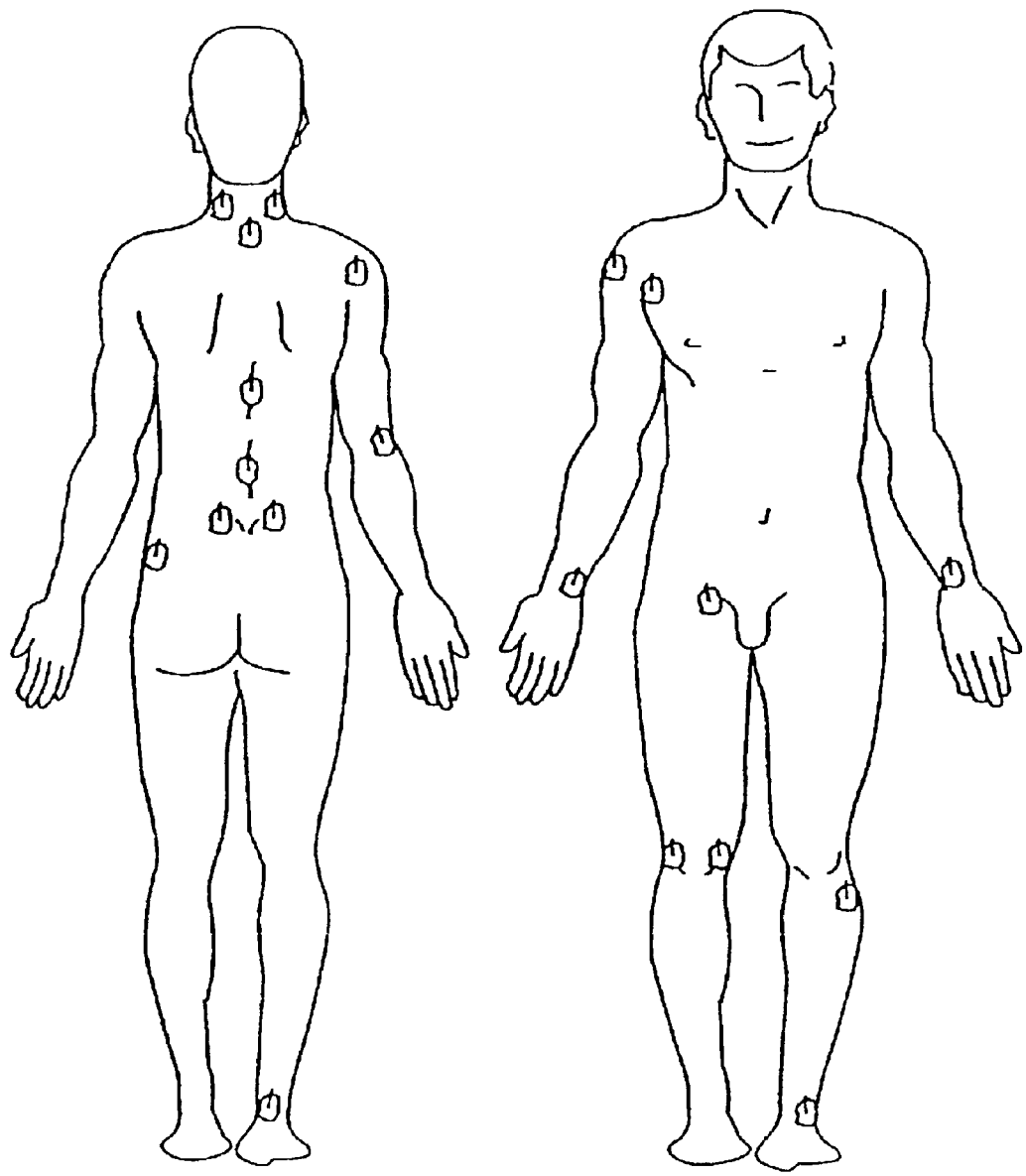

FIG. 14 is a view of a treatment application to the human body for related pain and smelling applications.

B. Pain and Edema Sustained in Minor Bums, Insect Bites and Bee Stings

Figure 15:
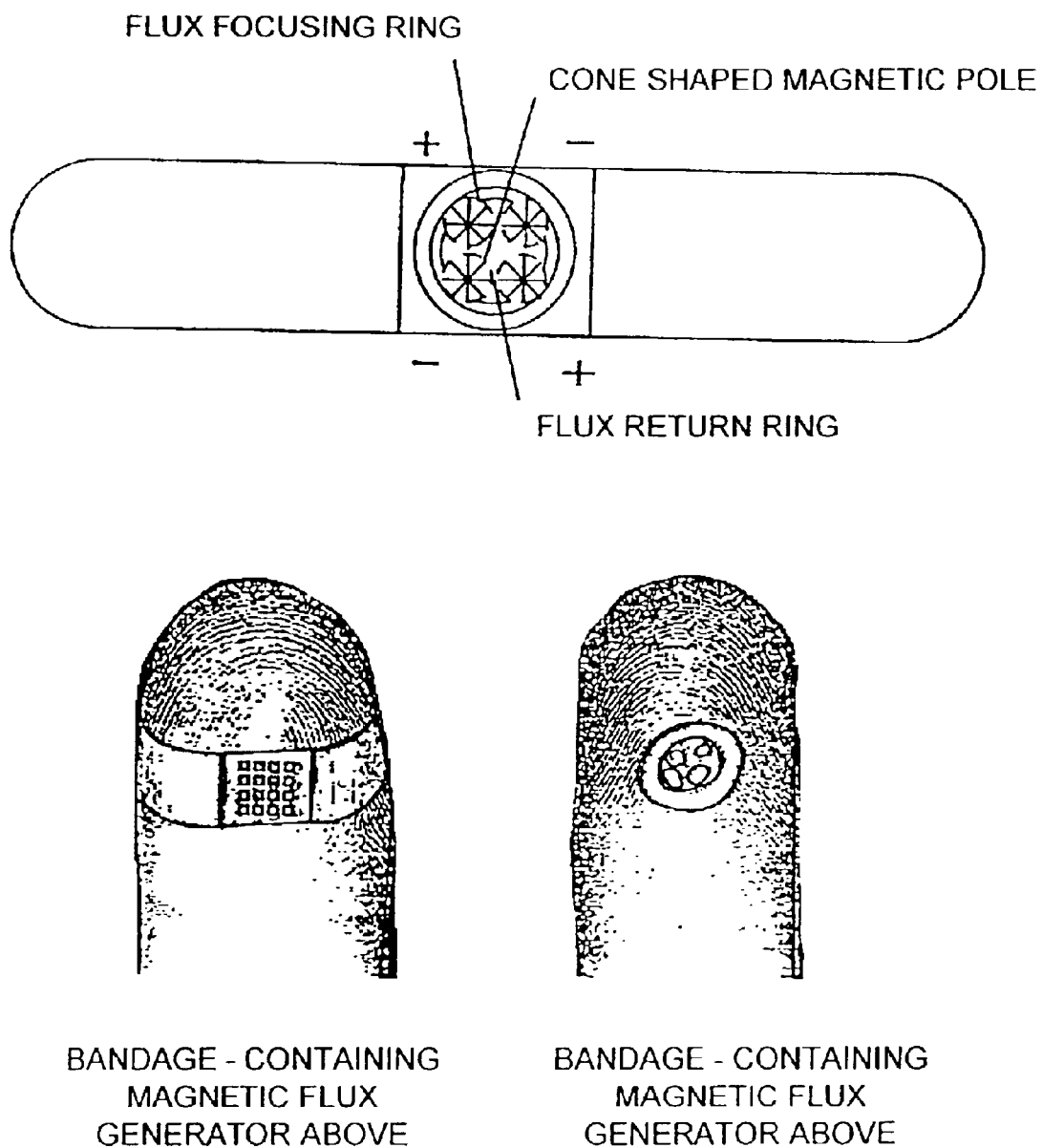

FIG. 15 Human Figure with "Band Aide"—Round and rectangular

C. Foot Pain and Discomfort

Figure 16:
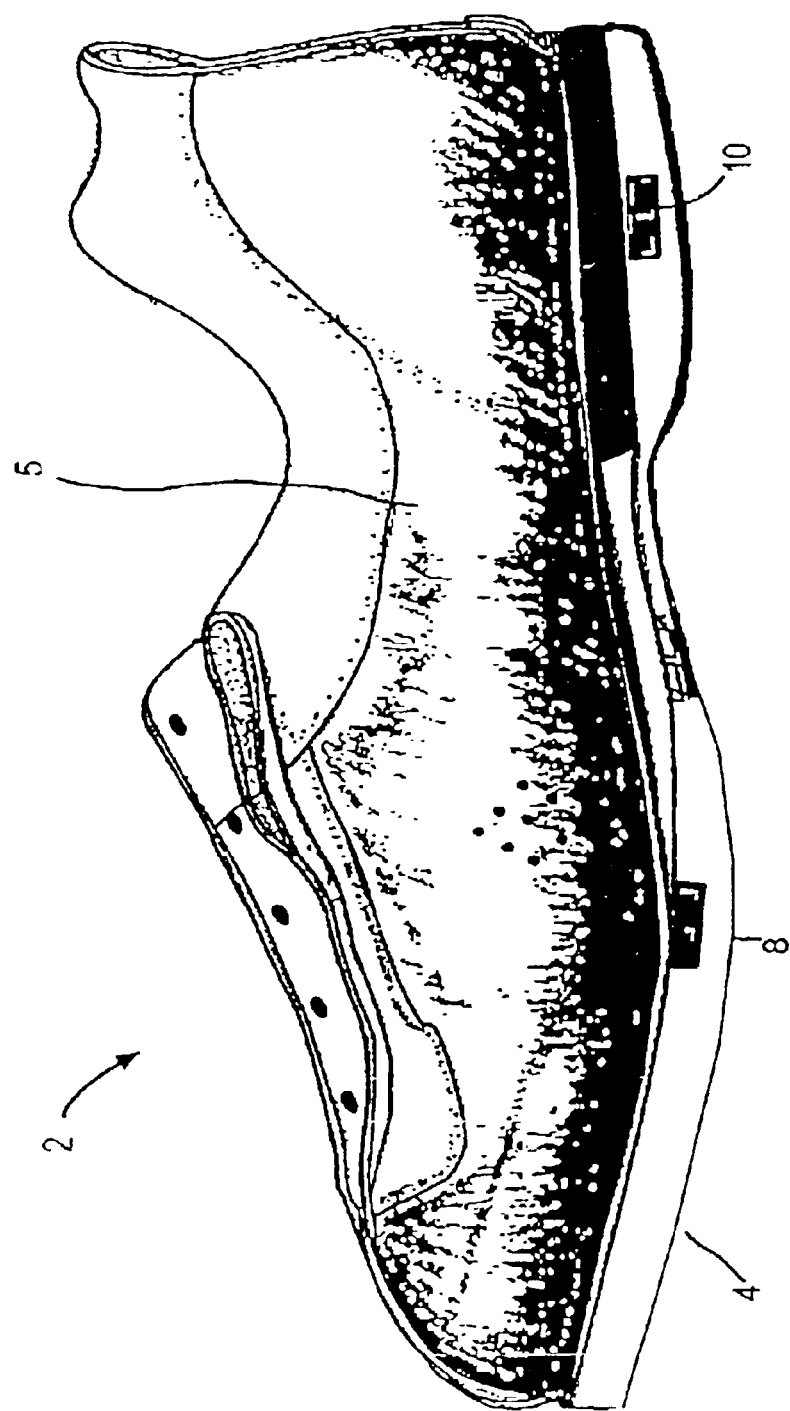

FIG. 16 is a side cross-sectional view of a shoe according to one embodiment of the invention.

Figure 17:
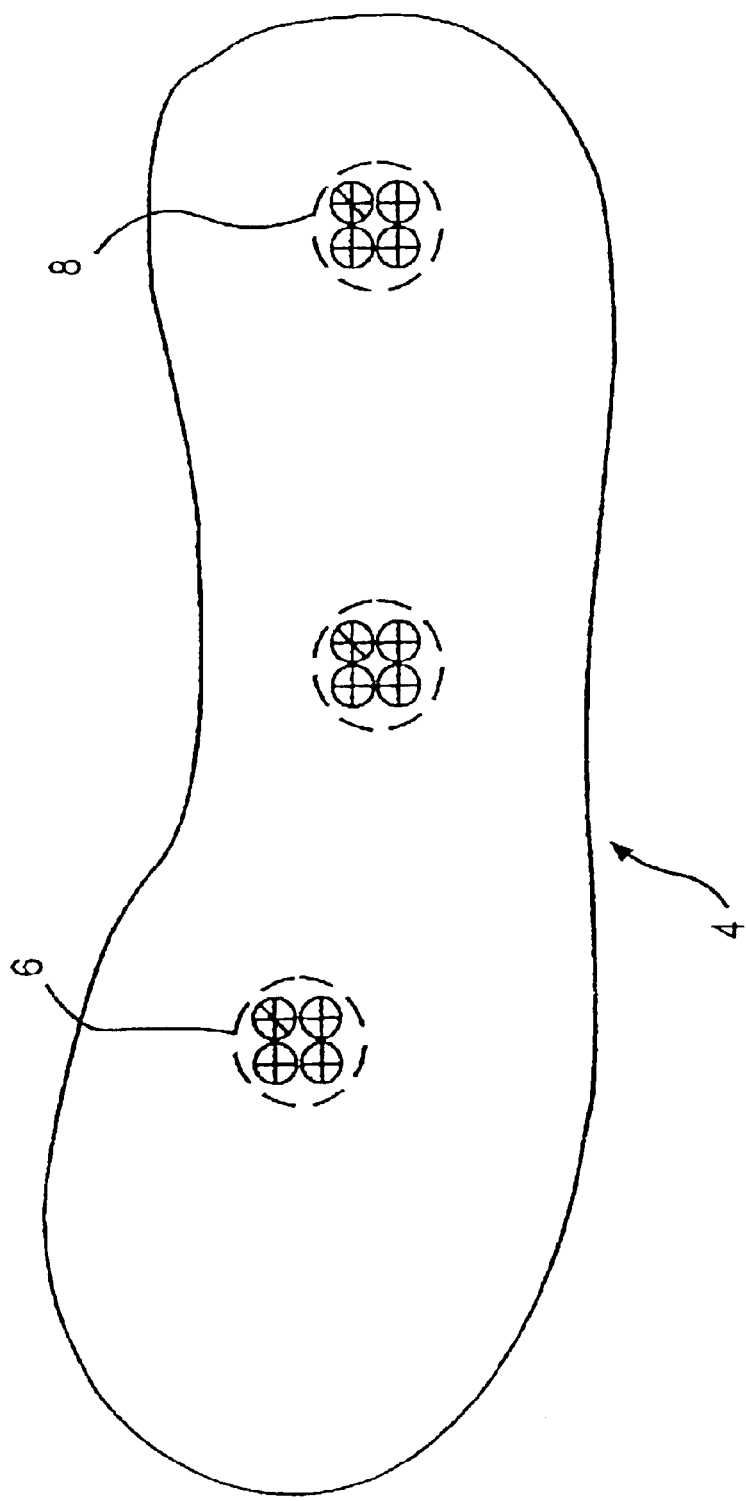

FIG. 17 is a top cross-sectional view of the sole of the shoe of FIG. 1.

Figure 18:
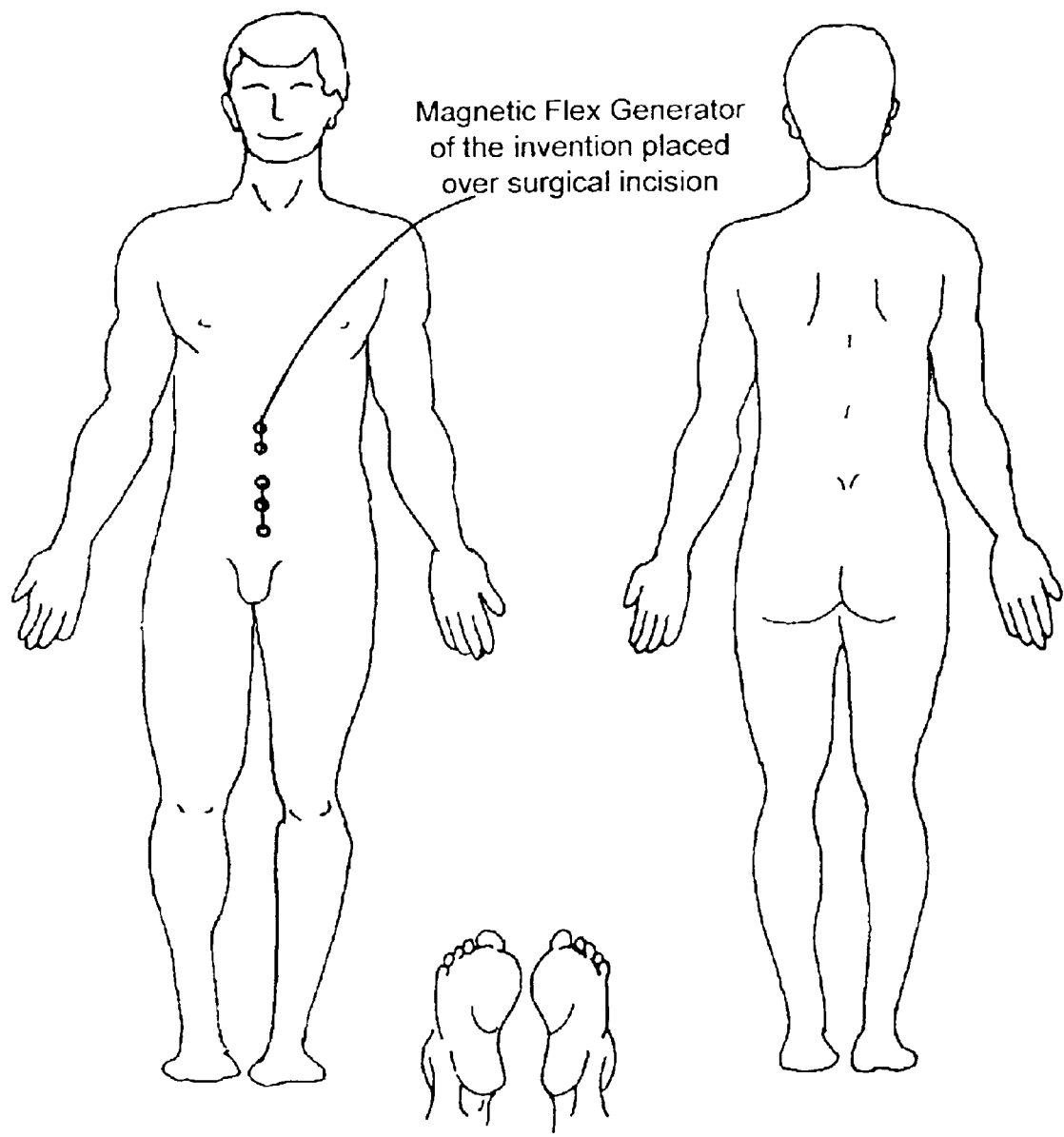
Figure 20:
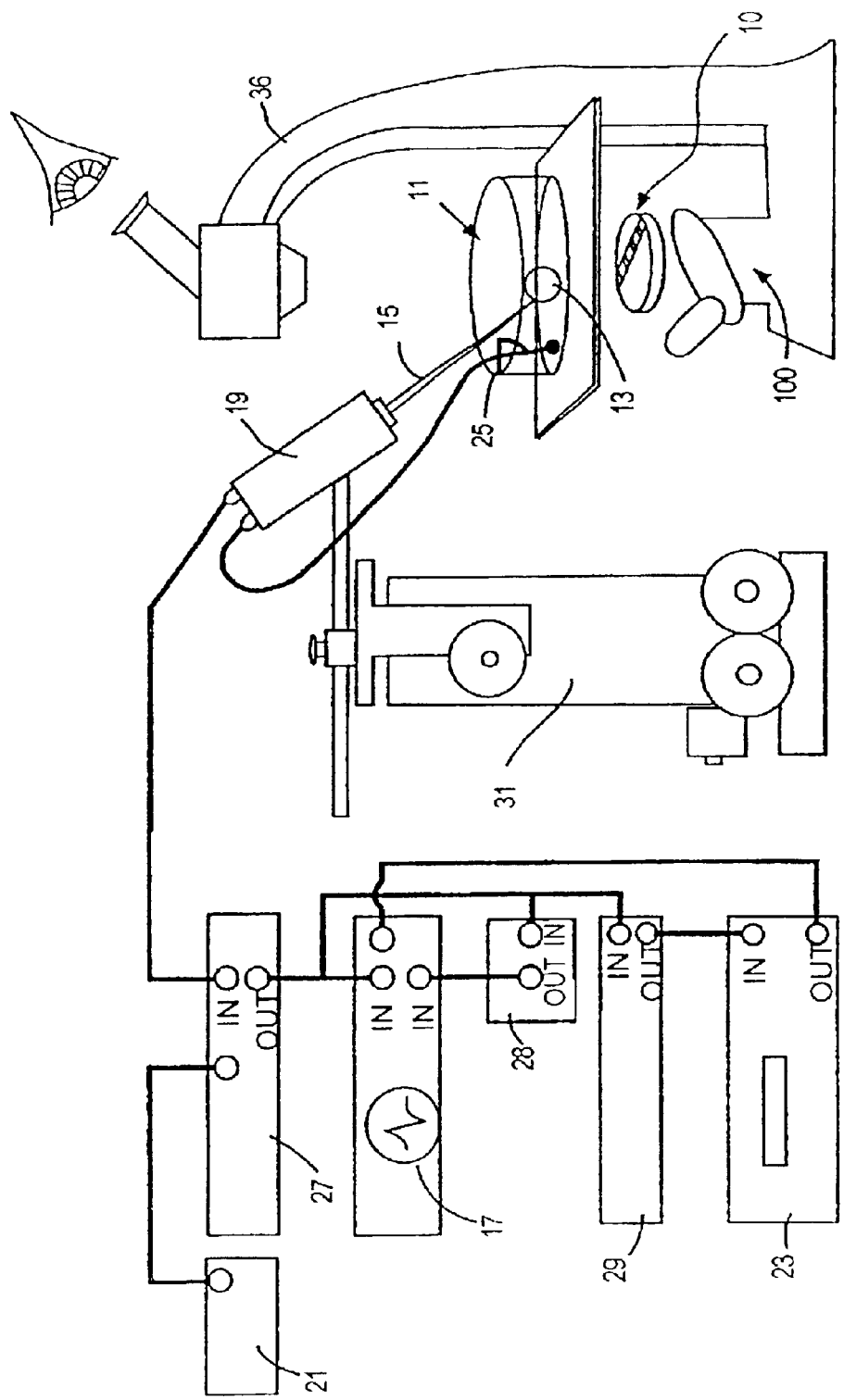

E. Control of Edema, Pain and Swelling as well as Speed Healing Following Surgical Procedures FIG. 18 Placement over surgical incision on human F. Potentiation of Epidural Anesthesia and Epidural Analgesia FIG. 20 is a side view of an experimental design used to monitor the suppression of nerve cell action potentials with the method of the present invention.

Figure 21:
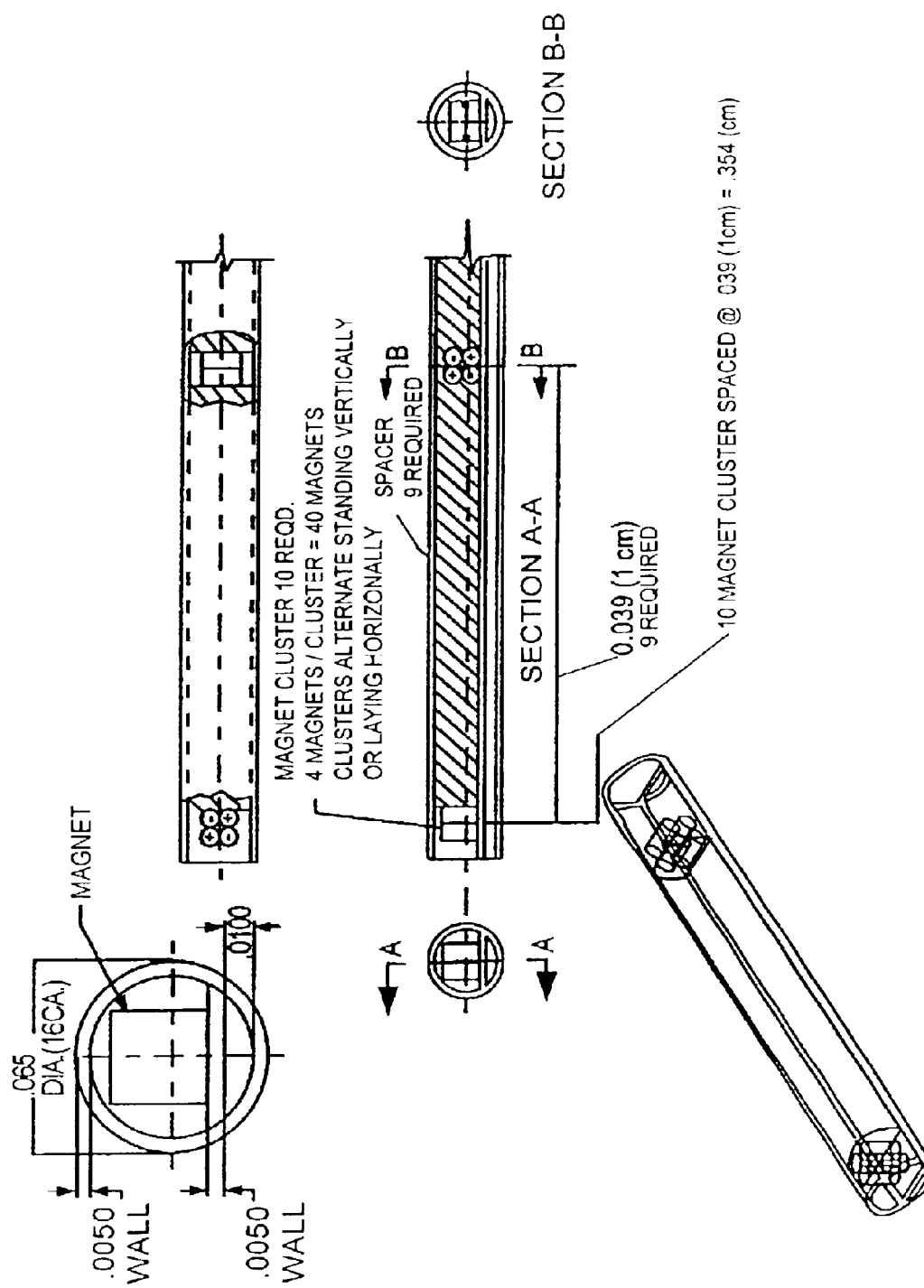

FIG. 21 is a plan view of the epidural catheter that may be used in applying the method of the intervention.

Figure 22:
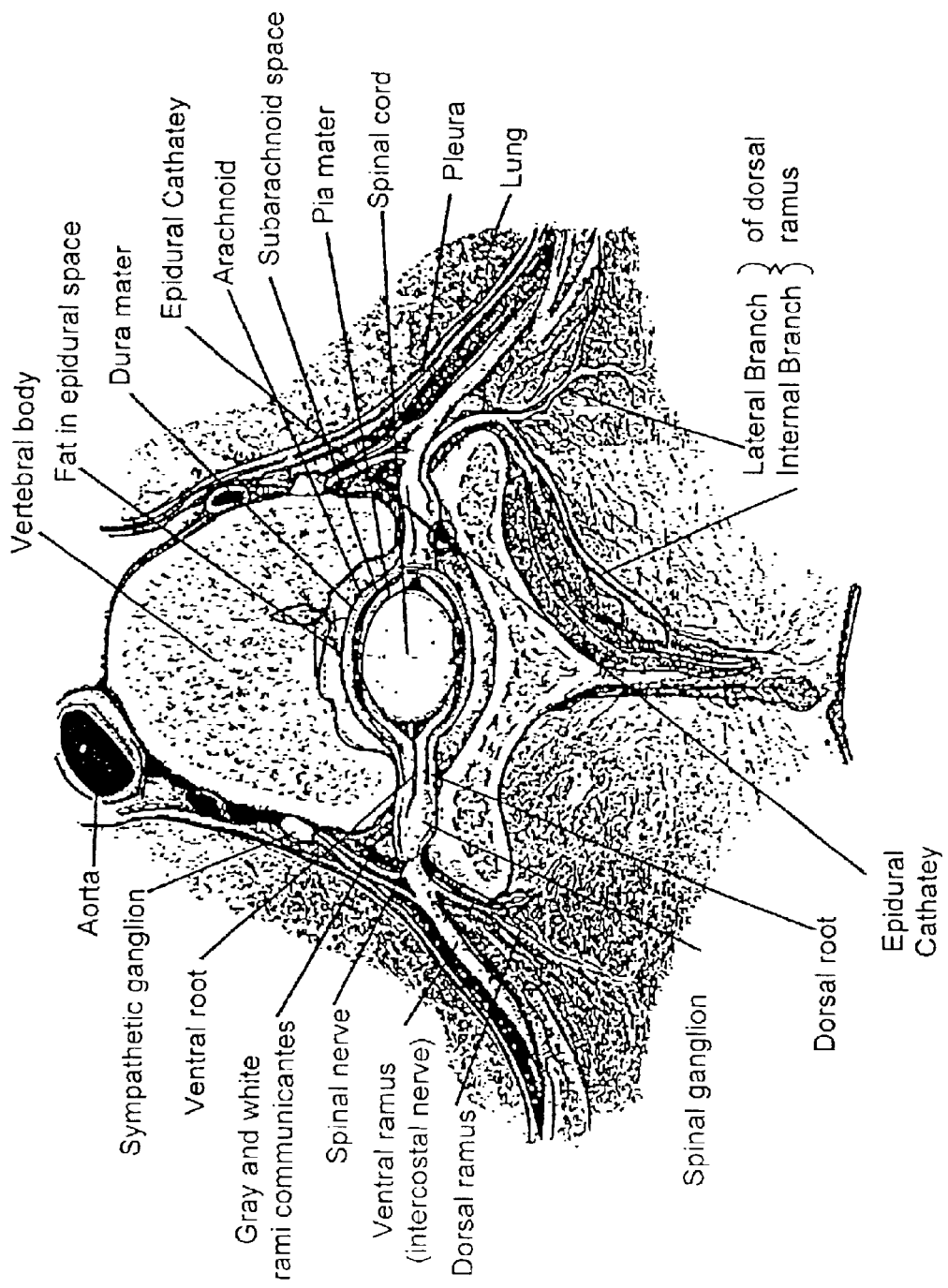

FIG. 22 is a cross-sectional view through a thoracic vertebrae, showing placement of the epidural catheter.

FIG. 23 is a perspective view of an embodiment of a magnetic device without "cones" in accordance with the principles of the invention.

FIG. 24 is a cross section of the magnetic device in FIG. 23 along the line III—III.

FIG. 25 is a plan view of the magnetic device in FIG. 23.

FIG. 26 is a side view of a magnet (without cones) from the magnetic device in FIG. 23.

Figure 27:
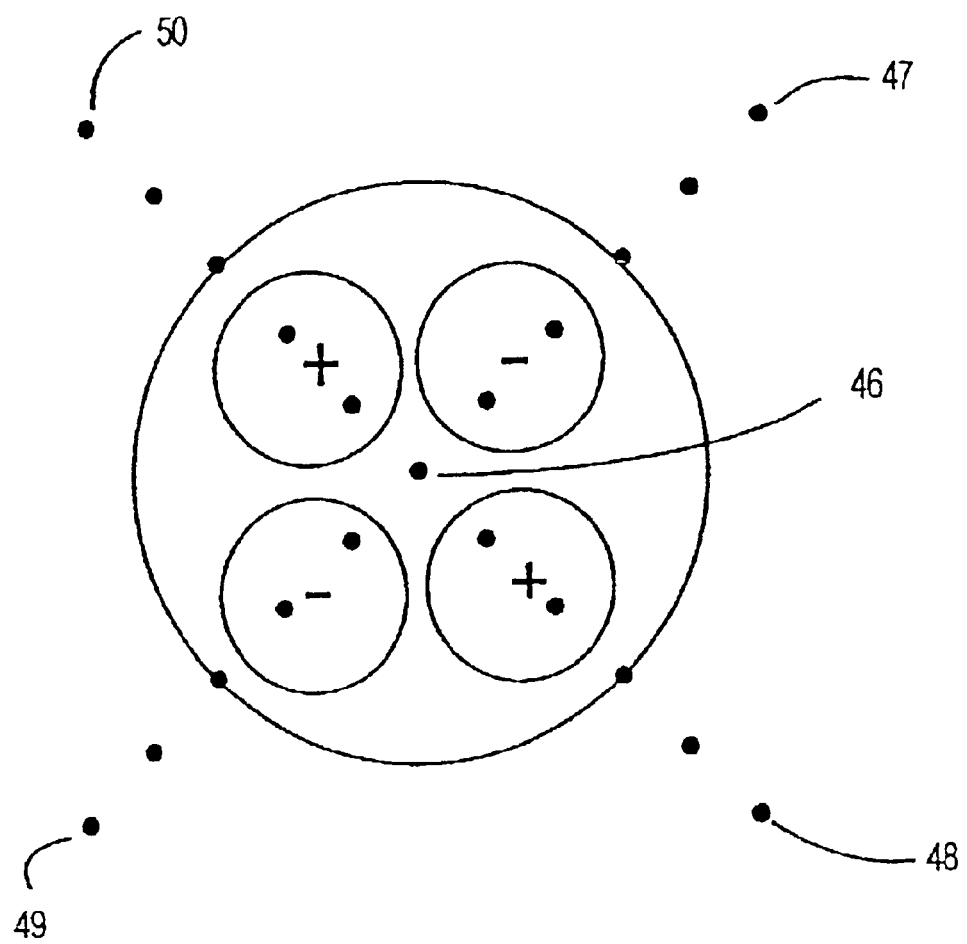

FIG. 27 is a top view of the magnetic device of FIG. 23, with dots added to designate surface magnetic field measurement locations.

Figure 29:
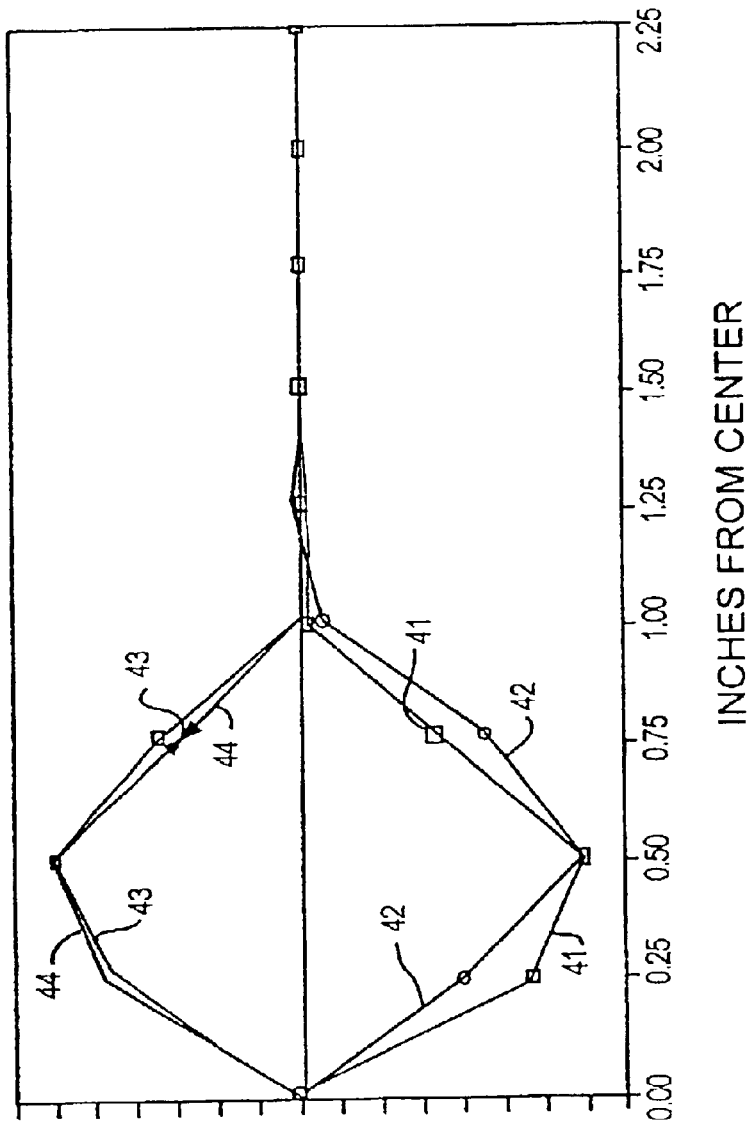

FIG. 29 is a graph of magnetic field measurements taken at the measurement locations designated in FIG. 27.

Figure 36:
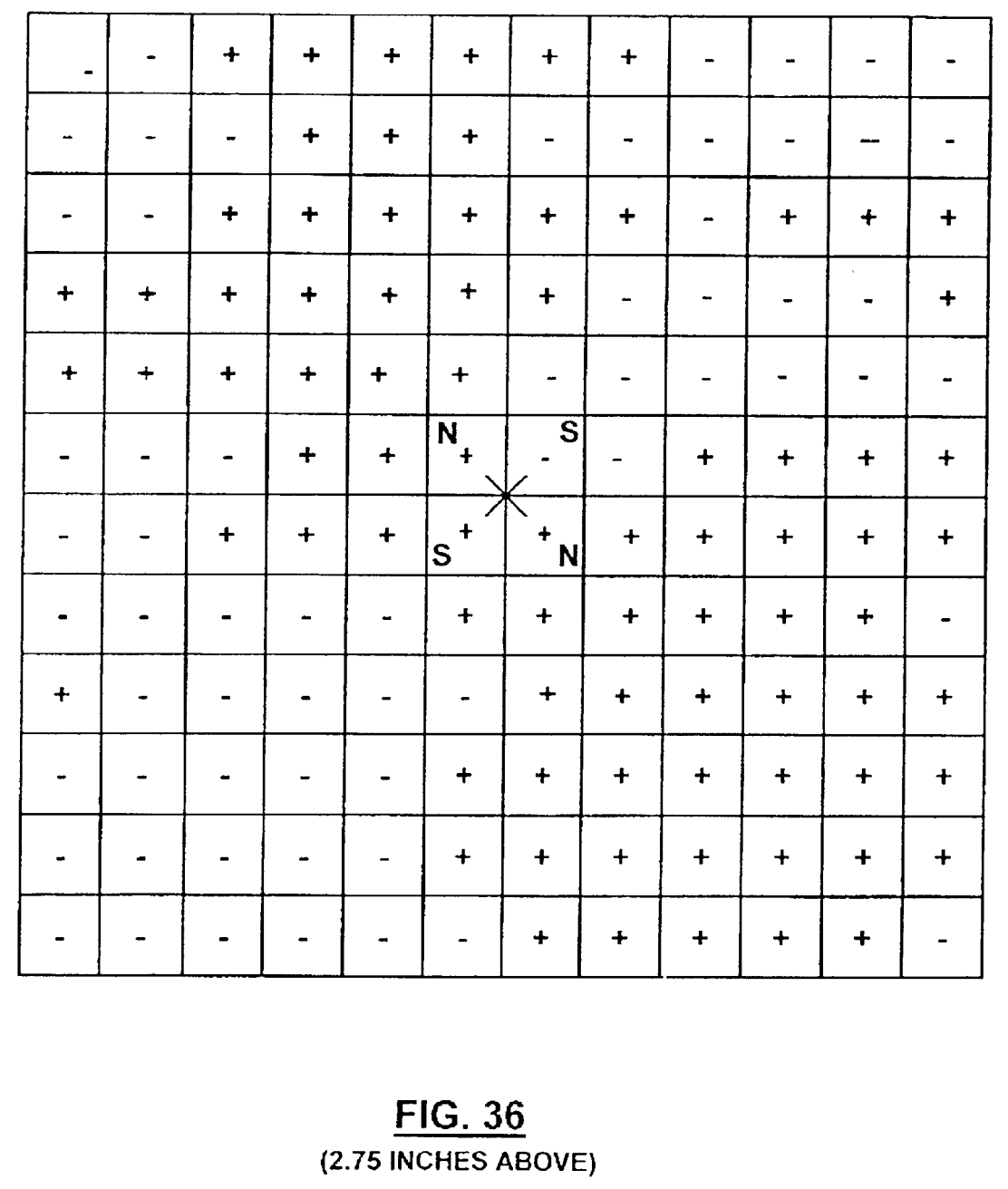

FIGS. 30–36 are grids of magnetic field measurements taken at various distances from the surface of the magnetic device of FIG. 23.

Figure 37:
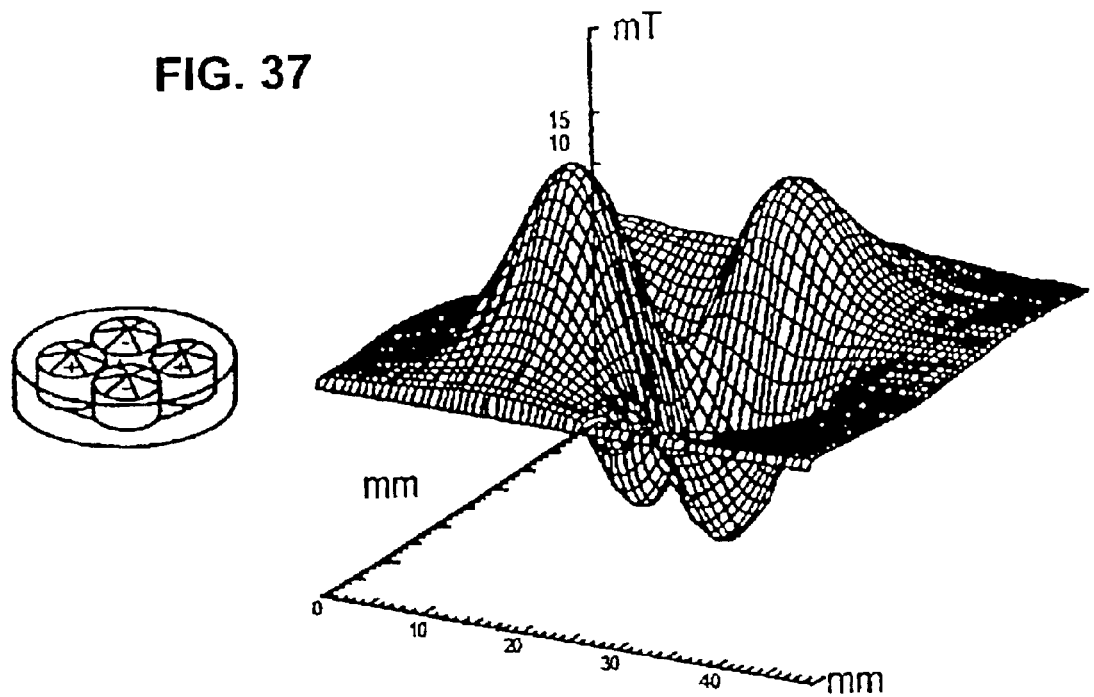

FIG. 37 is a magnetic field plot for the magnetic device of FIG. 23.

Figure 38:
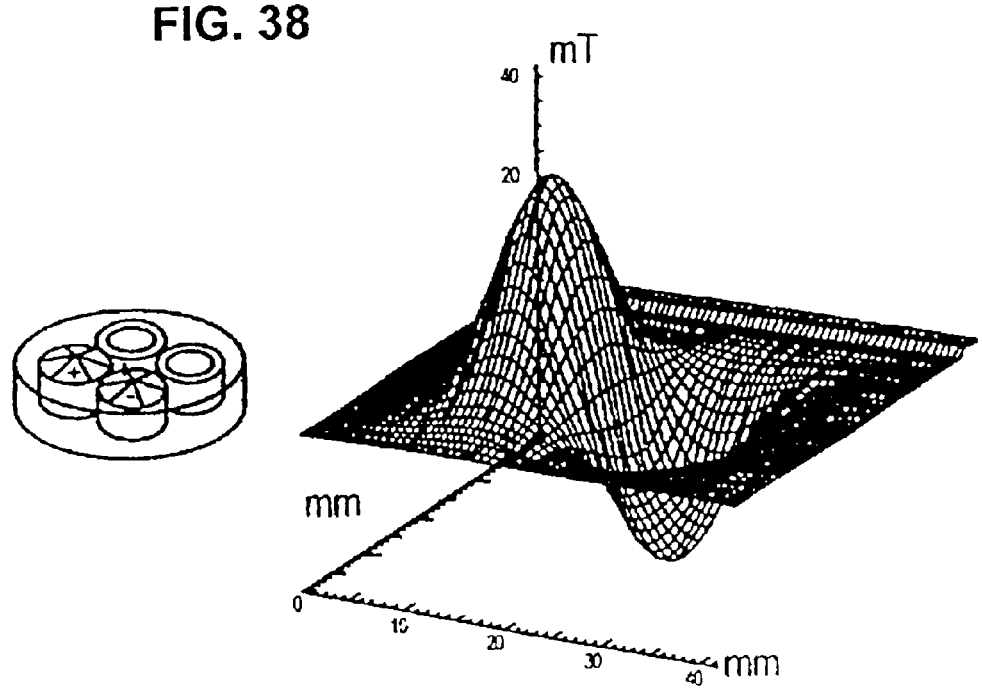
Figure 39:
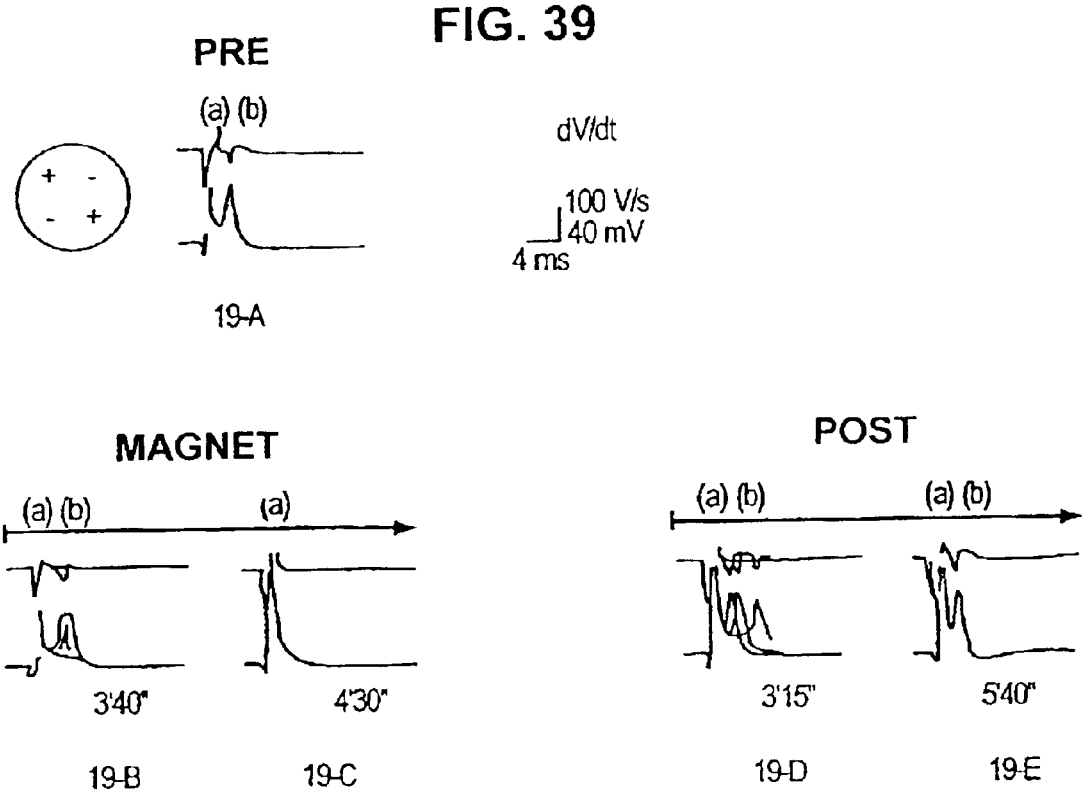
Figure 40:
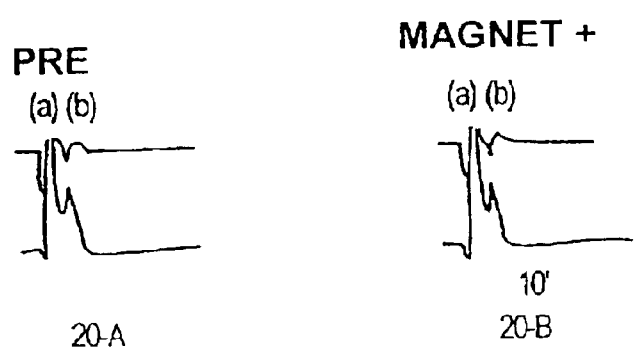
Figure 41:
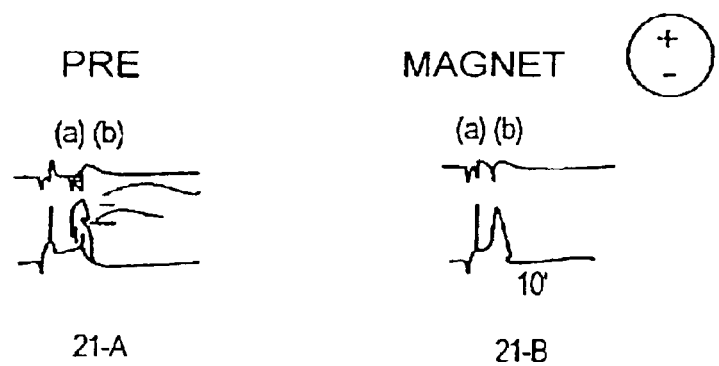
Figure 42:
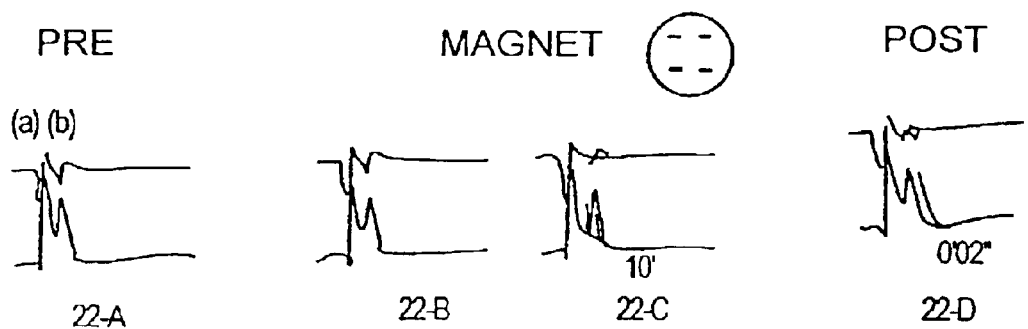
Figure 43:
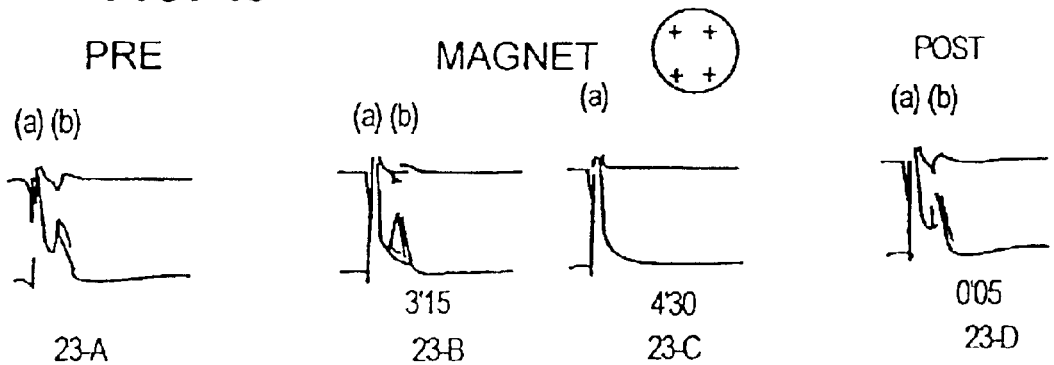

FIG. 38 is a magnetic field plot for a magnetic device having one positive and one negative magnetic pole.

FIGS. 39–43 are a series of diagrams showing the output on an oscilloscope connected to an electric probe inserted in a mammalian nerve cell. 3

Figure 44:
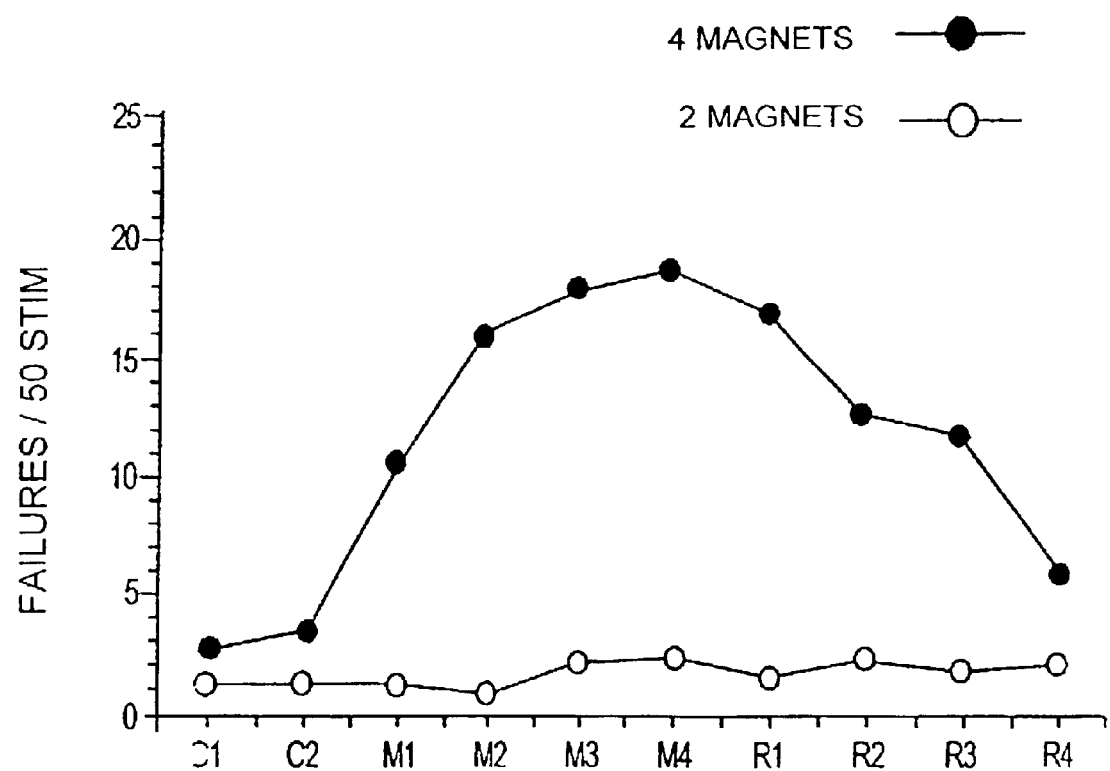

FIG. 44 is a graph showing average number of times neurons failed to elicit action potentials in response to stimuli applied as described in Example No. 9.

Figure 45:
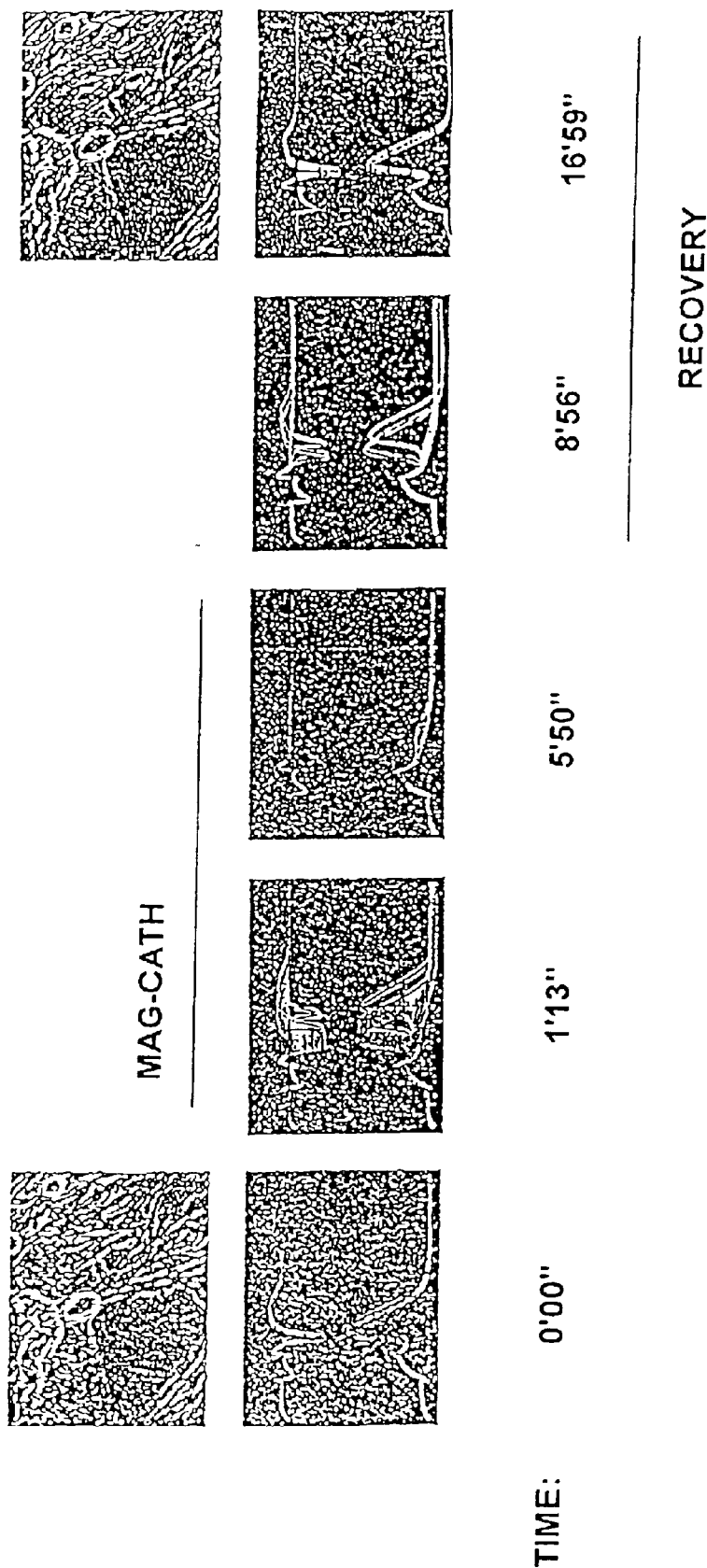

FIG. 45 is a photographic series showing the output on an oscilloscope connected to an electric probe inserted in a mammalian C-fiber in tissue culture; both before, during and after exposure to the magnetic field generated by the epidural Magna Cath™. This recording clearly shows that the Magna Cath™ reversibly blocks C-fiber firing in vitro.

Figure 45A:
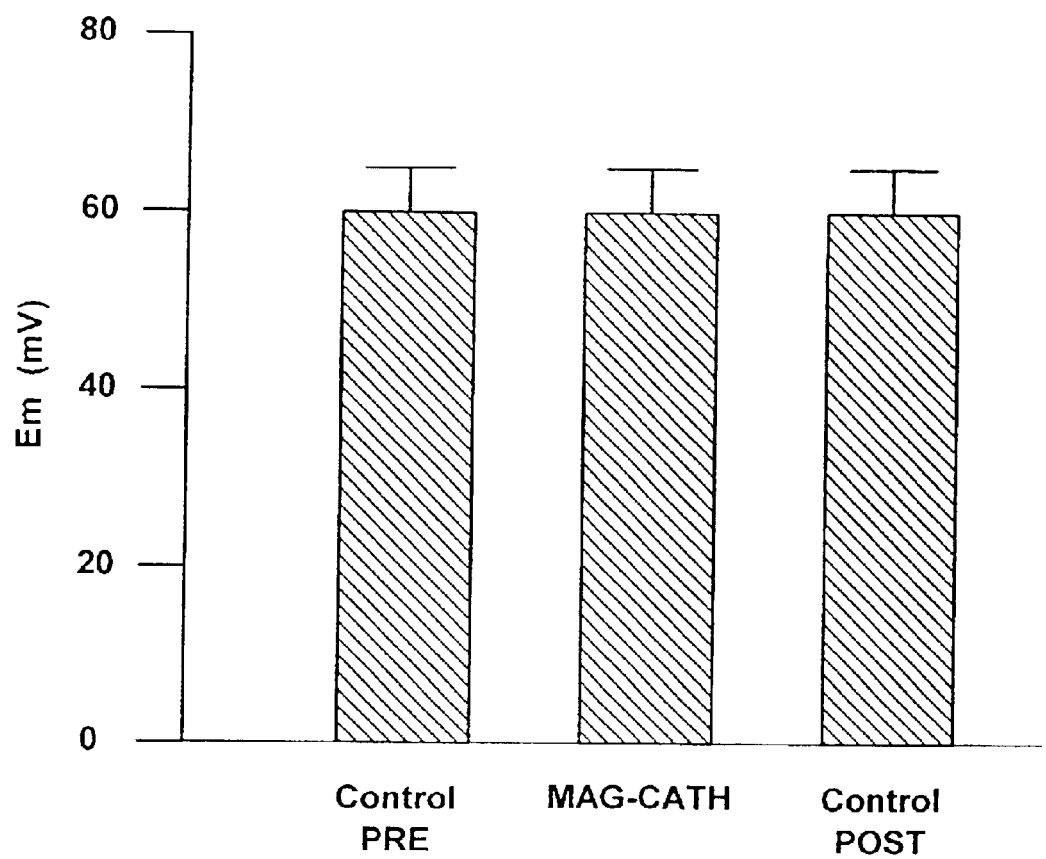

FIG. 45A demonstrates that the Magna Cath™ doesn't alter the electronics.

Figure 45B:
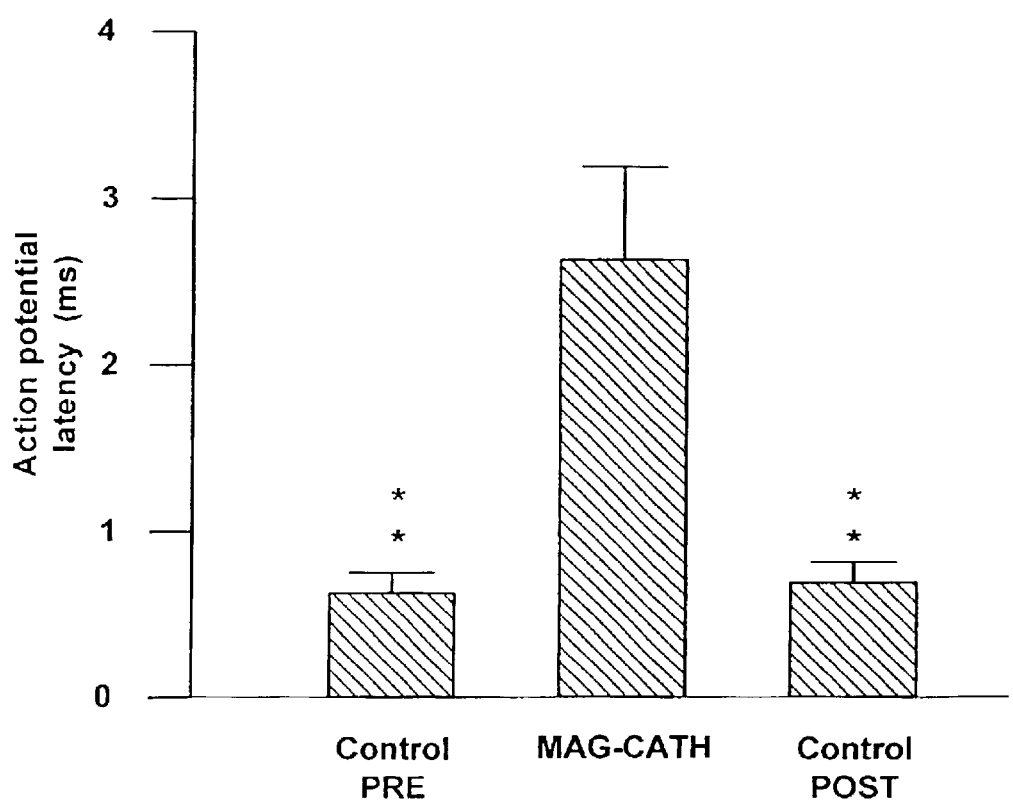

FIG. 45B demonstrates that the Magna Cath™ significantly alters the action potential latency of C-fibers when quantitatively compared to control before and after treatment.

Figure 45C:
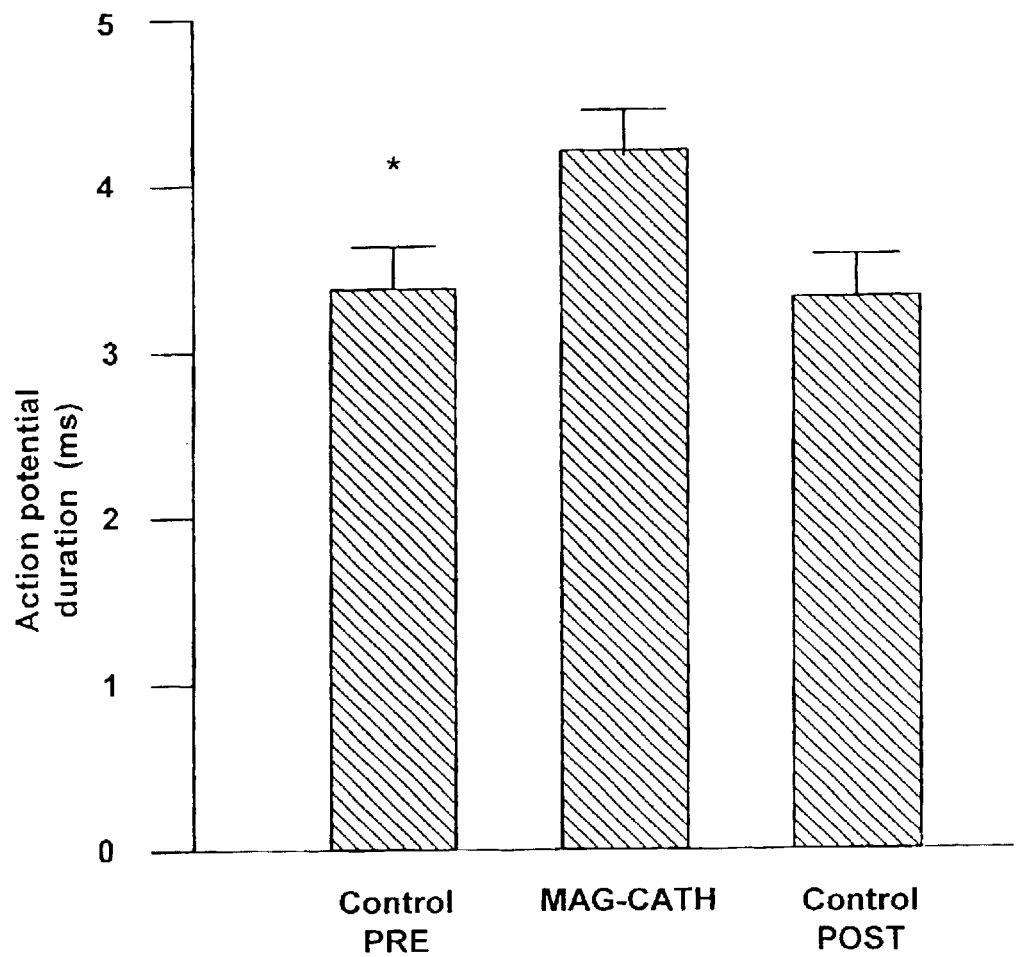

FIG. 45C demonstrates the prolonged action potential duration of C-fibers when exposed to the Magna Cath™.

Figure 45D:
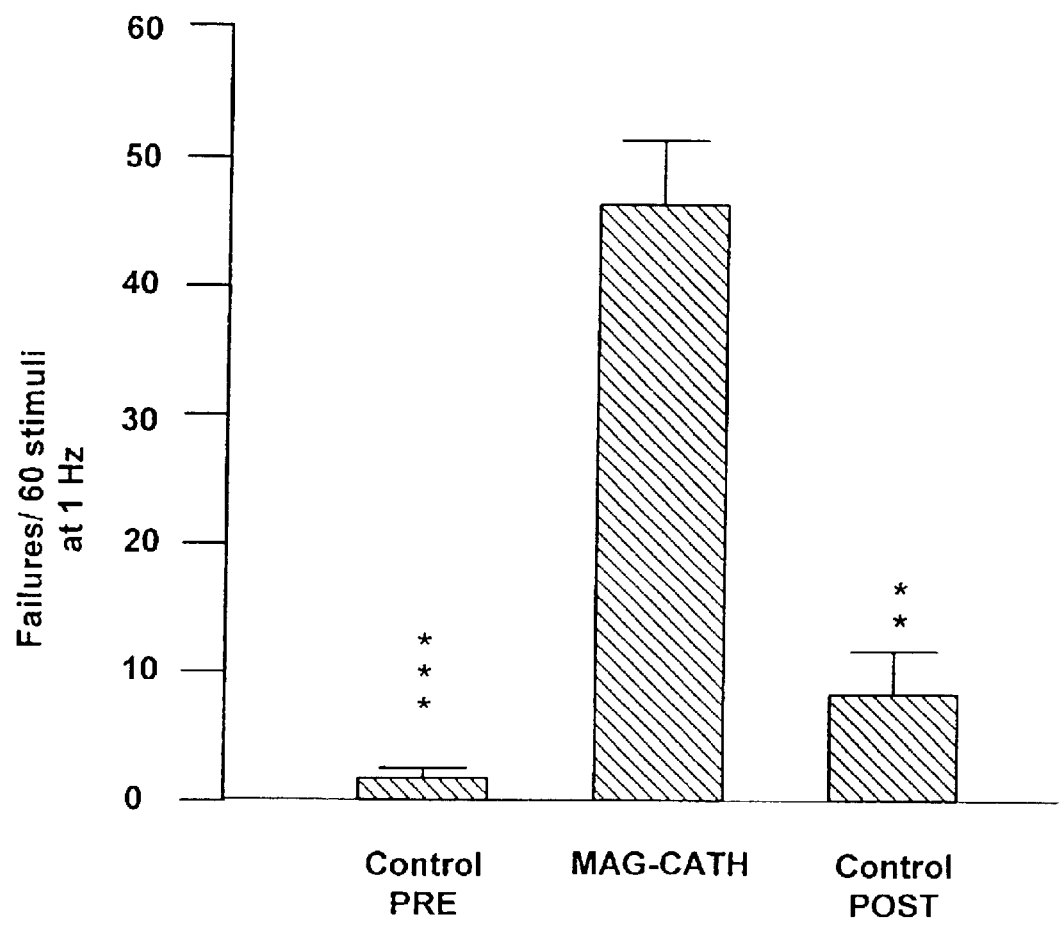

FIG. 45D depicts dramatic failure of action potentials on a quantitative basis when stimulated at 1 Hz and exposed to the Magna Cath™.

Figure 45E:
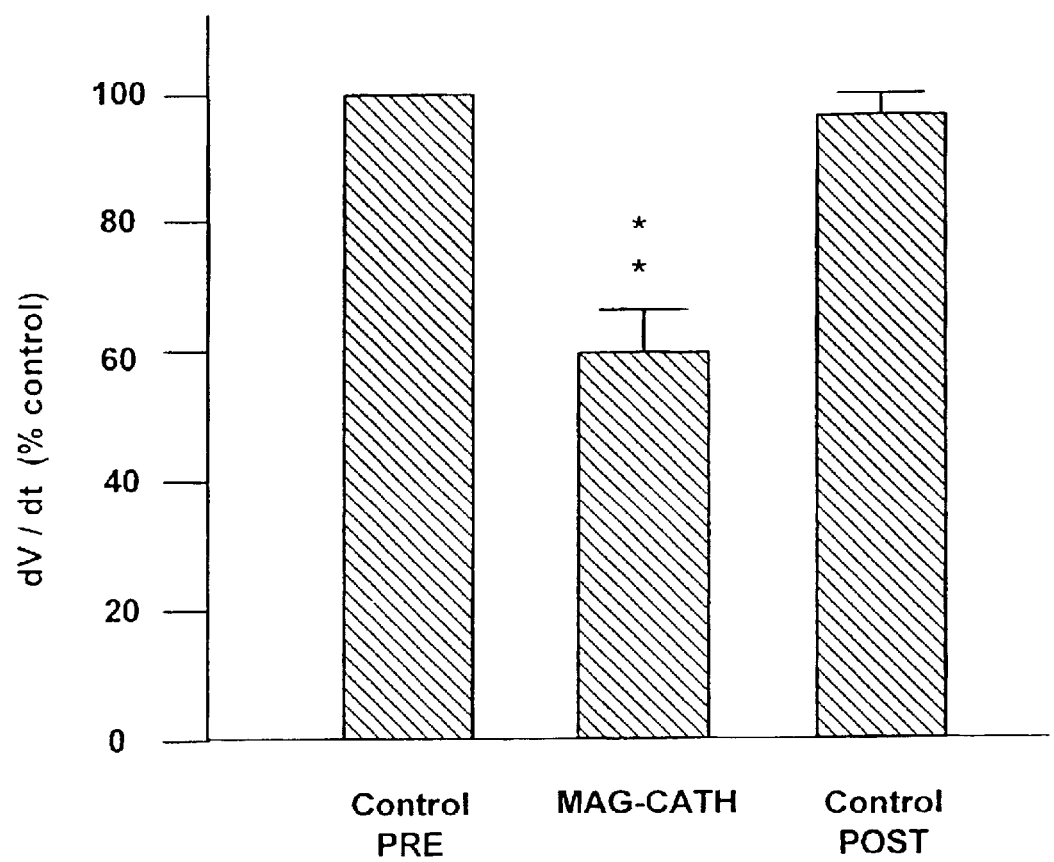

FIG. 45E reveals a significant change in the dv/dt when C-fibers are exposed to the Magna Cath™. This change is related to change in sodium currents.

Figure 45F:
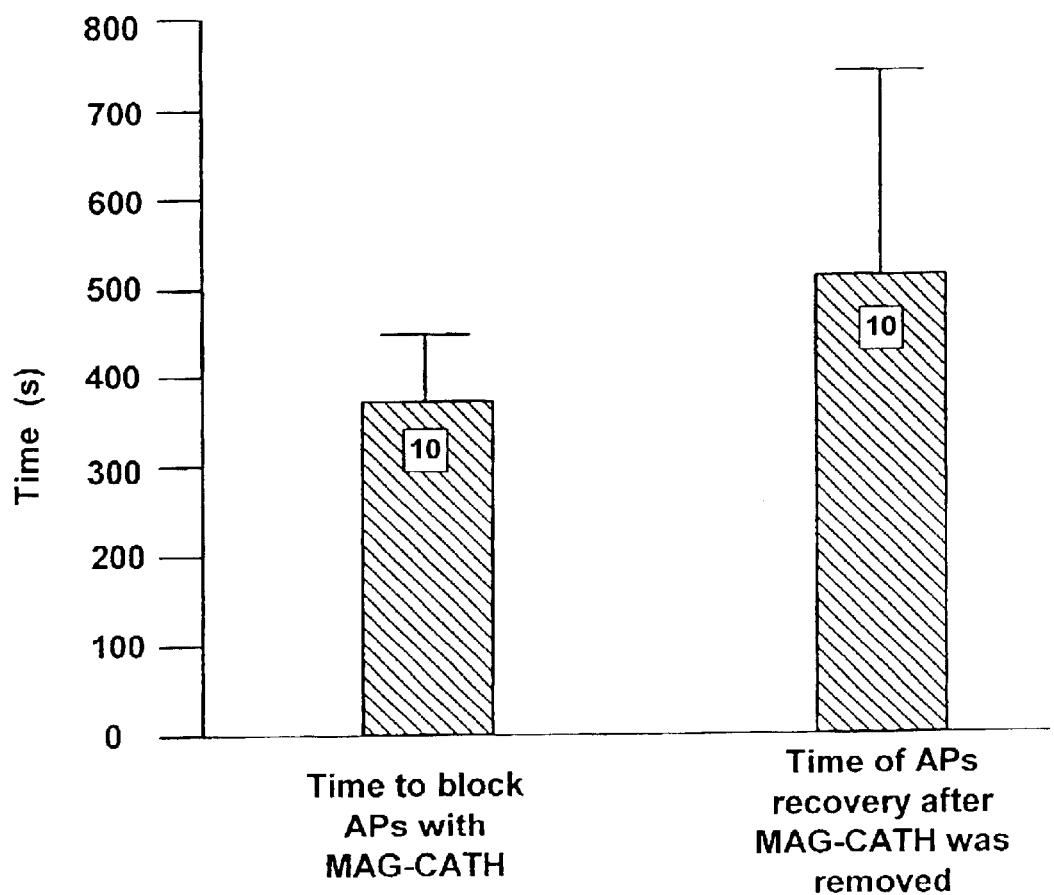

FIG. 45F represents the time required to block and for recovery of C-fiber action potential.

FIG. 46 illustrates a magnetic field around devices and comparison failures between Magna Bloc™ and a 16 array of magnets.

Figure 47:
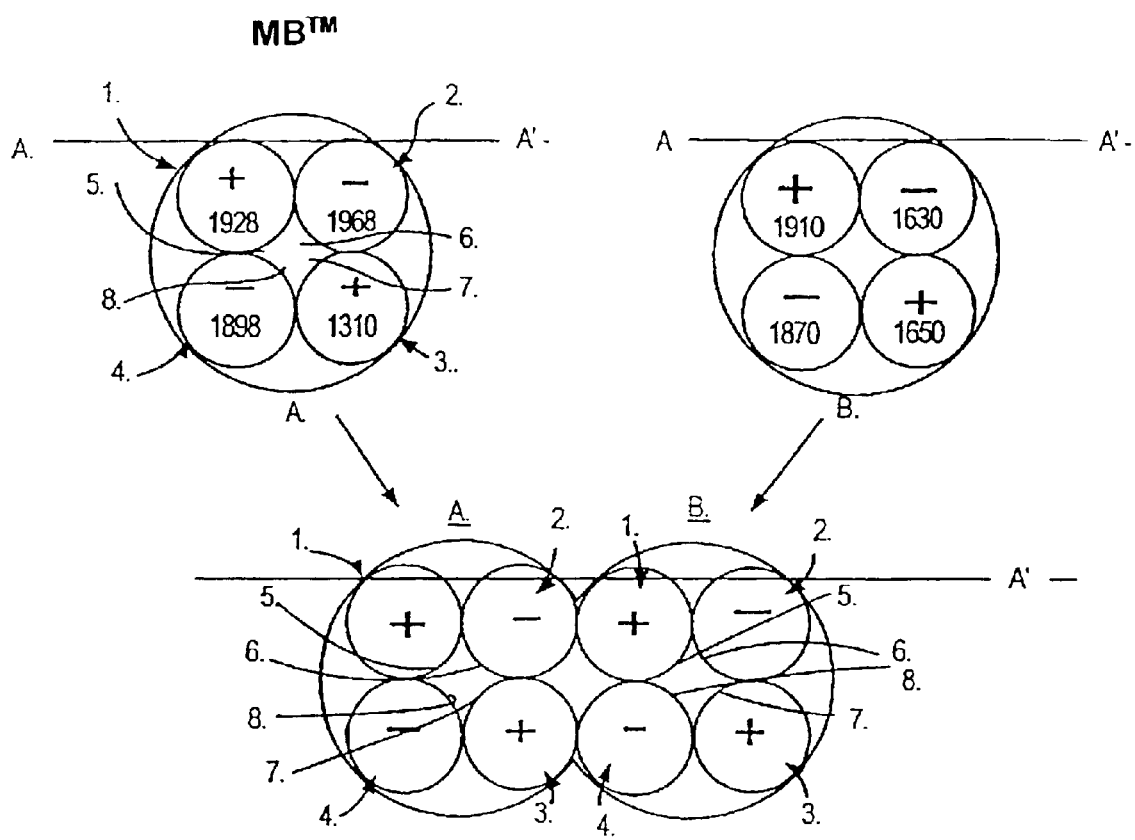

FIG. 47 shows the arrangement of two magnetic devices and the measurement of their magnetic field.

Figure 48:
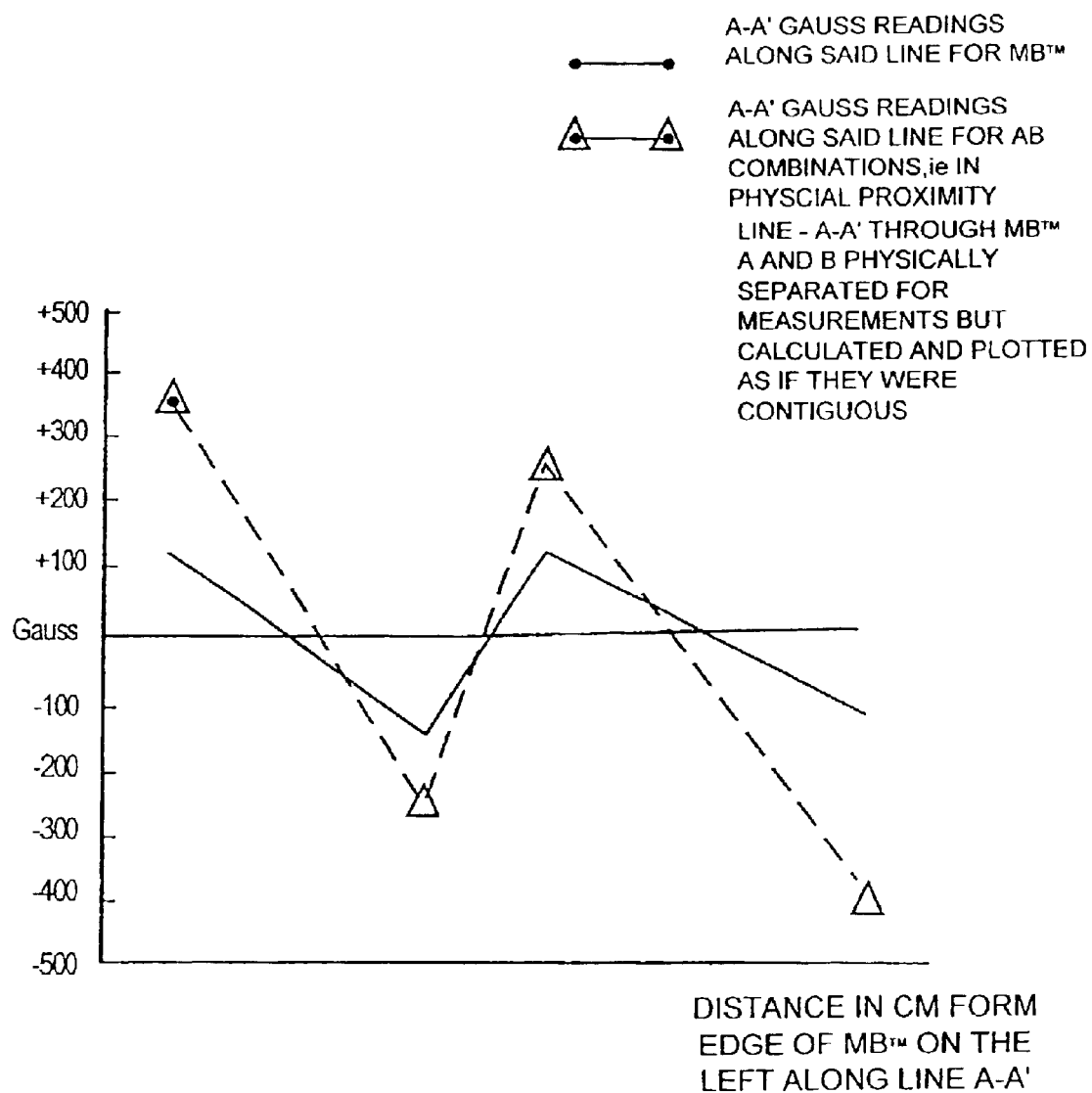

FIG. 48 is a graph showing the magnetic field for devices of FIG. 47.

FIG. 49 illustrates the field around the device and a two magnet device, and shows comparative neurons firing data for the two devices.

Figure 50:
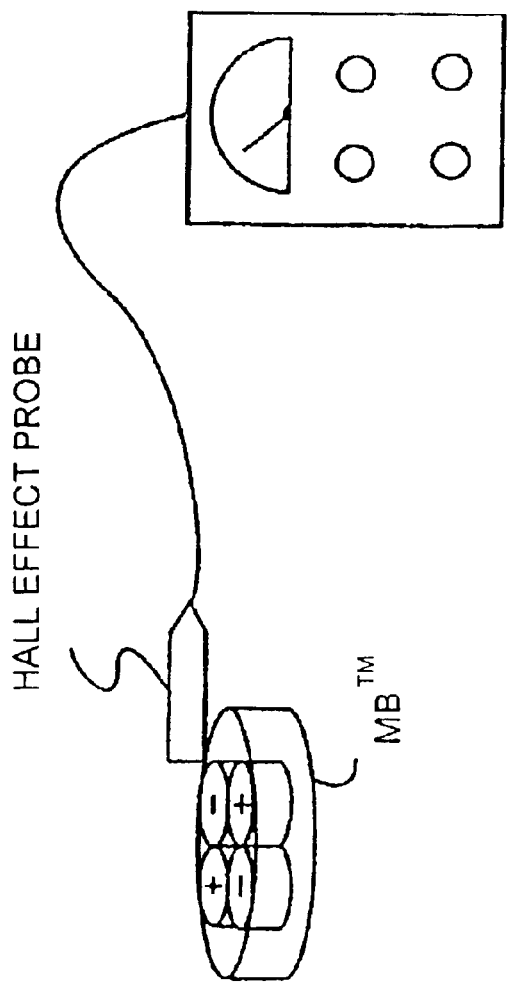

FIG. 50 schematically illustrates the apparatus used to measure the magnetic field data in FIGS. 47 and 48.

Figure 51:
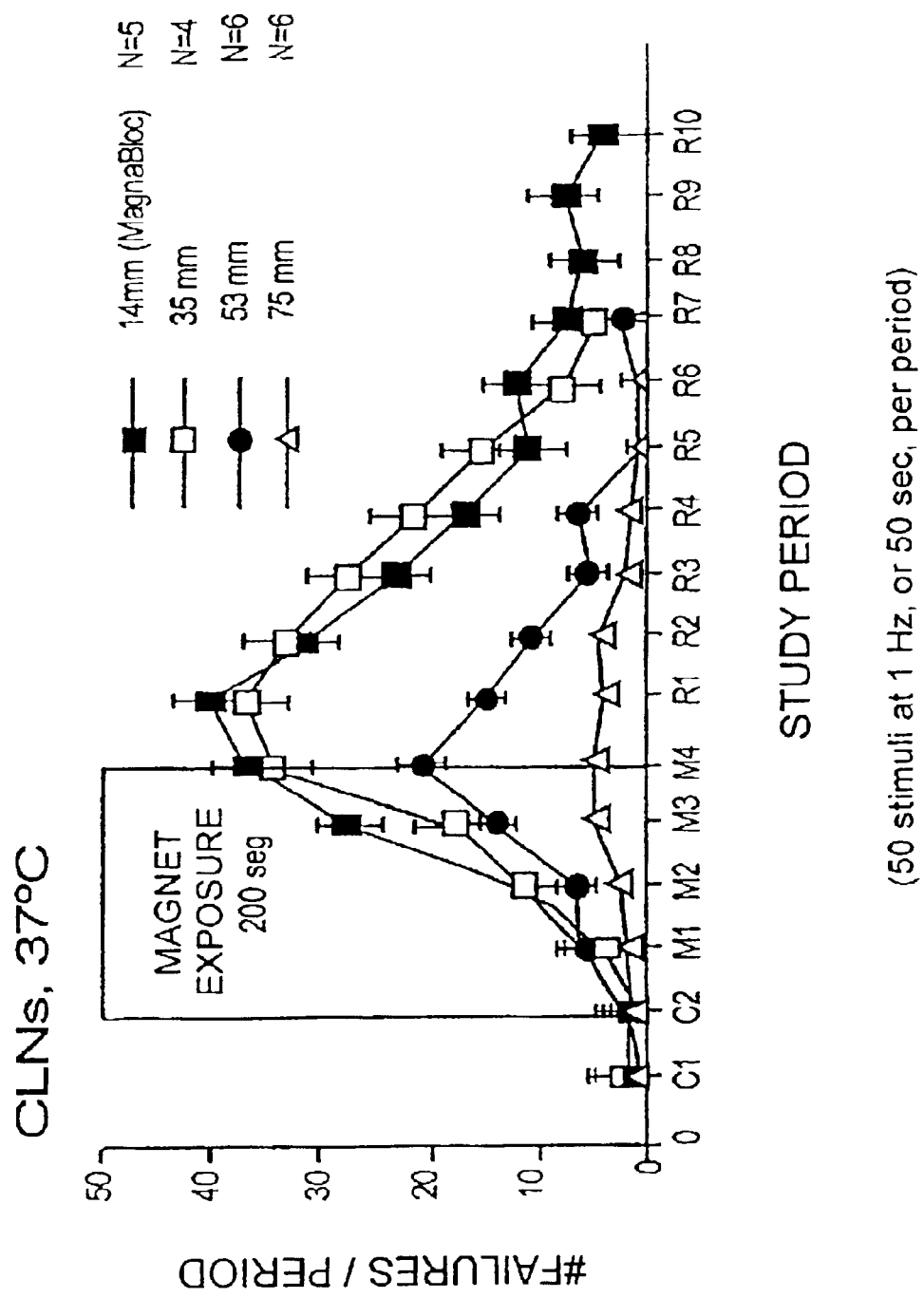

FIG. 51 is a graph comparing the average number of times neurons failed to elicit action potentials in response to applied stimuli before, during and after exposure to the magnetic device of FIG. 23 and to similar magnetic devices in which the magnets were spaced from each other at various distances.

Figure 52:
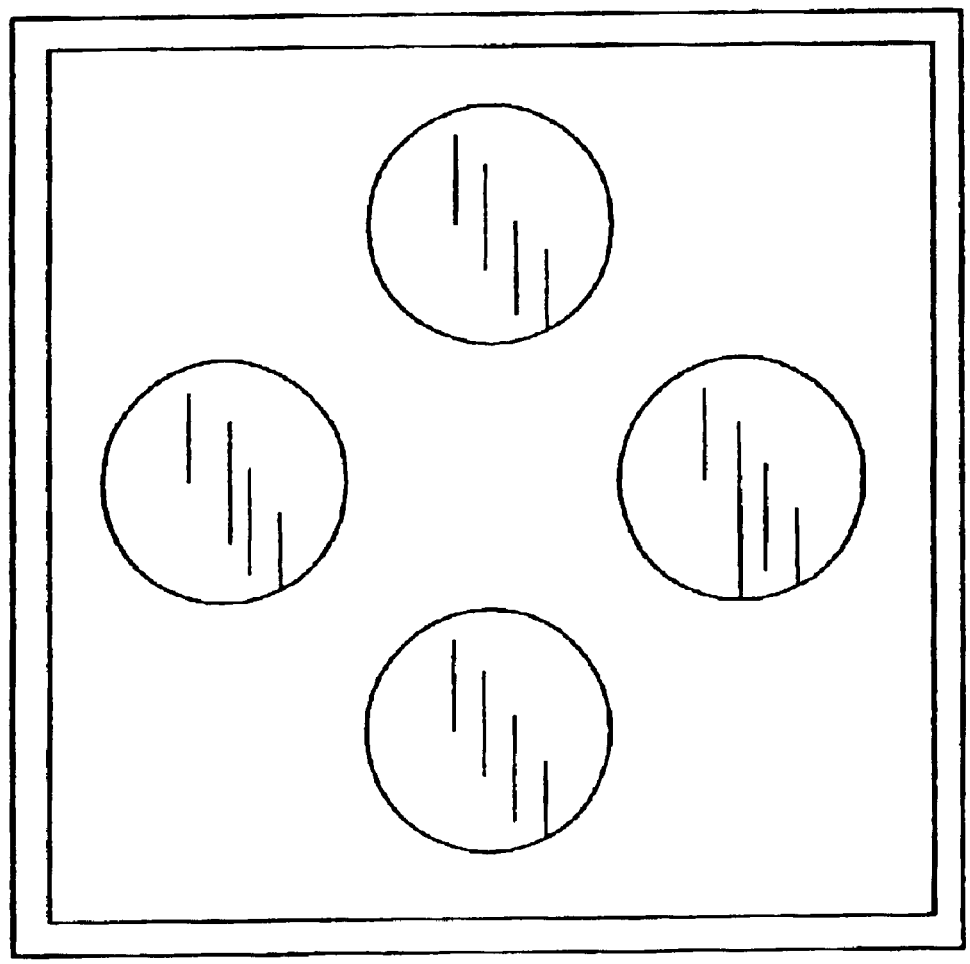
Figure 53:
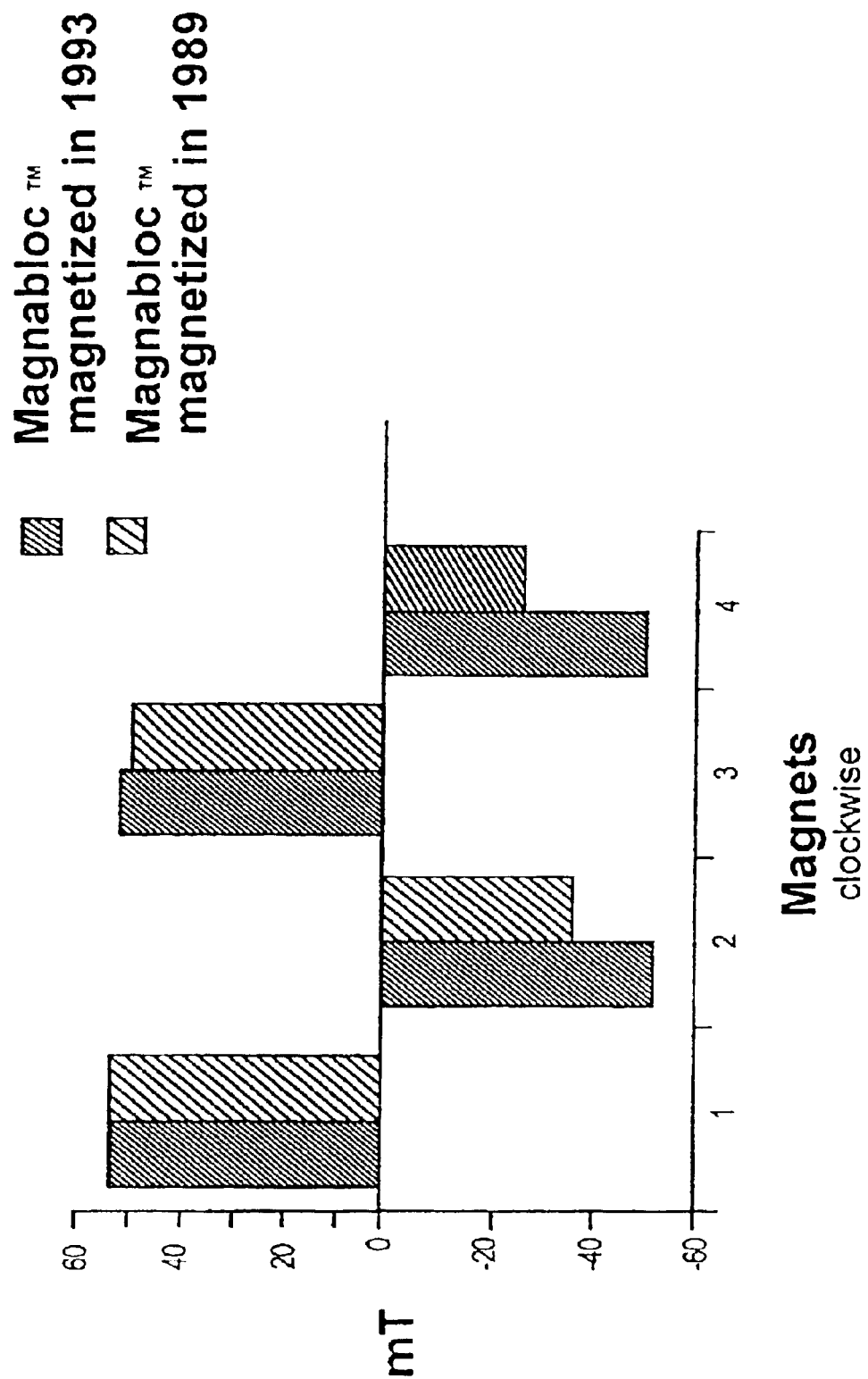
Figure 54:
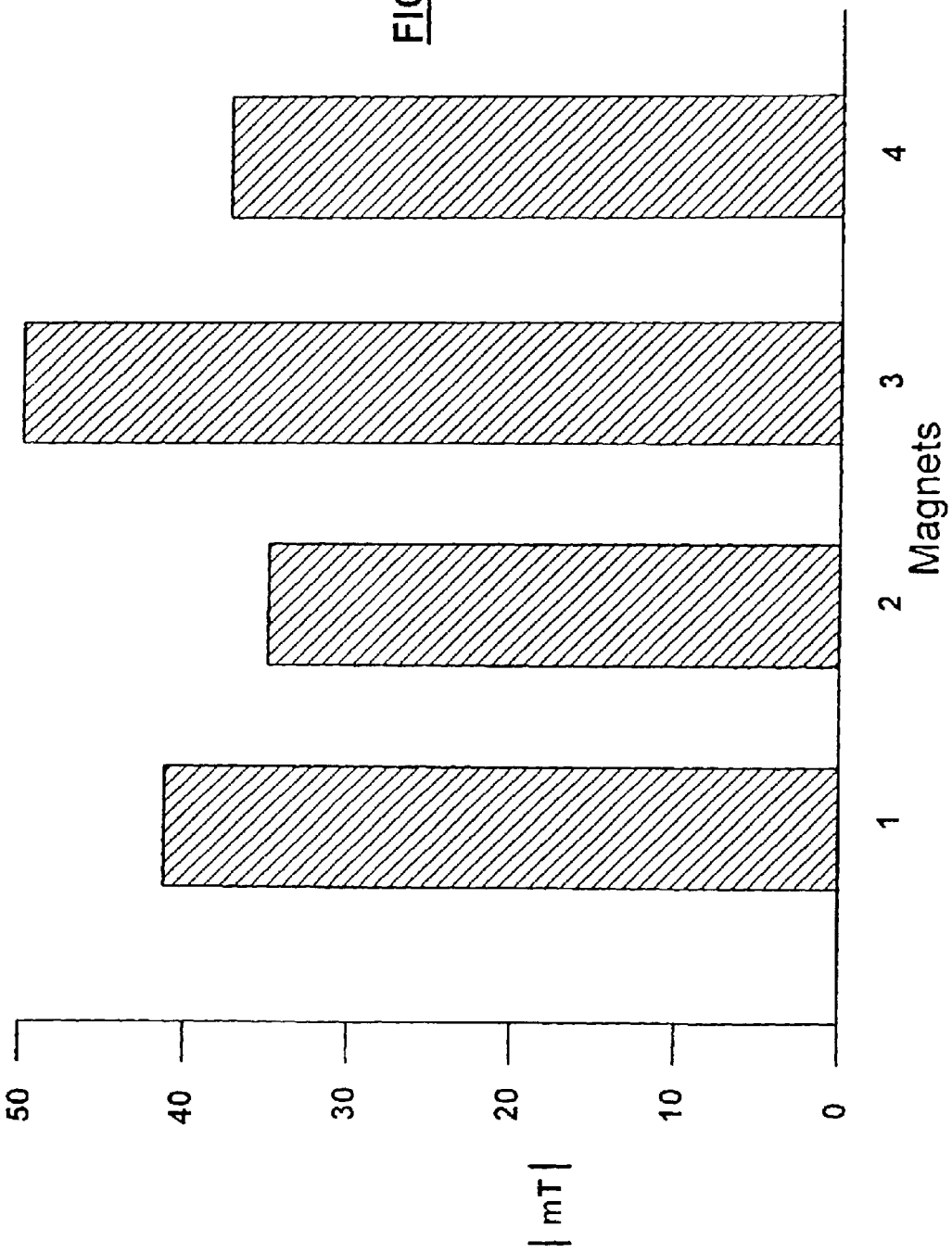
Figure 55:
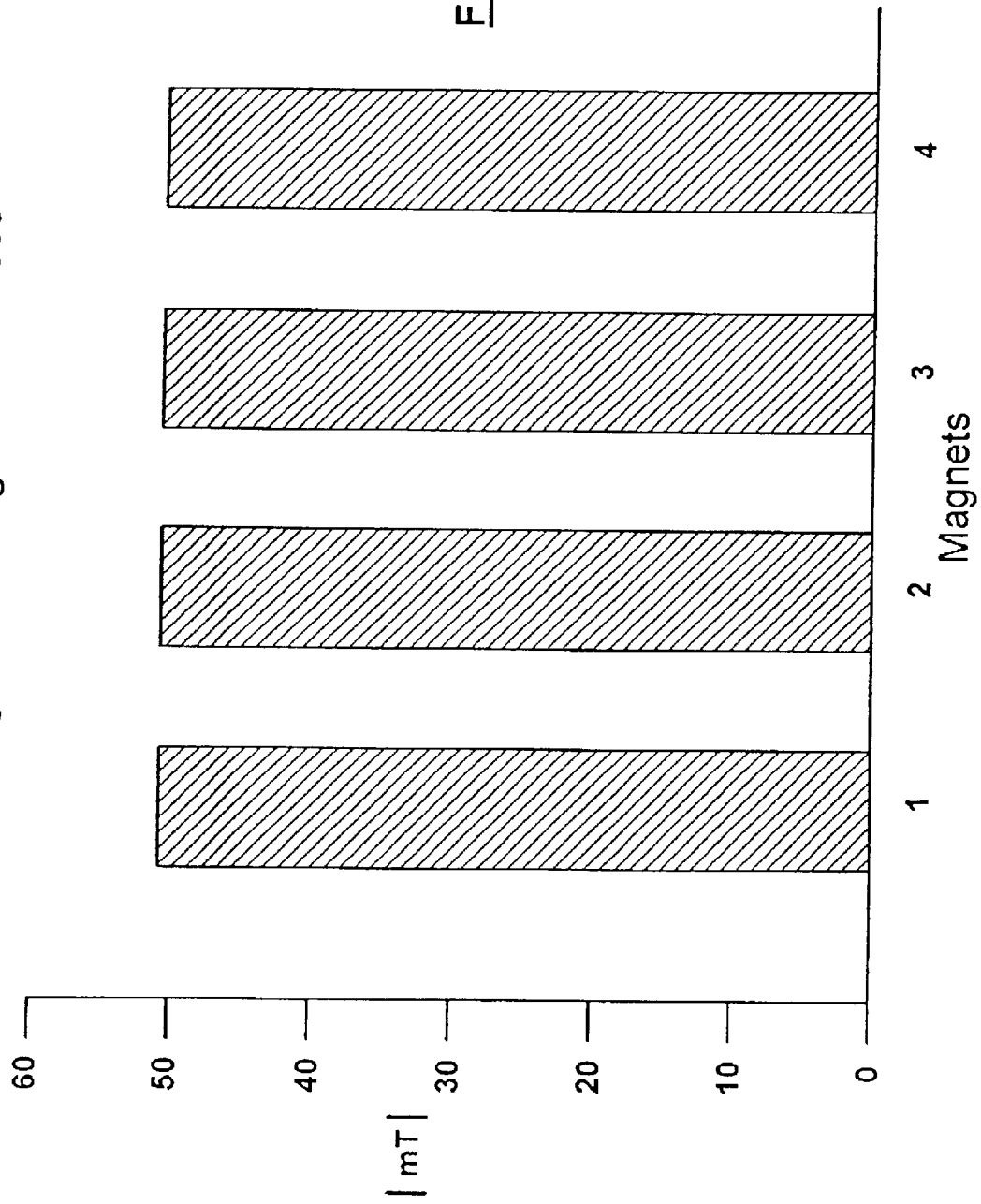
Figure 56:
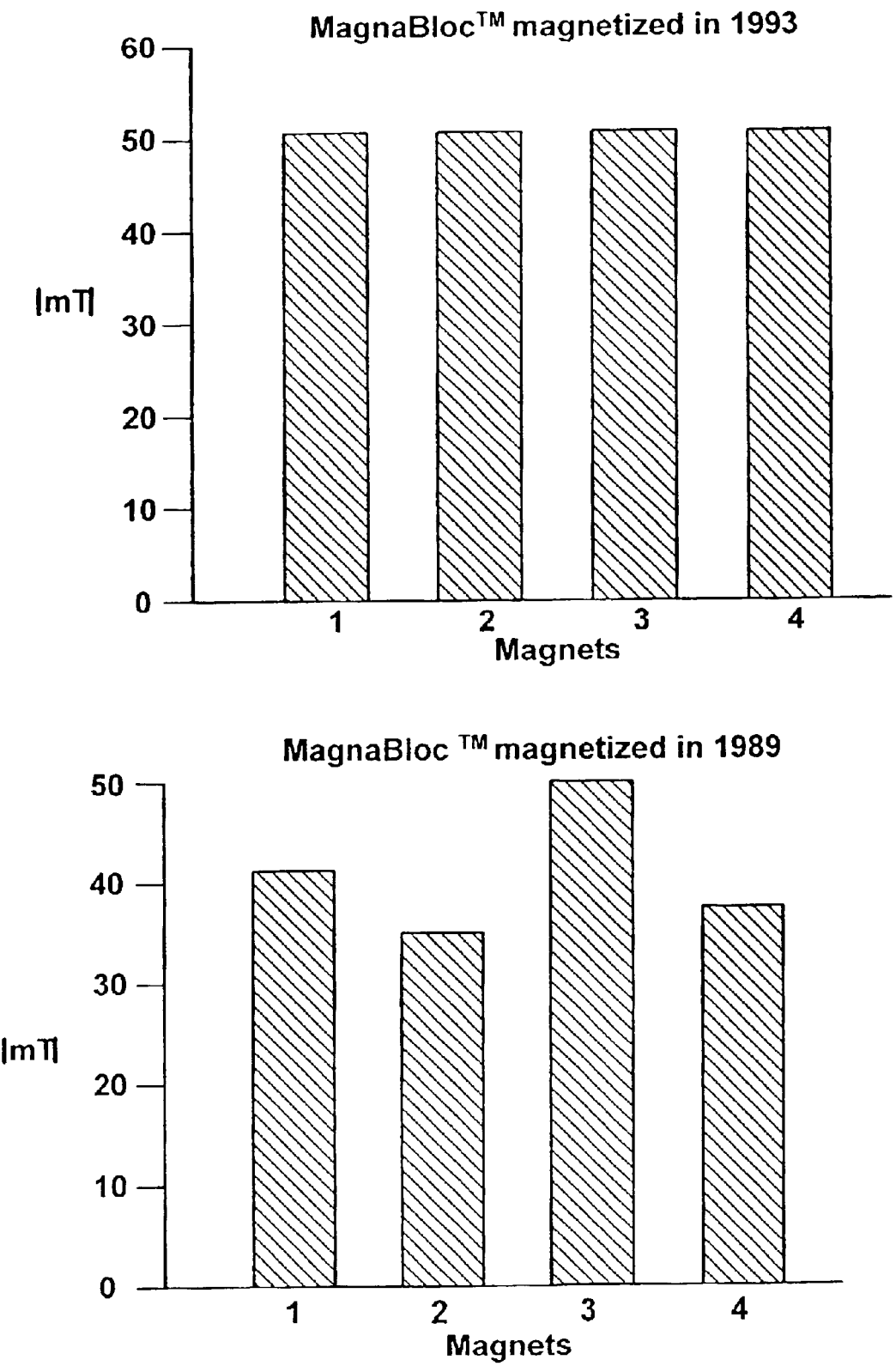

FIG. 52 shows a test fixture in which the magnets were held during the testing for which the data are shown in FIG. 51.

FIGS. 53–56 are illustrations and graphs demonstrating the difference in pole strengths and a comparison of their effectiveness on blocking C-fibers.

Figure 57:
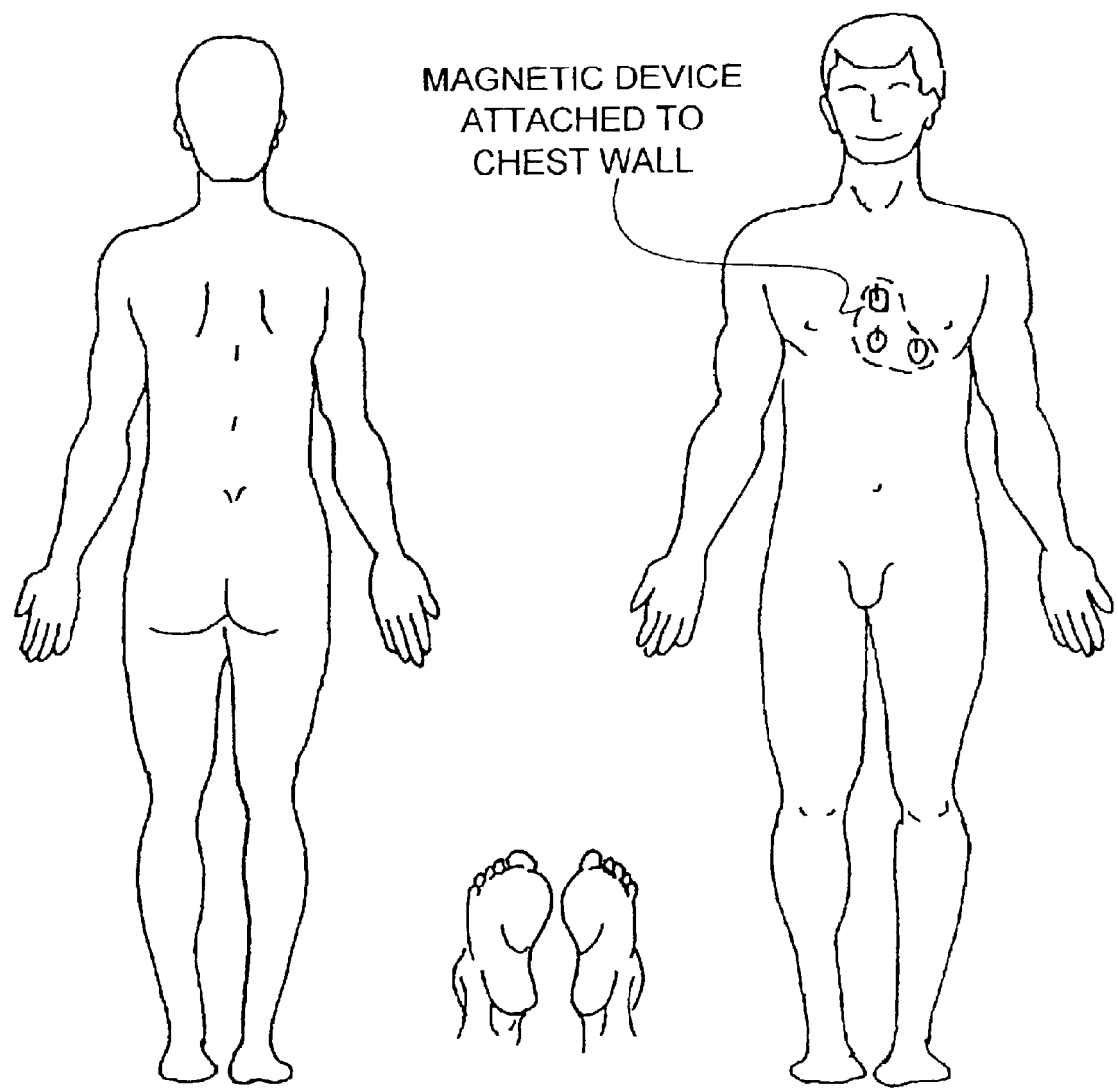
Figure 58:
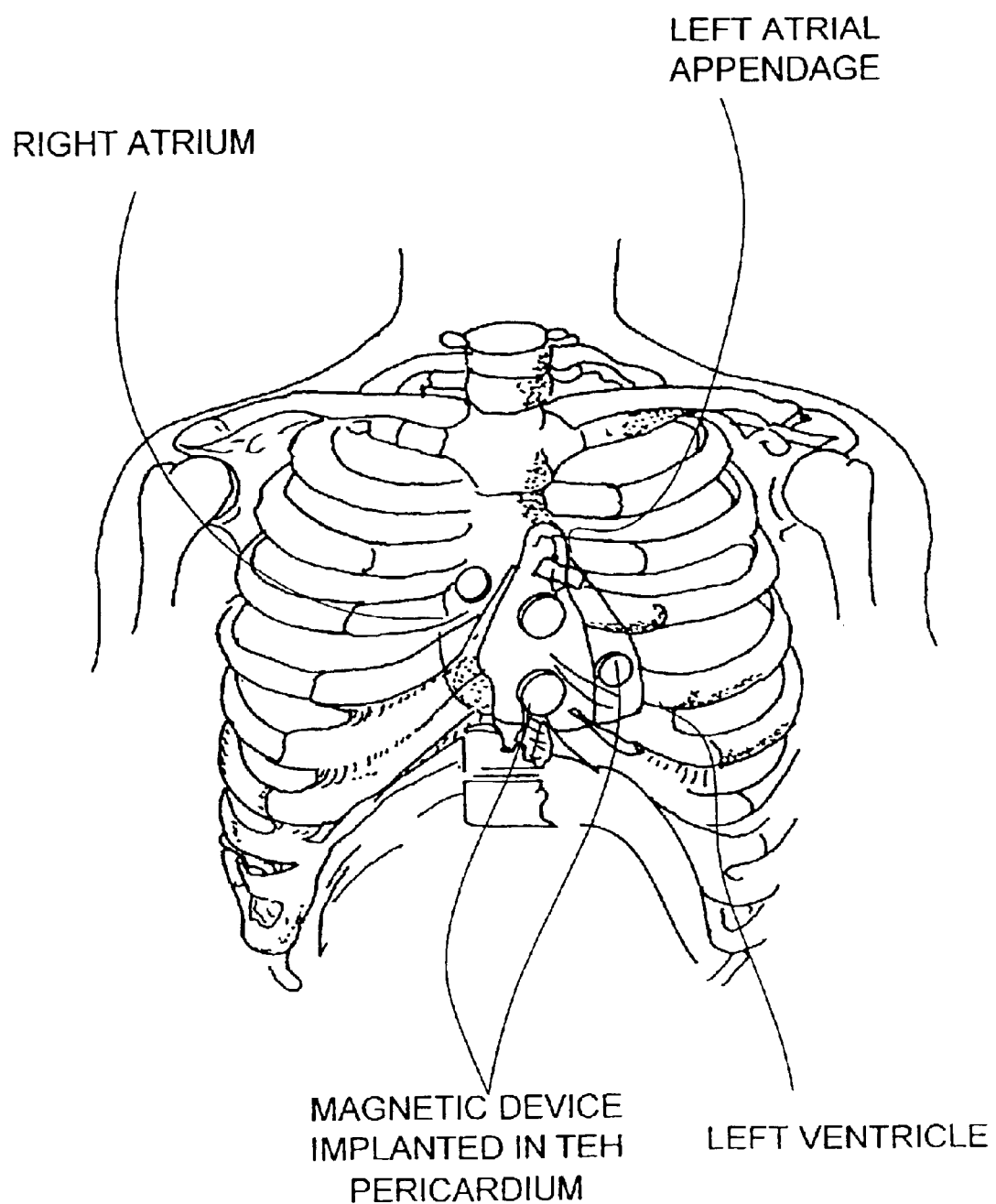
Figure 59:
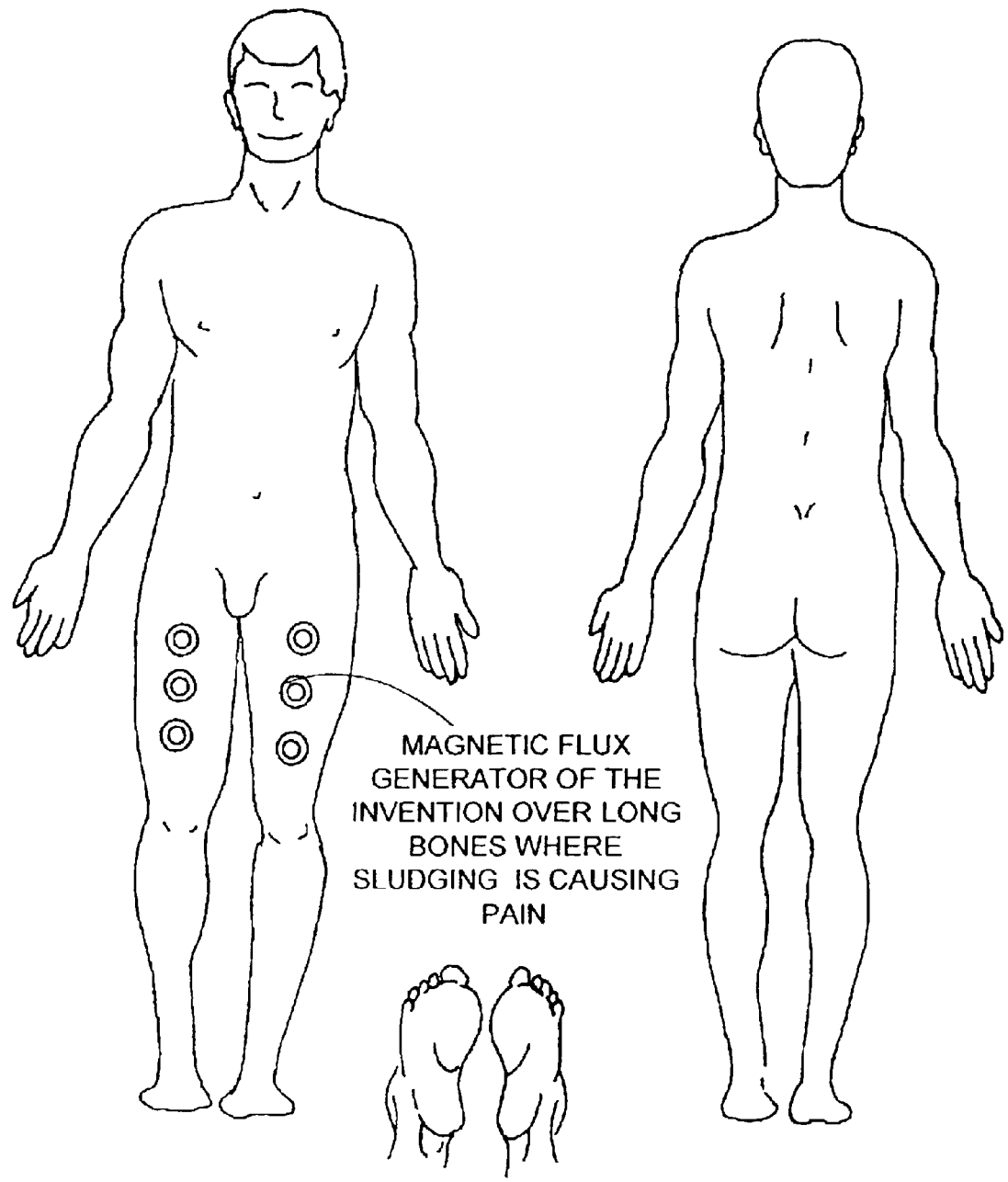
Figure 60:
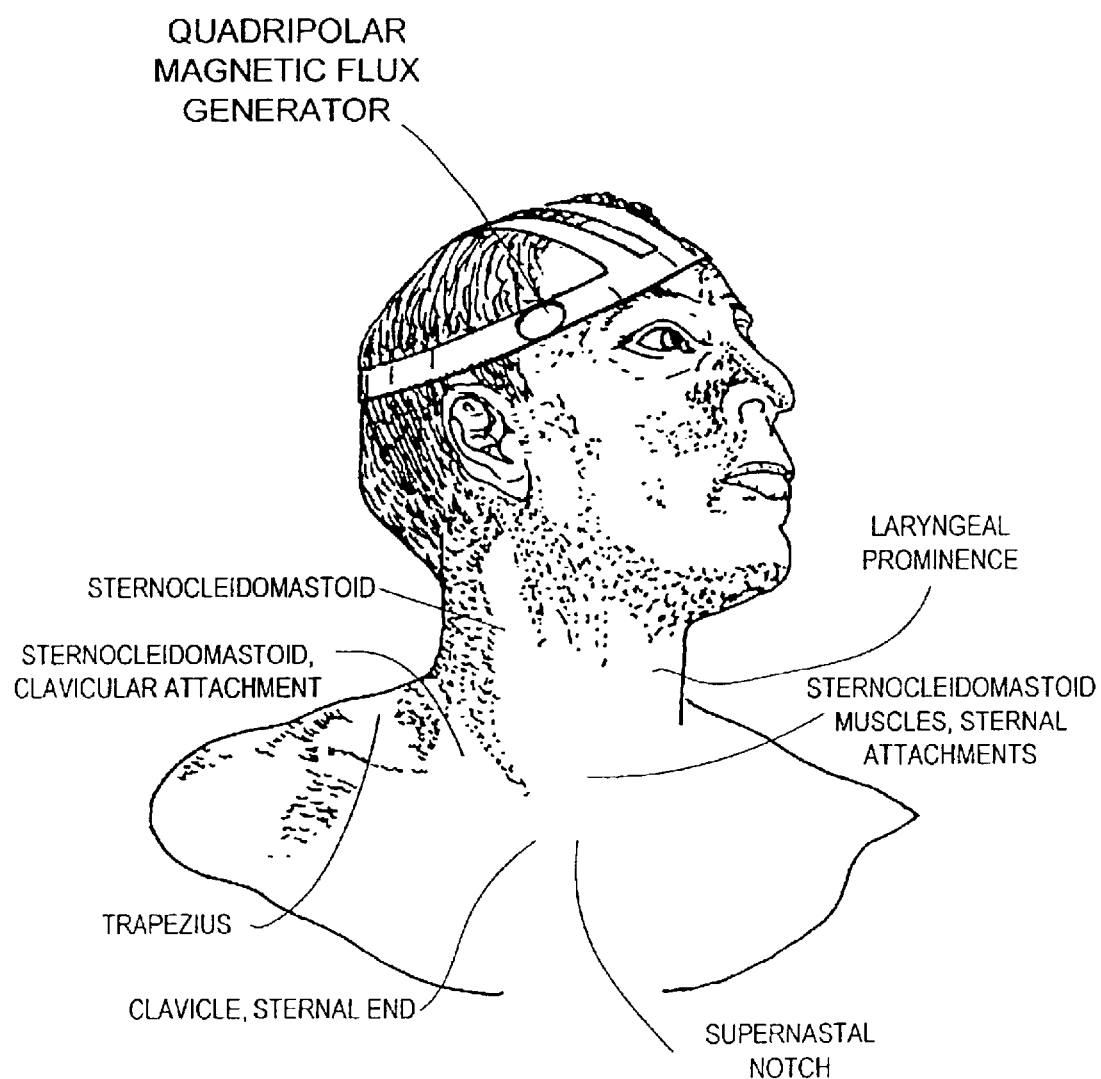
Figure 61A:
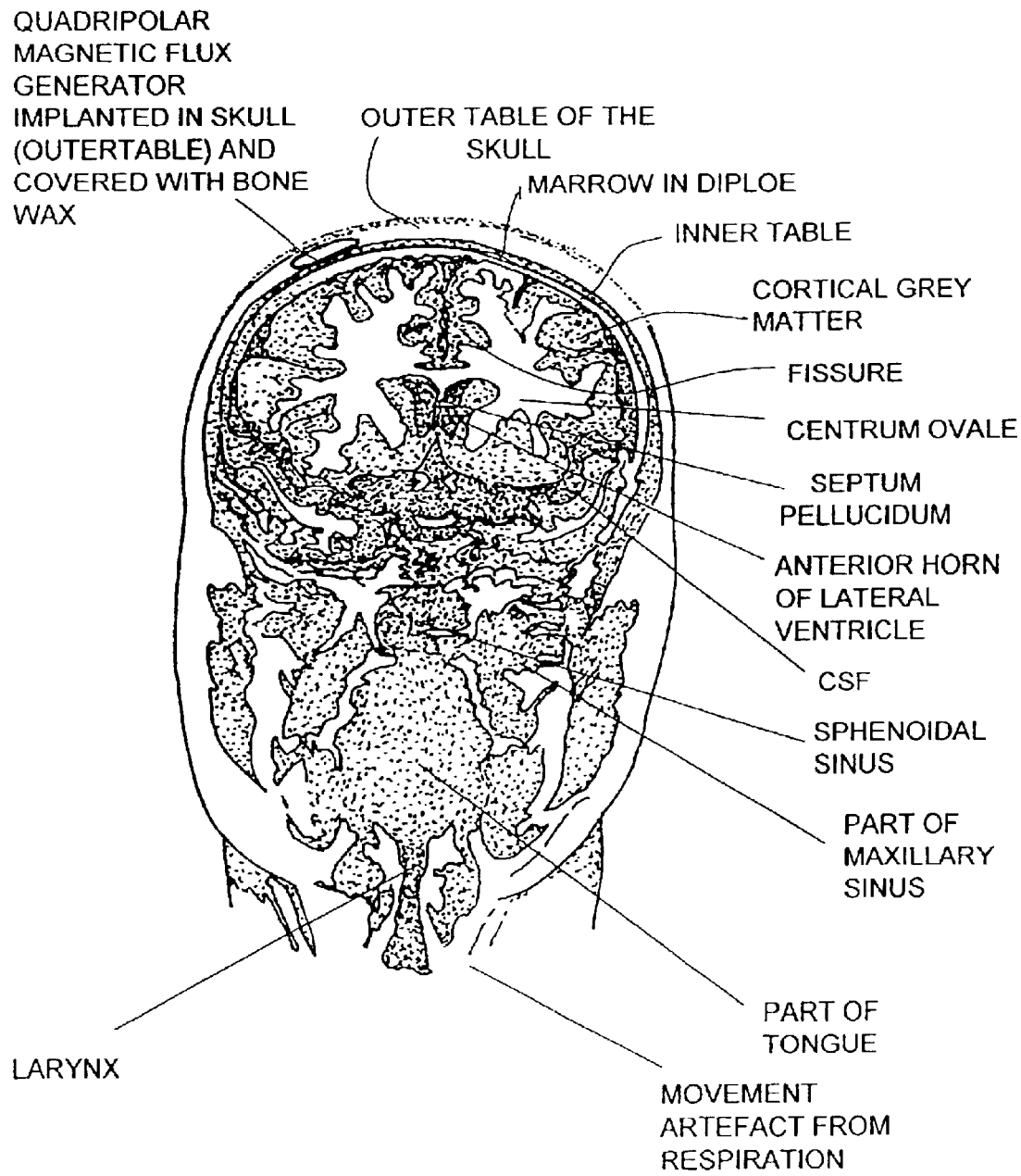
Figure 61B:
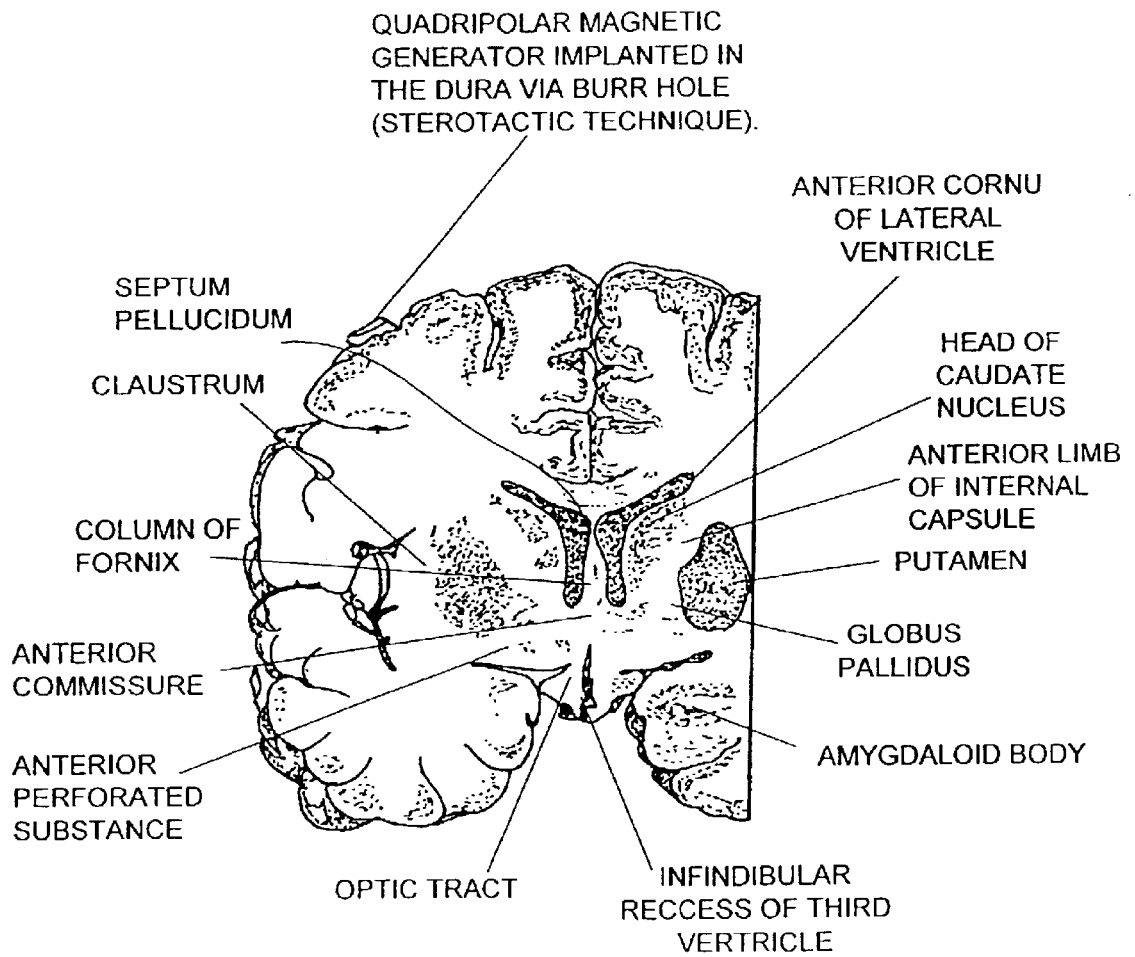
Figure 62A:
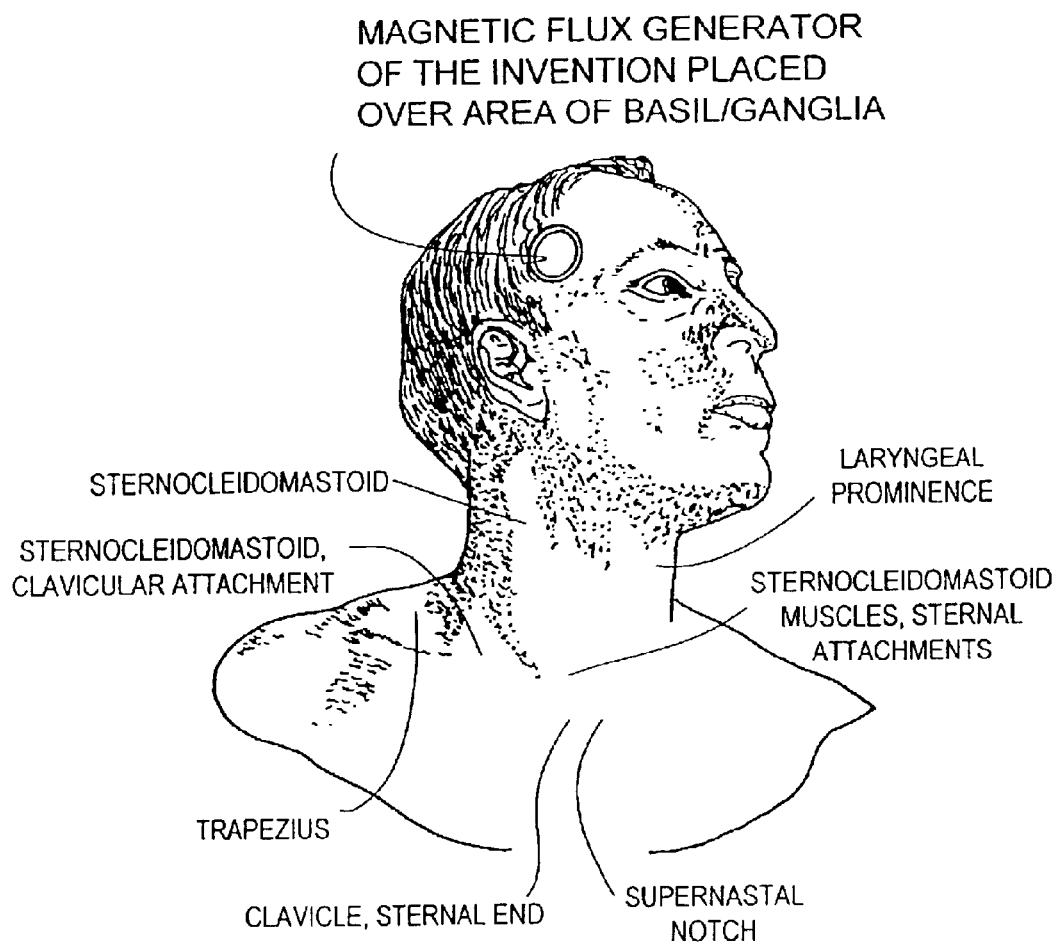
Figure 62B:
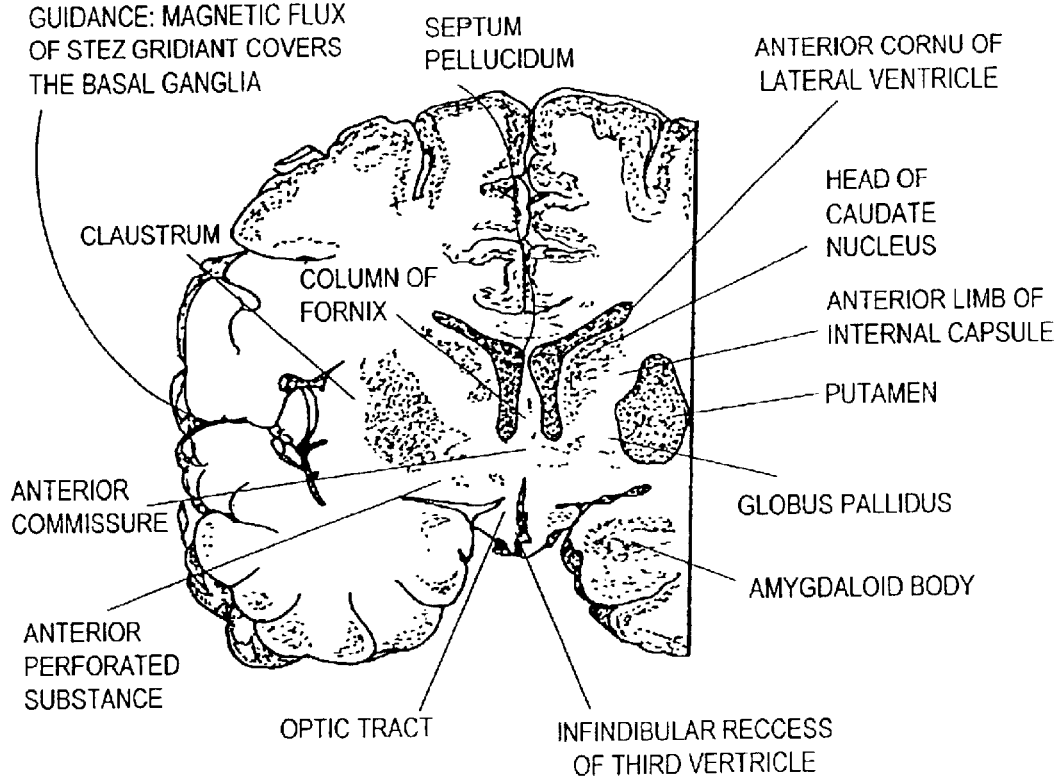
Figure 63:
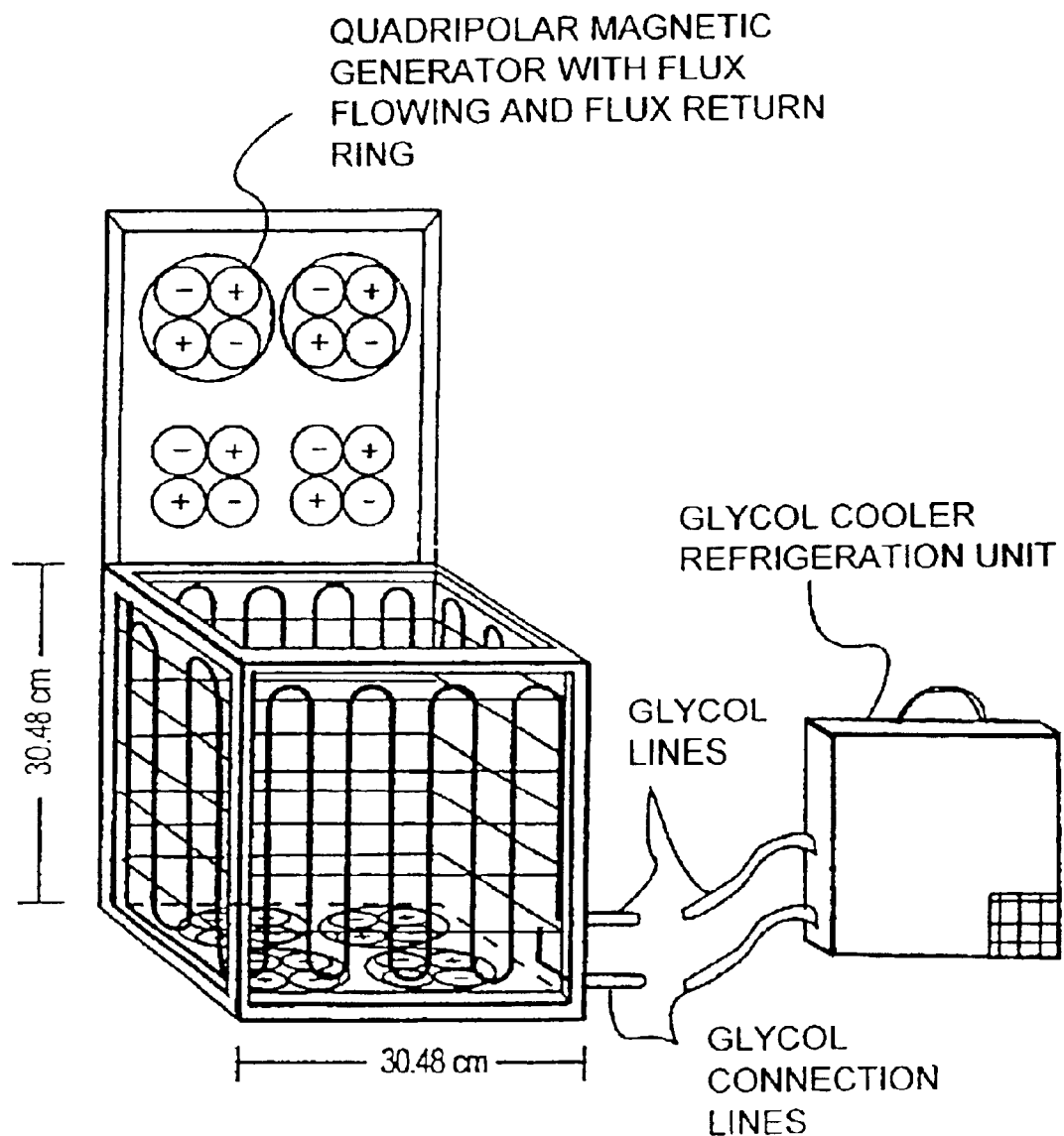
Figure 68:
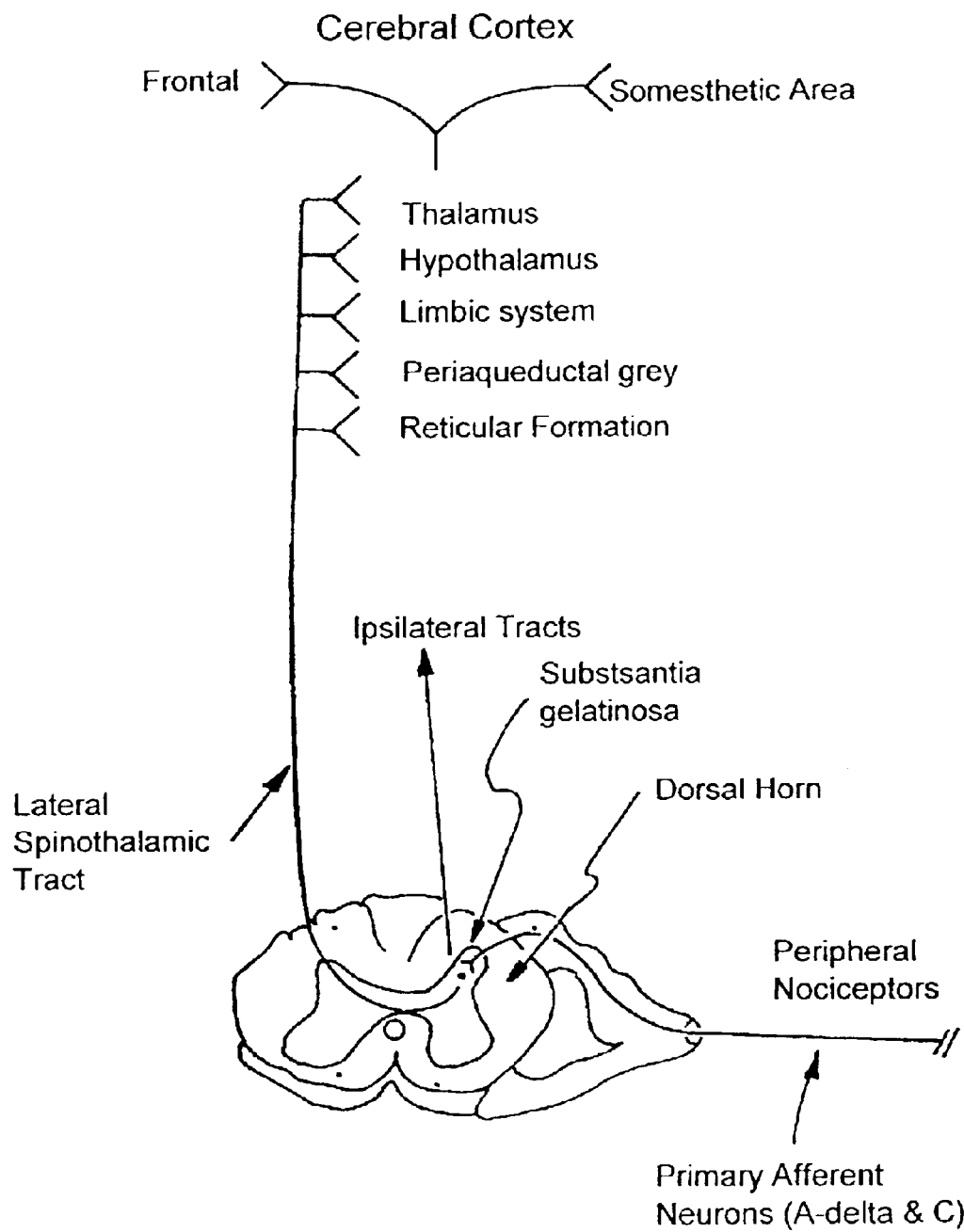
Figure 69:
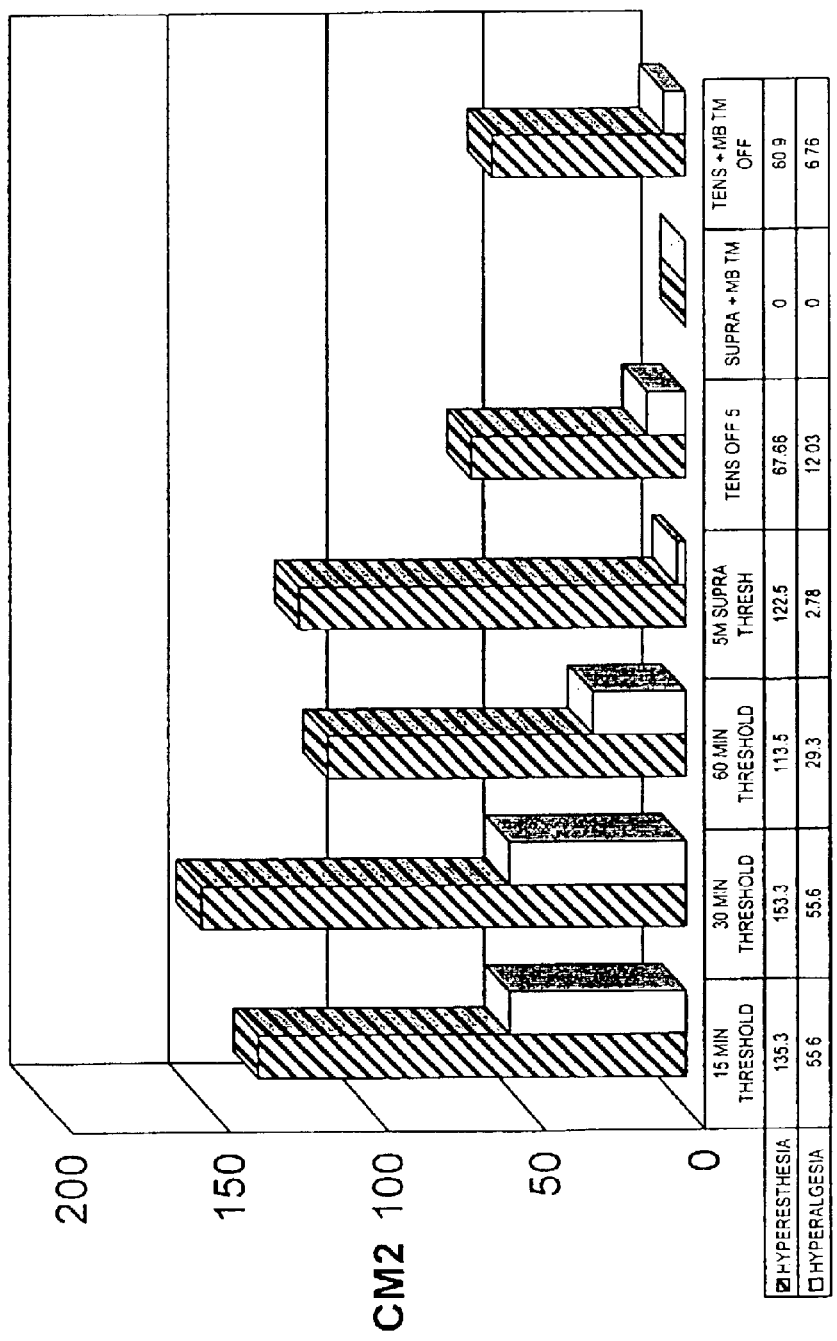
Figure 70:
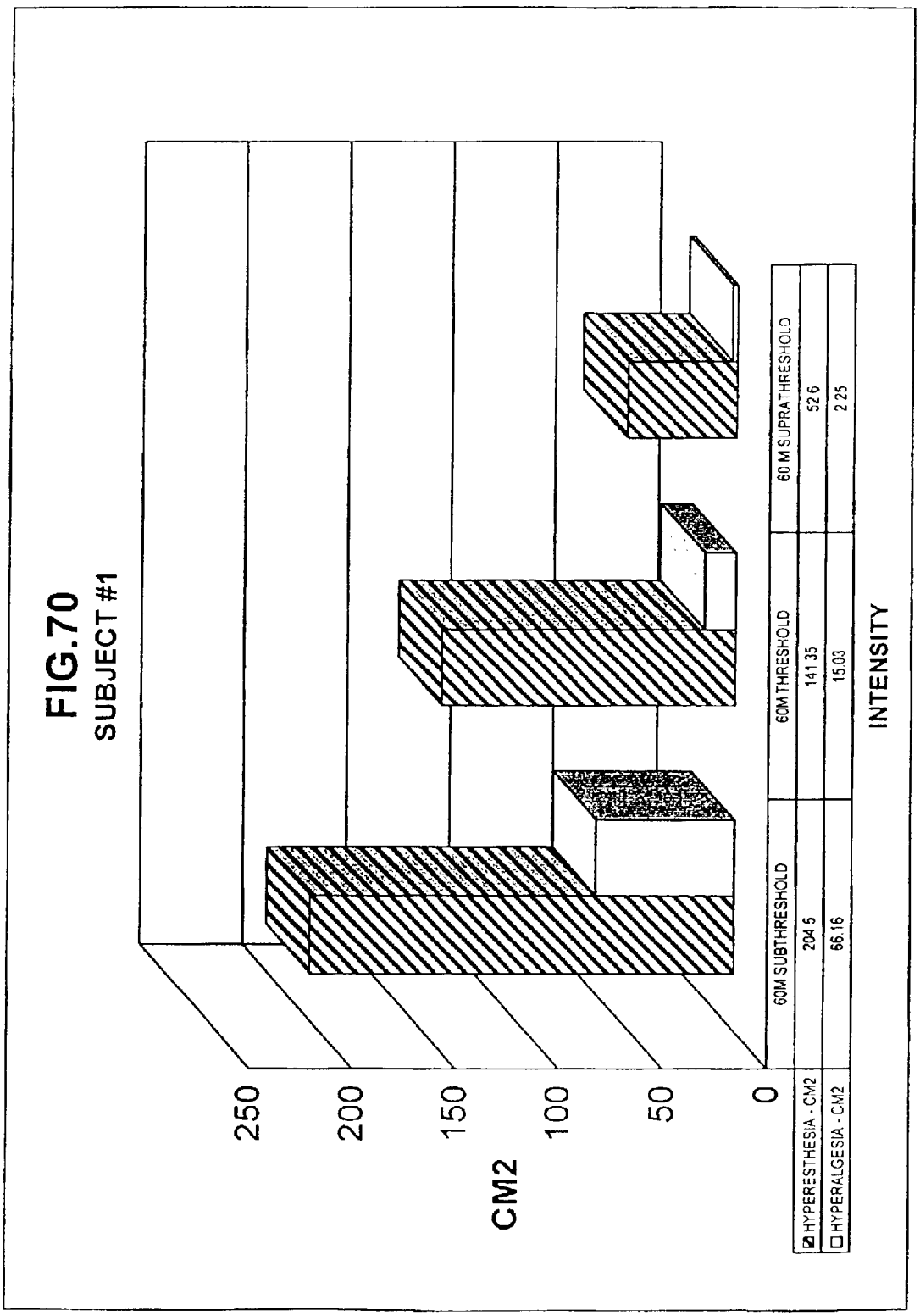
Figure 71:
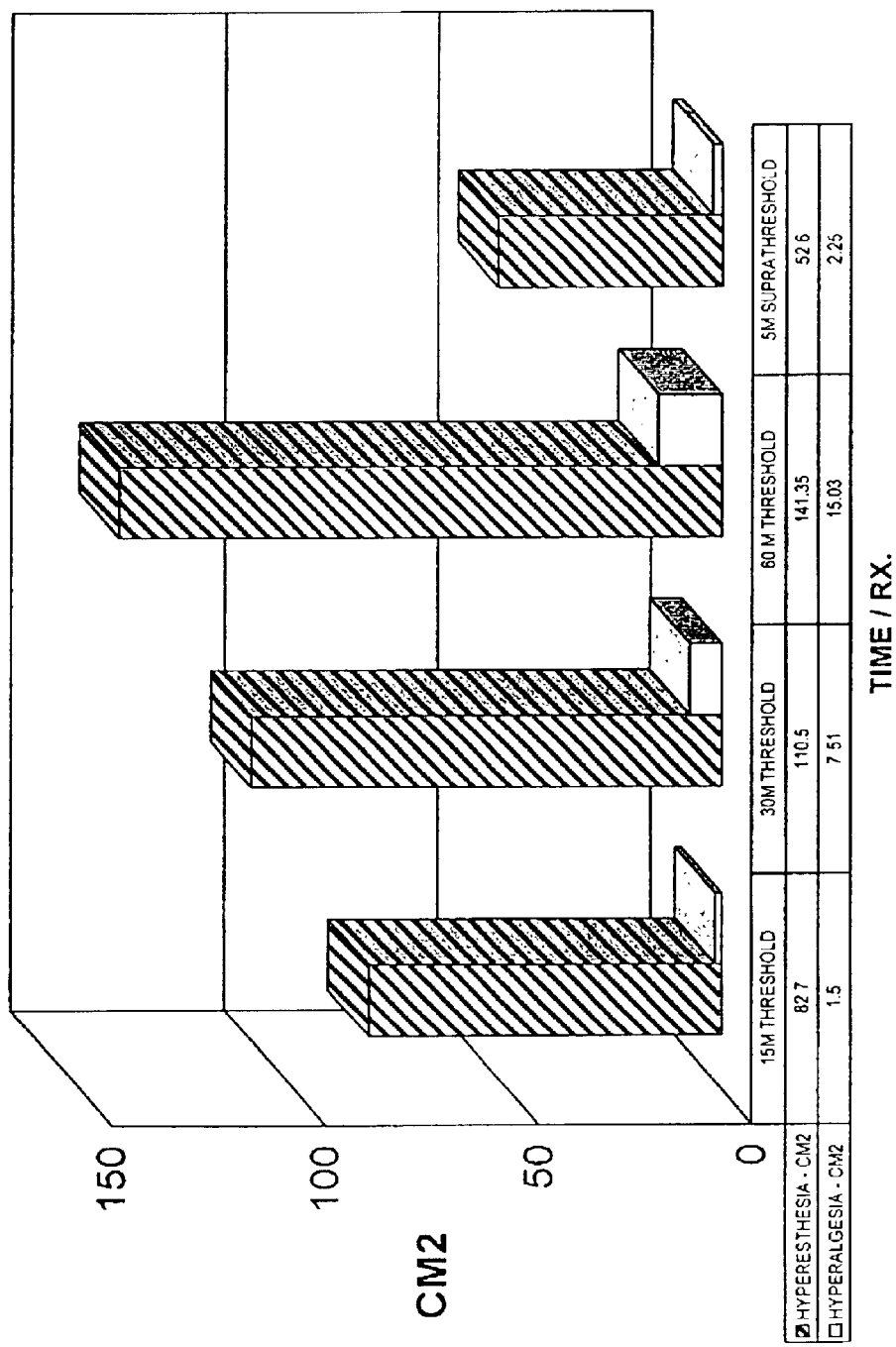
Figure 72:
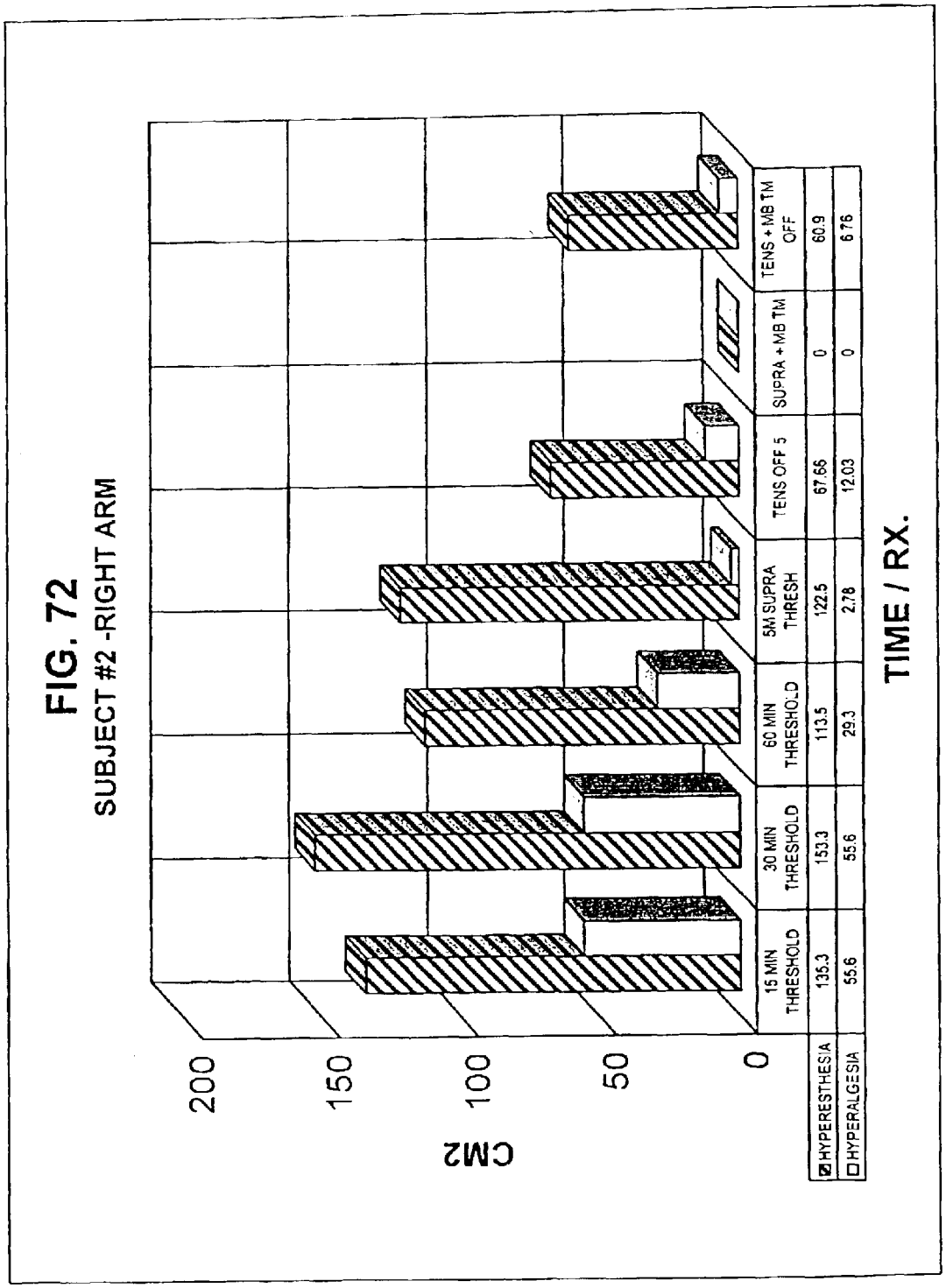
Figure 73:
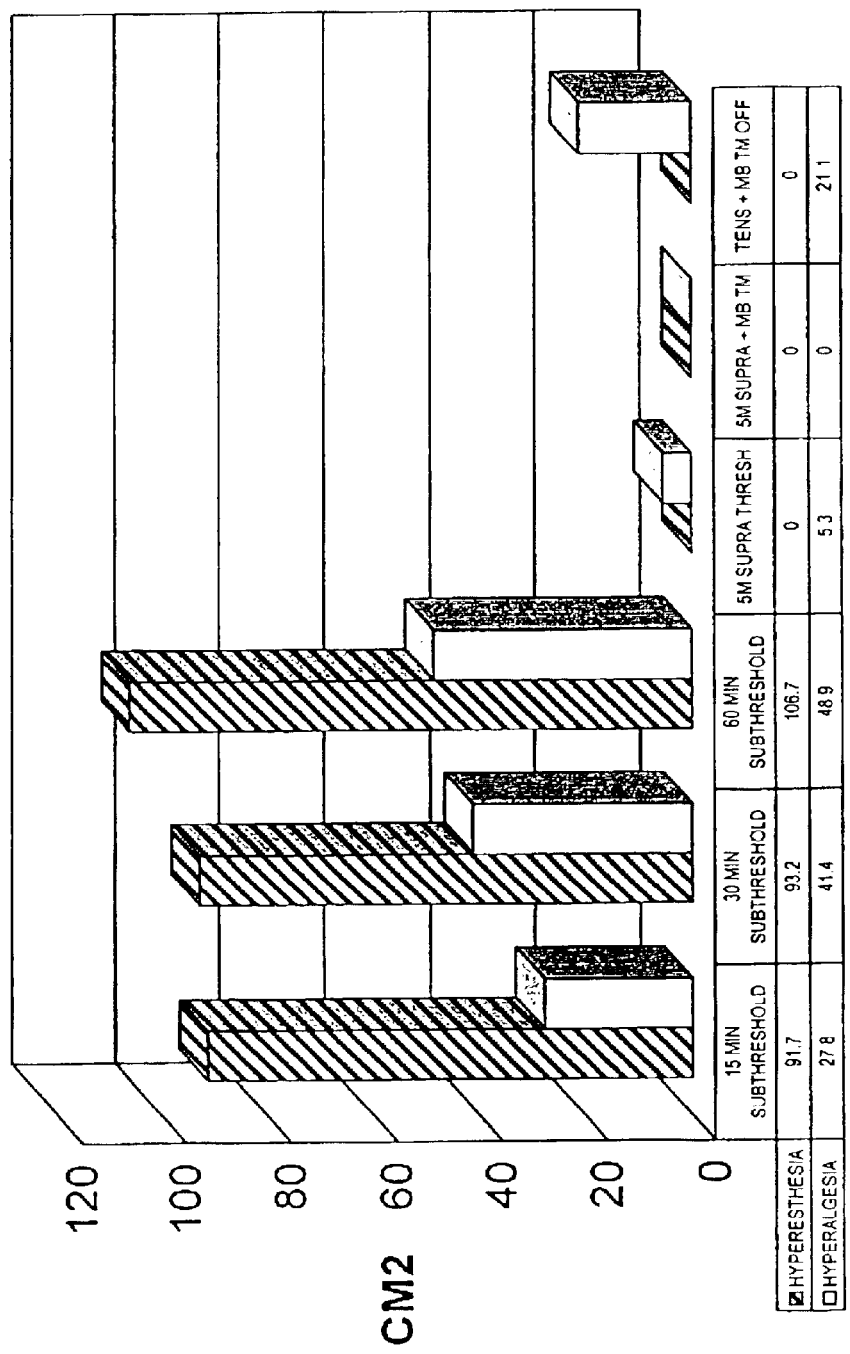
Figure 74:
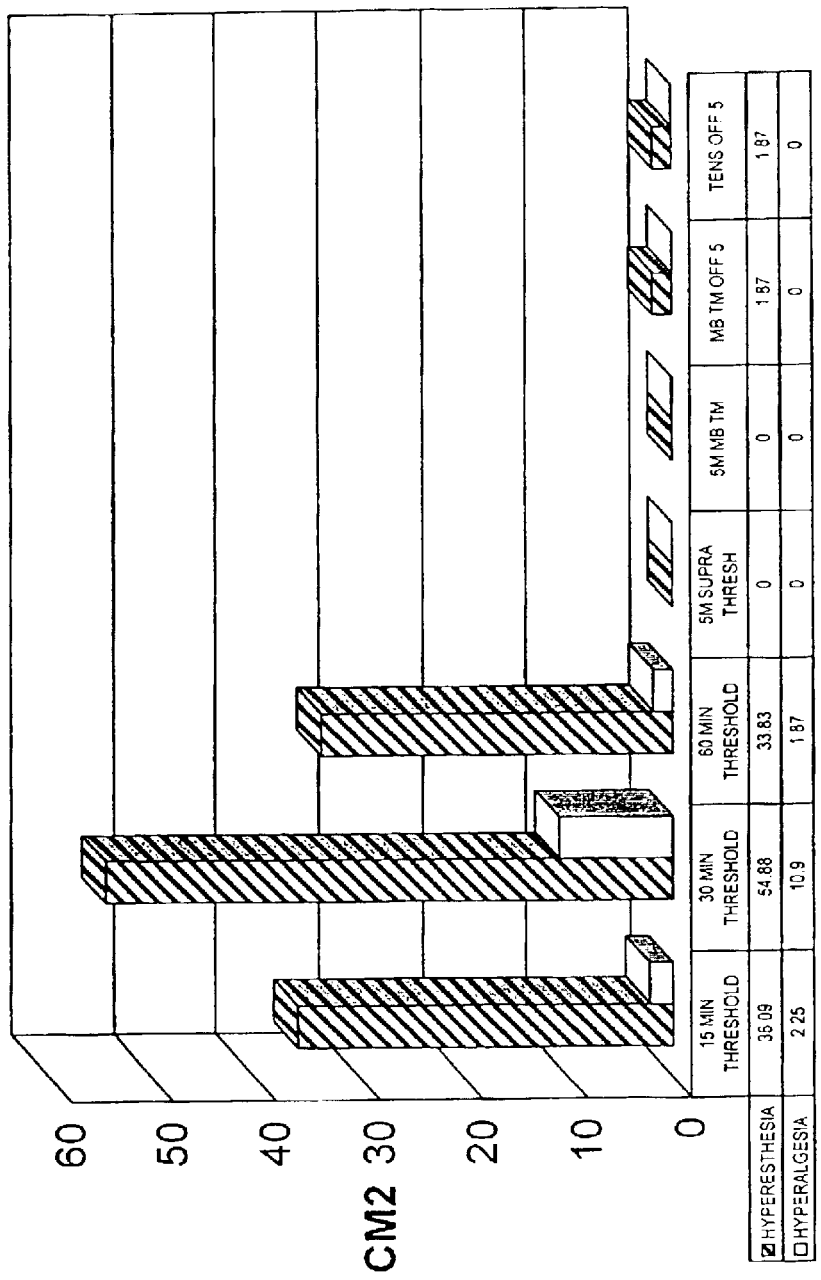
Figure 75:
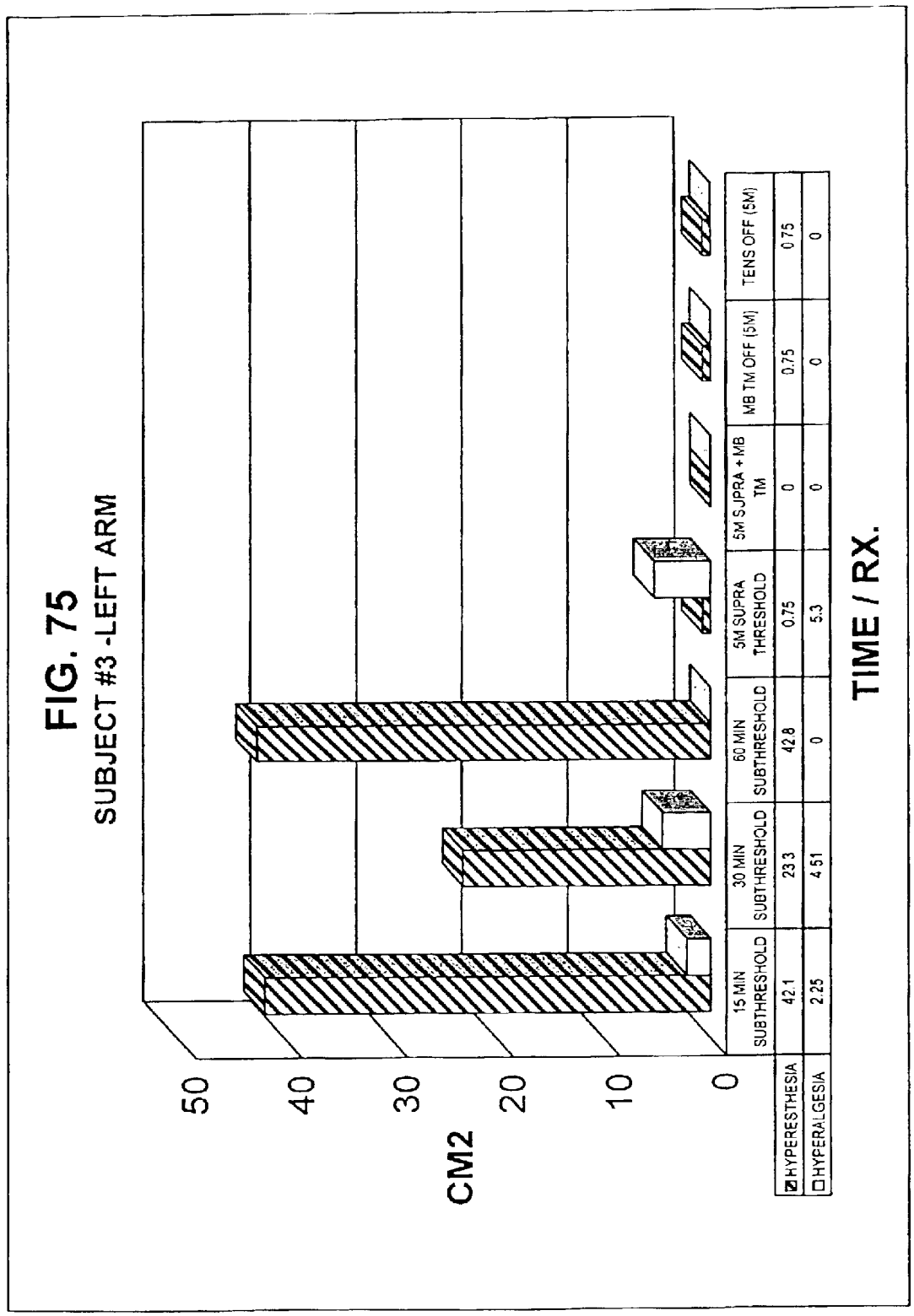
Figure 76:
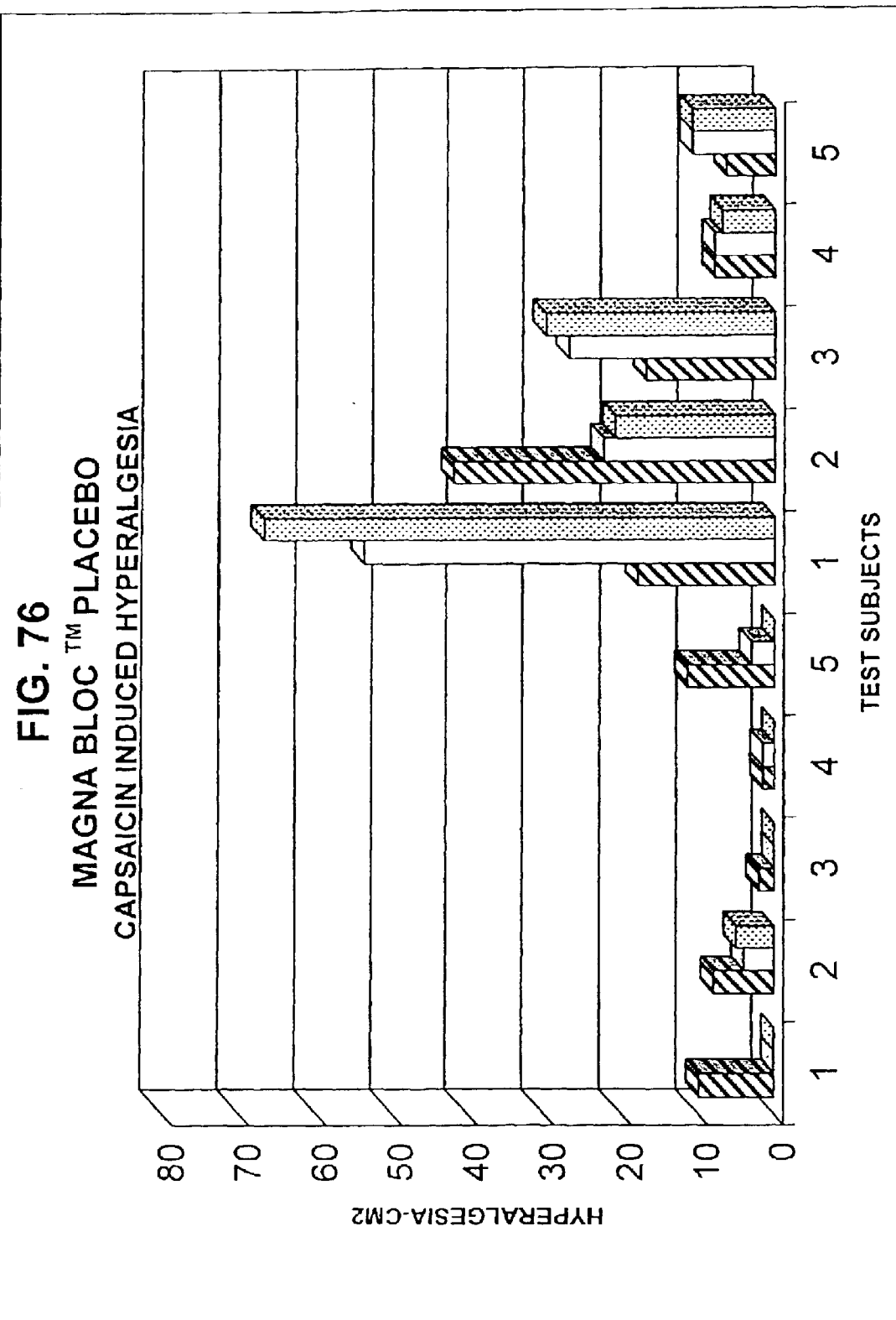
Figure 77:
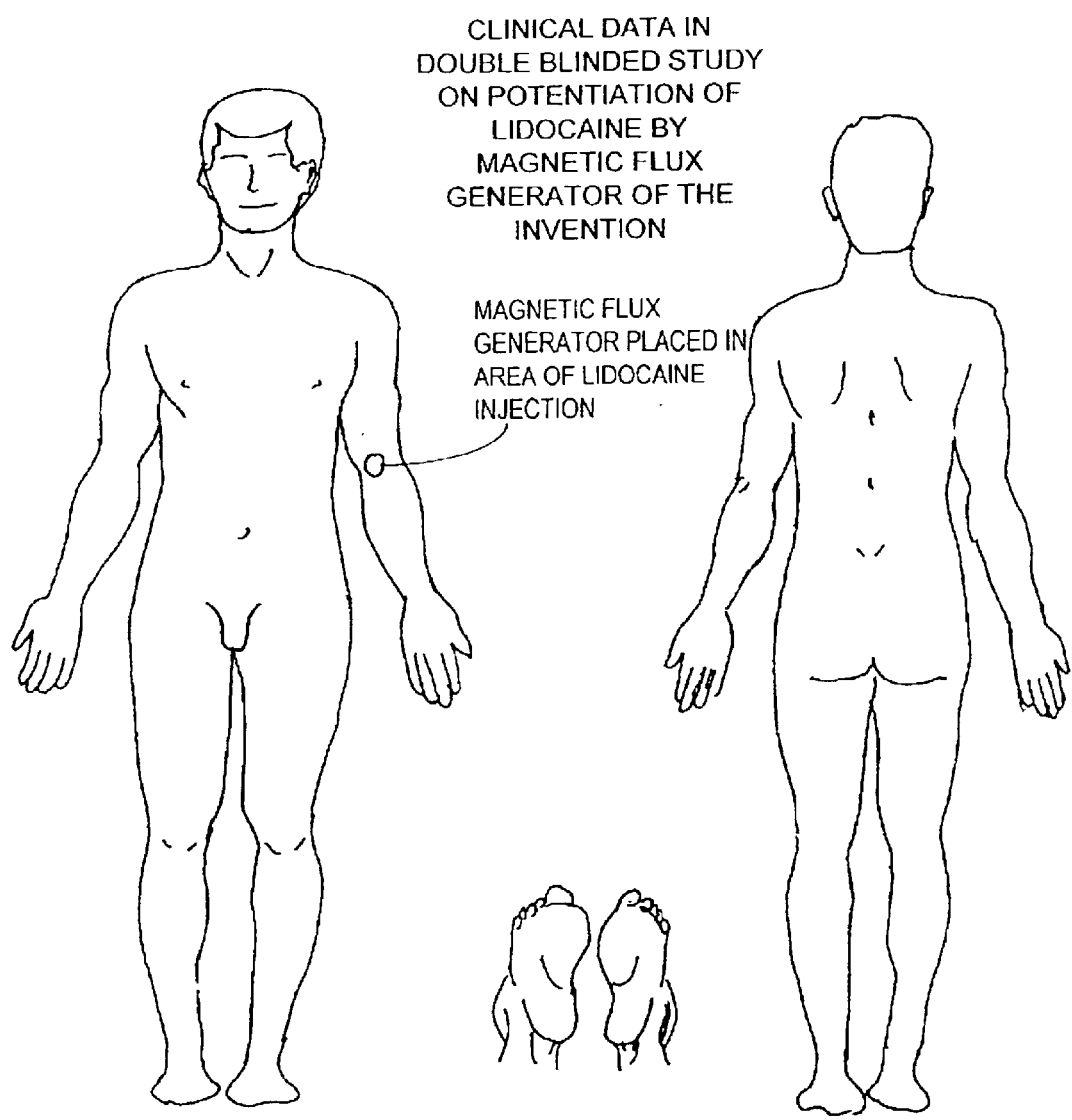
Figure 80:
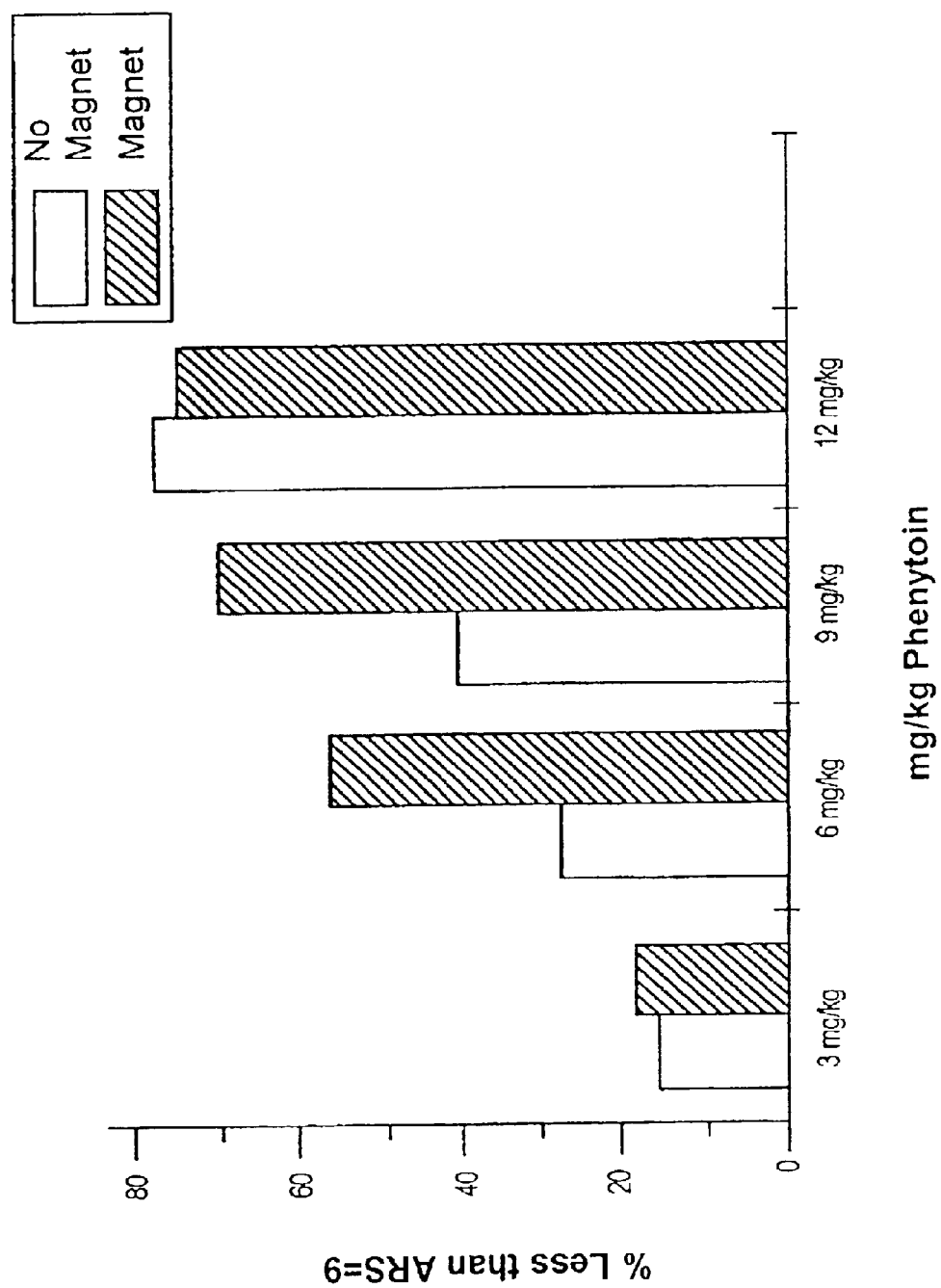

G. Cardiac Dysfunction
 FIG. 57 Human Figure with Cardiac application
 FIG. 58 Figure with internal implantable
H. Control of Pain and Sludging of Sickled Cells in Sickle Cell Disease
 FIG. 59 Placement of Human Body
I. Seizure Disorders
 FIG. 60 Human External application
 FIG. 61 Human Implantables
J. Treatment of Movement Disorders
 FIG. 62A Attachment to the head
 FIG. 62B Implant near the basal ganglia
K. Protection of Transplant Organs
 FIG. 63 Transport Box
 a b c
N. MagnaScan™ Device for Locating and Confirming the Placement of the Quadripolar Magnet Device in the Treatment of Pain and Other Dysfunctions
 FIG. 65 Device—Side view according to one embodiment of the invention.
 FIG. 66 Rear view showing controls and liquid crystal display.
 FIG. 67 Front view of the scan device showing the 2 turrent mounted annub electrodes.
 FIG. 68 Schematic representation of anatomical connections associated with pain perception.
 FIG. 69 Relationship of current density to control of peripheral C-fiber firing as measured by the area of hyperalgesia following intradermal capsaicin injection.
 FIG. 70 time and current density relationships on the evolution of hyperesthesia and hyperalgesia, following intradermal capsaicin injection.
 FIG. 71 Relationship of current density, time and magnetic field of the invention to the evolution of hyperesthesia and hyperalgesia, following intradermal capsaicin injection.
 FIG. 72 Relationship of current density, time and magnetic field of the invention to evolution of hyperesthesia and hyperalgesia, following intradermal capsaicin injection.
 FIG. 73 Same as 1.6 FIG. 72.
 FIG. 74 Same as 1.6 FIG. 72.
 FIG. 75 Same as 1.6 FIG. 72.
 FIG. 76 Relationship of time in both quadripolar alternating field magnetic device of the invention and magnetic placebo to evolution of hyperalgesia after injection of capsaicin in the forearm.
O. Potentiation of Pharmaceuticals for Focusing and for Concentrating the Drug to the Active Site
 FIG. 77 Embodiment on Human Body—Potentiation of Lidocaine
 FIG. 80 Shifting of Dose response curve of Dilantin

DETAILED DESCRIPTION

Device

This invention provides a device with four magnetic poles of alternating polarity in which the shape of the poles is in the form of two cones joined at the directrix with the vertex of the two cones lying in a perpendicular axis of a circular directrix of the cones such that the vertex of the cone shaped magnetic bodies may all be tilted toward (or away from) the midline (on the side facing the animal body) such that the peak or vertex migration toward the midline will vary (or sharpen the angle of) the field gradient.

There is further taught the method which provides a device with four magnetic poles of alternating polarity in which the shape of the poles are in the form of a single cone with the vertex of the cone facing the body of the animal and the directrix of the cone attached to the flux return ring and facing away from the animal body. The vertex may be tilted toward the midline (on the side facing the animal body) such that the peak or vertex migration toward the midline will alter the field gradient.

It is a further object of this invention to provide a device which contains a flux return ring on the back surface away from the body surface which is designed to return the magnetic flux thereby altering (increasing) the strength and gradient without materially altering the center charge symmetry and homogeneity of the 3 dimensional steep gradient field.

Another object of the invention is to provide a flux focusing ring surrounding the 4 (static) magnetic poles on the outer perimeter stationed substantially midway between the top and bottom of the pole. Attachment means is provided to hold the focusing ring to the outer perimeter of the poles throughout the total support means.

It is a further object of the invention to provide a static magnetic pole of like polarity on the outer surface of each of the 4 poles of the invention (focusing magnet) such that the top of the focusing magnet is oriented to the geometric side of the pole such that the axis of the two magnets form a 45 to 90 degree angle or a 90° to 135° angle. The focusing magnet comprises a static magnetic pole.

It is a further object of the invention to provide a static magnetic pole of like polarity on the outer surface of the flux focusing ring adjacent to each of the 4 poles of the invention (focusing magnet) such that the end or top of the focusing magnet is oriented to the geometric side of the pole such that the axis of the two magnets form a 45 to 90 degree angle. The focusing magnet comprises a static magnetic pole. The angle of the focusing magnet is such that the axis forms a 45 to 90 degree angle on the body surface side and a 90 to 135 degree to the surface away from the body.

It is a further object of the invention to control the focusing of each magnet with a smaller and weaker magnet than the primary pole such that the focusing ring containing magnets can focus and balance the symmetry of the therapeutic field A further object of this invention is to reveal a method of design and manufacture of an inexpensive, center charged and homogeneous static magnetic flux magnet.

Preferably; the plurality of magnet bodies in each device comprises four substantially identical static magnets, the static magnetic poles are the shape of a cylinder or preferably in the shape of two cones joined at the directrix of the cone with the vertex of the two cones lying in a perpendicular axis of the circular directrix such that the vertex of the double cone shaped magnetic bodies may all be tilted toward the midline (on the side facing the animal body) such that the peak or vertex being pulled toward the midline will give a more steep field gradient.

It is further preferred that the device contains a flux return ring on the back surface away from the body surface which is designed to return the magnetic flux thereby increasing the strength and gradient without altering the center charge symmetry and homogeneity of the 3 dimensional steep gradient field.

It is further preferred that a flux focusing ring surrounds the 4 static magnetic poles on the outer perimeter stationed midway between the top and bottom of the pole at the junction of the base of the two cone shapes which join at the directrix of the cone.

On the outer surface of each of the 4 poles of the invention attached to the flux focusing ring is a small focusing cylindrical magnet oriented to the geometric side of the pole such that the axis of the two magnets from a 45 to 90 degree angle (Focusing magnet/Magnet pole=¼ in size). It is further preferred that the containment means be plastic which covers the entire embodiment. The size of the device is dictated by the application, but averages about 1"x¼" inches in the round.

It is a further object of the invention to present a method of adding a plastic material to a permanent magnet amalgam along with a proprietary silica colloid and curing the amalgam under the influence of a strong, center charged homogenous magnetic field.

Pain Applications
A. Pain and Swelling and Wound Healing
  1. Acute Pain and Edema
  It is a further object of the invention to provide a device that alters nerve cell behavior in a manner that reduces painful sensations.

Another object of the invention is to provide an apparatus for applying a symmetric quadripolar, three dimensional magnetic flux field which is focused and balanced to the human body to stabilize excitable membranes and thereby reduce pain and edema associated with acute injury, inflammation or surgical procedure and to decrease wound healing time.

Another object of the invention is to provide a specialized magnetic flux field to control and reverse the swelling associated with acute injury, inflammation and surgery.

A further object of the invention is to provide a method for applying a therapeutic magnetic device to the human body to relieve pain, improve blood flow, decrease healing time, and reduce swelling associated with injury, surgery or acute inflammation.

2. Chronic Pain
  It is a further object of the invention to provide a device that alters nerve cell behavior in cases of chronic pain to block the spontaneous pacemaker firing of the chronically malfunctioning pain fiber (mostly A-fibers and C-fibers).

Another object of the invention is to provide an apparatus for applying a symmetric, quadripolar, three dimensional magnetic flux field which is focused and balanced to the human body to stabilize excitable membranes and thereby reduce pain associated with the spontaneous pacemaker firing of chronically malfunctioning polymodal nociceptors (afferent C-fibers and A8 fibers).

Another object of the invention is to provide a specialized magnetic flux field to control and speed healing of chronic non-healing wounds.

In accordance with the principles of the present invention as embodied and as broadly described herein, a therapeutic static magnetic treatment device adapted for placement against the bodies of living animals is provided. The device comprises a plurality of static magnetic bodies having at least two positive and two negative magnetic poles substantially in a single plane, the magnetic poles being oriented to define the four vertices of a quadrilateral shape, the two positive poles defining opposite diagonal vertices and the two negative poles defining opposite diagonal vertices of the quadrilateral shape. Each of the magnetic poles being magnetically attracted by the two oppositely charged poles and being magnetically repelled by the like charged poles.

B. Pain and Edema Sustained in Minor Bums Insect Bites, Bee Stings and Minor Cuts and Abrasions.

The present invention relates to magnetic devices for therapeutic application to the human body, and more particularly to a small disposable, multiple quadripolar treatment device contained in a small sterile disposable bandage for placement on the human body for control of pain and edema sustained in minor bums, insect bites, bee stings and minor cuts and abrasions.

Preferably, the invention will provide a magnetic device that alters the permeability of the ion channels in membranes to the flow of sodium and calcium and thereby stabilizes the spontaneous firing of damaged nerve endings as well as restores the physical integrity of the membranes and thereby stops the abnormal loss of cellular fluid (edema).

Minor bums, insect bites, bee stings and minor cuts and abrasions are the most common injuries in our society, yet they are among the most painful and annoying injuries in our society. The only treatment for mass use is cleansing, antibiotic ointment and clean bandage.

There is a great need for a bandage which will provide a sterile cover for such wounds as well as to acutely control pain, swelling and to promote healing.

Accordingly, it is an object of the invention to provide a device that is small enough to be contained in a small sterile bandage "Band-Aid" inexpensive enough to be disposable and that alters pain fiber firing, repairs membrane integrity, controls edema in the area of the injury and promotes healing.

Another object of the invention is to provide a magnetic device that alters the permeability of the ion channels in membranes to the flow of sodium and calcium and thereby stabilizes the spontaneous firing of damaged nerve endings as well as restores the physical integrity of the membranes and thereby stops the abnormal loss of fluid by cells.

C. Foot Pain and Discomfort.

Another object of the invention is to present an embodiment of the present invention which relates to magnetic devices for therapeutic application to the human body, and more particularly to a quadripolar static magnetic device adapted for the utilization in the soles of shoes employing a new and very economic method of manufacturing and applying the magnet of the invention to the soles of shoes.

The present invention relates to magnetic devices for therapeutic application to the human body, and more particularly to a quadripolar static magnetic device with gradient focusing means for utilization in the soles of shoes.

Pain sensations in the human body can be a result of improper nerve function, as when such pain or discomfit is caused by inordinately excitable nerve cells or by nerve cells having leaky cell wall membranes. Pain sensations may also be caused by damaged or contused nerve cells. Even when nerves function properly, fatigue and pain sensations are initiated through nerve cells which are irritated by fatigued tissue. Thus, relief from foot pain and fatigue should be obtainable by altering nerve cell function, as for example by stabilizing nerve cell wall membrane.

Unfortunately, many types of foot fatigue and pain cannot be successfully treated with conventional drug or physical therapies. Because foot fatigue and pain induced by standing, walking or running are often untreatable with conventional therapies, there is a need for alternative therapies that relieve these symptoms by altering nerve function and blood circulation in the feet. Accordingly, it is an object of the invention to provide a magnetic device and method for applying the device against the human foot so as to alter nerve behavior in a manner that reduces foot fatigue and pain. It is a further object of the invention to provide a magnetic device and a method for applying the device against the human foot so as to improve blood circulation.

It is preferred that the containment means for the invention be made of a flexible material so that placement in a shoe sole will not restrict flexibility.

In accordance with the invention, at least one therapeutic permanent magnet device is embedded in a shoe. Preferably, one permanent magnet device is embedded in the heel of the shoe's sole while a second device is embedded in the portion of the shoe's sole corresponding to the ball of the foot. The shoe into which the magnetic treatment devices are embedded may be of any type of footwear, as for example, running shoes, nurses shoes or work boots.

It is further preferred that the device be at a low enough cost to make placement in a shoe economically feasible. It is therefore desired that the best product be produced for the lowest price. Therefore, a method will be revealed for forming the magnetic nucleus of the device in one simple molding process and the device will then be placed in a vulcanized rubber embodiment for placement in the shoe.

D. Cumulative Trauma Disorder.

It is a further object of the invention to provide a device that alters nerve cell behavior in cases of chronic pain to block the spontaneous pacemaker firing of the chronically inflamed, edematous, malfunctioning pain fibers in chronic trauma disorders such as Carpel Tunnel Syndrome.

Another object of the invention is to provide an apparatus for applying a symmetric, quadripolar, three dimensional magnetic flux field which is focused and balanced to the human body to stabilize excitable membranes and thereby reduce pain associated with the spontaneous pacemaker firing of chronically traumatized and malfunctioning polymodal nociceptors.

Another object of the invention is to provide a specialized magnetic flux field to remove edema and control pain in a chronically traumatized tissue.

It will be apparent to those skilled in the art that the apparatus of this invention alters C-filters firing both in vitro and in vino.

Additionally, the invention provides a static magnetic pole of like polarity on the outer surface of each of the 4 poles of the invention (focusing magnet) such that the top of the focusing magnet is oriented to the geometric side of the pole such that the axis of the two magnets form a 90° to 135° angle. The focusing magnet comprises a static magnetic pole.

This application further reveals a method and technique for placement of the devices over areas of chronic trauma such that they will alter nerve cell behavior in cases of chronic pain to block the spontaneous pacemaker firing of the chronically traumatized, enflamed, edematous, malfunctioning, pain fiber in chronic trauma disorders such as Carpel Tunnel Syndrome.

Additional objects and advantages of the present invention will be set forth in part in the description that follows and, in part, will be from the description or may be learned by practice of the invention.

E. Control of Edema and Pain as well as Speed Healing Following Surgical Procedures and Speed Healing Rates of Chronic Non-Healing Wounds.

This application further reveals a method and technique for placement of the invention on post operative incisional sites for the benefit of pain control, edema control and increased healing rates.

There is taught a device providing an apparatus for applying a symmetric quadripolar, three dimensional magnetic flux field which is focused and balanced to the human body to stabilize excitable membranes and thereby reduce pain and edema associated with acute injury, inflammation or surgical procedure and to decrease wound healing time as well as speed healing of tissue following surgical procedures and speed healing rates of non-healing wounds.

There is further taught the method which provides for applying a therapeutic magnetic device to the human body to relieve pain, improve blood flow, decrease healing time, and reduce swelling associated with injury, surgery or acute inflammation along with reducing or blocking swelling and speed healing following surgical procedures.

There is further provided the device which provides a specialized magnetic flux field to control and speed healing of chronic non-healing wounds.

There is further taught the methods, devices, techniques, and processes which relate specifically to control of edema and pain as well as speed healing following surgical procedures and speed healing rates of chronic non-healing wounds.

There is further taught the method which provides a device that alters cell behavior in a manner that reduces pain, swelling and speeds healing following operative procedures and of non-healing wounds and speeds healing.

1. Post Operative Treatment

It is a further object of this invention to provide a device that alters cell behavior in a manner that reduces pain, swelling and speeds healing following operative procedures.

There is further taught the device which provides a specialized magnetic flux field to control and reverse the swelling associated with acute injury, inflammation and surgery.

Another object of the invention is to provide an apparatus for applying a symmetric quadripolar, three dimensional magnetic flux field which is focused and balanced to the human body to stabilize excitable membranes and thereby reduce pain and edema as well as speed healing of tissue following surgical procedures.

A further object of the invention is to provide a method for applying a therapeutic magnetic device to the human body to relieve pain, improve blood flow, reduce or block swelling and speed healing following surgical procedures.

2. Chronic Non-Healing Wounds

It is a further object of this invention to provide a device that alters cell behavior in a manner that reduces pain, swelling and speeds healing of non-healing wounds.

Another object of the invention is to provide an apparatus for applying a symmetric quadripolar, three dimensional magnetic flux field which is focused and balanced to the human body to stabilize excitable membranes, improve blood flow, relieve pain, reduce swelling and speed healing rates of non-healing wounds.

It is a further object of the invention to present an application of the quadripolar array in a microscopic embodiment which is housed in a catheter designed to be placed in the epidural space and other body cavities such that the magnetic quadripolar flux generators are arranged in a helix such that migration or rotation of the device will not alter the efficacy of the therapeutic device.

F. Potentiation of Epidural Anesthesia and Epidural Analgesia.

There is taught the embodiment of implantable quadripolar devices which contain flux focusing and flux return rings.

There is further taught the application of the quadripolar array in a microscopic embodiment which is housed in a catheter designed to be placed in the epidural space and other body cavities such that the magnetic quadripolar flux generators are arranged in a helix such that migration or rotation of the device will not alter the efficacy of the therapeutic device.

There is further taught the methods, devices, techniques, and processes which relate specifically to potentiation of epidural anesthesia and epidural analgesia.

There is further taught he methods, devices, techniques, and processes which specifically relates to a method for using submicroscopic, quadripolar, circular, center charged, energy balanced magnetic device in a four (4) magnet array of alternating polarity in which the magnetic poles are separated only by a distance which will allow a magnetic sphere of influence on all adjacent poles to suppress the firing of action potentials of mammalian sensory neurons.

There is further taught the method which provides for applying a magnetic field which is particular to this device, to a nerve cell such that it alters nerve behavior.

There is further taught the method which provides applying the magnetic field to the dorsal root ganglia by placing the device in the epidural space adjacent to the dorsal root.

There is further taught the method which provides for a catheter to modulate or suppress C-fiber firing.

There is further taught the method which provides for the helical design of the catheter so as to allow impingement of the dorsal root regardless of the catheter's rotation.

There is further taught the method which provides for a magnetic device with a configuration of static magnets with a particular pole design that, when placed close to a nerve cell, alters the nerve cell's responses to external electrical stimuli.

In accordance with the principles of the present invention as embodied and as broadly described herein, a method for suppressing nerve cell (particularly C-fiber) action potentials is provided. According to the invention, a magnetic treatment device is placed at such a distance from a mammalian sensory neuron that the magnetic field of the treatment device reaches the sensory neuron. During such placement, and for a period thereafter, the nerve cell action potentials are suppressed.

The magnetic treatment devices is comprised of four magnetic bodies having two positive and two negative magnetic poles substantially in a single plane, the magnet poles being oriented to define the four vertices of a quadrilateral shape, the two positive poles defining opposite diagonal vertices, and the two negative poles defining opposite diagonal vertices of the quadrilateral shape. Containment means are provided for holding the magnetic poles of the magnetic bodies in the quadrilateral orientation in the catheter by embedding the submicroscopic magnet devices in the wall of the catheter. The plurality of magnet bodies comprises four substantially identical cylindrical magnetic bodies, each having one magnetic center charge face. It is necessary that two of the cylindrical magnetic bodies have a positive magnetic pole on one face and two of the magnetic bodies have a negative magnetic pole on one face, and that the two positive and two negative magnetic poles on the magnetically charged faces of the four magnet bodies be in the quadrilateral orientation described above. The proximity of the individual magnets within the device must be maintained. Separation of the individual magnets or bringing the device in close proximity to other magnets will cause interference with the magnetic field and will change the flux lines and gradient of the field so that the device will not effectively alter the C-fiber firing.

The present invention relates to a method for using submicroscopic, quadripolar, circular, center charged, energy balanced magnetic devised in a four (4) magnet array of alternating polarity in which the magnetic poles are separated only by a distance which will allow a magnetic sphere of influence on all adjacent poles to suppress the firing of action potentials of mammalian sensory neurons. These submicroscopic magnetic arrays are placed in an epidural catheter. They are placed in a helical arrat with the distance between magnetic clusters being 1 cm (a distance which breaks the sphere of influence, one cluster field to another). The cluster are rotated about 43° in succession one cluster to the next. There is a difference in electrical potential across a cell membrane of sensory neurons. When a neuron receives an impulse transmitted from another nerve cell, the electrical potential difference across the membrane of the cell is dramatically reduced and generally reverses. This reduction and reversal of potential is referred to as the firing of the neurons action potential. If such action potential firings are suppressed, the transmissions of nerve impulses are also suppressed.

Pain sensations in the human body can be a result of improper nerve function, as when such pain is caused by inordinately excitable nerve cells or by nerve cells having cell wall membranes that leak ions. Pain sensations may also be caused by damaged nerve cells, as for example nerve cells suffering from post-operative scarring or physically impinged nerve cells commonly associated with degenerative disc disease. Even when nerves function properly, chronic pain sensations are initiated through nerve cells. Thus, new ways of altering nerve cell function, as for example by stabilizing nerve cell wall membranes, may lead to new therapies for the treatment of pain.

Accordingly, it is an object of the invention to provide a method for applying a magnetic field which is particular to this device, to a nerve cell such that it alters nerve behavior. This invention relates to a method of applying the magnetic field to the dorsal root ganglia by placing the device in the epidural space adjacent to the dorsal root. In this location, the catheter will modulate or suppress C-fiber firing. Modulation of C-fiber firing will intercept the pain pathway in both somatic and sympathetically mediated pain. The helical design of the catheter allows impingement of the dorsal root regardless of the catheter's rotation.

Another object of the invention is to provide a magnetic device with a configuration of static magnets with a particular pole design that, when placed close to a nerve cell, alters the nerve cell's responses to external electrical stimuli. In order to achieve the result on nerve cells, it is necessary that the proximity of the individual magnets within the device be maintained such that each pole exerts a sphere of magnetic influence on the other poles in the device. Any alteration of the proximity of the magnets one to another, with alternating polarity, will change the effect or cause no effect upon the cell. Any alteration in the balance and symmetry of the power of each individual pole with respect to the other three poles will likewise impair the effect upon the cell.

It will be apparent to those skilled in the art that the apparatus of this invention alters C-fiber firing both in vitro and in vivo.

Additional objects and advantages of the present invention will be set forth in part in the description that follows and, in part, will be apparent to those skilled in the art from the description or may be learned by practice of the invention.

G. Cardiac Dysfunction.

There is taught the methods, devices, techniques, and processes which specifically relate to magnetic devices for therapeutic application to the human body, and more particularly to a static permanent quadripolar treatment device for placement in proximity to the human heart to control angina pectoris ("chest pain") and cardiac dysrhythmia.

There is further taught the method which provides a device that alters myocardial behavior in a manner which stabilizes the electrical activity, dilates myocardial arteries, protects cells from cell death and controls chest pain which is secondary to ischemia. Another object of the invention is to provide a magnetic device that alters myocardial behavior in a manner which controls myocardial ischemia and chest pain.

There is further taught the method which provides a magnetic device that alters myocardial behavior by altering sodium and calcium channel function such that the quadripolar, alternating polarity and the subsequent field gradient block varying degrees of sodium and calcium channel function. The degree of blockage is related to the gradient and strength of the field. The gradient and the field strength may be manipulated by this technology.

There is further taught the method which provides an apparatus for applying a variable magnetic flux to the human body in the area of the heart by manipulating components, size and location of the apparatus.

Application of the present invention relates to magnetic devices for therapeutic application to the human body, and more particularly to a static permanent quadripolar treatment device for placement in proximity to the human heart to control angina pectoris ("chest pain") and cardiac dysrhythmia. The three dimensional flux field gradient, when applied to the area of the heart which controls arrhythmia, improves blood flow, controls angina and protects ischemic myocardial muscle from cell death.

Heart disease secondary to coronary disease is a major health problem world wide. A common early sign of coronary artery disease is coronary pain secondary to ischemia. The customary treatment involves the use of small vessel dilators such as nitroglycerin, calcium channel blockers and beta adrenergic blockers. These agents have significant side effects associated with their use and many times they do no control the pain. This condition is referred to as refractory angina pectoris. The device of this invention is effective in control of refractory angina pectoris and is actually potentiates the effects of the pharmaceuticals, especially calcium channel blockers.

Accordingly, it is an object of this invention to provide a device that alters myocardial behavior in a manner which stabilizes the electrical activity, dilates myocardial arteries, protects cells from cell death and controls chest pain which is secondary to ischemia. Another object of the invention is to provide a magnetic device that alters myocardial behavior in a manner which controls myocardial ischemia and chest pain.

Another object of the invention is to provide a magnetic device that alters myocardial behavior by altering sodium and calcium channel function such that the quadripolar, alternating polarity and the subsequent field gradient block varying degrees of sodium and calcium channel function. The degree of blockage is related to the gradient and strength of the field. The gradient and the field strength may be manipulated by this technology.

It is a further object of the invention to provide an apparatus for applying a variable magnetic flux to the human body in the area of the heart by manipulating components, size and location of the apparatus.

H. Control of Pain and Sludging of Sickled Cells in Sickle Cell Disease.

There is taught the methods, devices, techniques, and processes which relate specifically to control of pain and sludging of sickled cells in sickle cell disease. Particularly a method which implements the invention to alter cell behavior in a manner that reduces sickle cell symptoms is taught.

This invention, when properly placed, provides a device that alters cell behavior in a manner which blocks or reverses the acute sickling process which leads to low oxygen carrying capacity and sludging of the sickled cells which causes pain and infection of major organs. The device of the present invention also controls the pain which is associated with sickling.

The position of the devices is dictated by the location of the pain in sickle cell crisis. The device may be used prophylactically to prevent sickle cell symptoms.

The device provides for effective acute relief from sickle cell crisis and provides for prophylactic use of the devices in some instances.

Seizure/Movement Control Applications

In accordance with the principles of the present invention as embodied and as broadly described herein, a therapeutic static magnetic treatment device-adapted for placement of each device on the head of living animals is provided.

Evidence is presented and provided that the 3 dimensional, steep gradient field created by the invention effectively stops neuronal discharge in the central nervous system and inhibits or reverses cerebral edema.

I. Seizure Control:

This application of the present invention relates to magnetic devices for therapeutic application to the human body, and more particularly to a quadripolar treatment device for placement on either the outside of the human head or implantable units for control of seizure disorders.

Seizure activity in the brain is a rather common occurrence. Clinical seizures result from uncontrolled firing of the brain neurons. This uncontrolled, spontaneous discharge may have projections to many parts of the brain, causing a variety of clinical presentations. These seizures are controlled in many patients by anticonvulsant drugs which work through the alteration of ion channels. The drugs increase the seizure threshold by stabilizing neuron cell wall permeability to ion flux. Many of these seizures are not well controlled by medication nor any other available modalities. A significant number of these seizures are resistant to all modalities of treatment. These poorly controlled patients have a few seizures per month to several per day. Frequent and prolonged seizures cause significant and progressive brain damage.

Accordingly, it is an object of the invention to provide a device that alters brain neuronal behavior in a manner which substantially stops the abnormal electrical discharge of the neurons, therefore stopping the seizures.

Another object of the invention is to provide a magnetic device that alters brain neuronal behavior in a manner which substantially stops and controls drug resistant seizures.

Another object of the invention is to provide a method of applying a therapeutic magnetic device to the human head to relieve seizures.

It is another object of the invention to demonstrate a method of external attachment of the therapeutic quadipolar magnetic device to the area of the head, a method of implanting the device in the skull table and a method and apparatus for implanting the device intracerebrally.

Further taught are methods of implanting the therapeutic quadipolar magnetic device in The skull table or intracerebrally.

J. Treatment of Movement Disorders.

The present invention relates to magnetic devices for and methods for therapeutic application to the human body, and more particularly to a device for application of the human head in the area of the basal ganglia and/or application of a small implantable device to place in the appropriate location in the area of the basal ganglia.

This invention provides a device (and a method for its applications) which is adaptable to be applied to the skin of the head or implanted under stereotactic guidance into areas of the boral ganglia for the control of movement disorders, the device may be used either alone or in combination with medication, either to augment or to potentiate the drug effects.

Movement disorders such as Parkinsonism are treated with drugs and currently an experimental implantable electrical stimulator is being evaluated. Drugs have a narrow therapeutic window in this particular complex of disorders and the electrical stimulator is cumbersome and requires batteries. There clearly is need for a more simple and effective technology which has few to no side effects.

Accordingly, it is an object of the invention to provide a device which is adaptable to be applied to the skin of the head or implanted under stereotactic guidance into desired areas of the brain for the control of movement disorders, the device may be used either alone or in combination with medication, either to augment or potentiate the drug effects.

Accordingly, it is an object of the invention to provide a device which is adaptable to be applied to the skin of the head or implanted under stereotactic guidance into desired areas of the brain for the control of movement disorders, the device may be used either alone or in combination with medication, either to augment or potentiate the drug effects.

Delay of Cell/Tissue Decay Applications

K. Protection of Transplant Organs.

There is taught the method which provides a device to better maintain cell integrity of transplantable organs by transporting them in a container equipped with a quadripolar magnetic flux generator which covers the organ with a step gradient quadripolar static magnetic flux field during transport.

In accordance with the principles of the present invention a therapeutic static magnetic treatment device adapted for placement inside a human organ transplant transport cooler is presented.

The current invention is designed to better maintain the cell integrity of the transplantable organ by transporting it in a container which is equipped with a quadripolar magnetic flux generator which covers the organ with a steep gradient, quadripolar, static magnetic flux field during transport. The field has been shown to possess the ability to offer significant protection from cell death.

This invention further presents the embodiment of the magnetic field in a transport container for such organs as hearts, livers, kidneys, lungs and pancreases.

Organ transplantation represents the greatest hope in medicine today for the effective management of patients in which entire organ systems have failed. Many problems must be dealt with in the successful transplantation of freshly harvested human organs. A major problem is time from harvesting to transplantation. The donor is frequently hundreds of miles and several hours from the recipient. The organs are chilled in saline glucose in an attempt to slow metabolism and retard catabolism and shock of the organ. The efforts are not totally successful in preserving a good quality organ for transplant. However, due to the shortage of transplantable organs, the less than optimal organs are usually used.

There is need for a system which will better maintain the integrity of the organ such that it is delivered in optimal condition to the transplant recipient.

A purpose of the present invention is to better maintain the cell integrity of the transplantable organ by transporting it in a container which is equipped with a quadripolar magnetic flux generator which covers the organ with a step gradient quadripolar static magnetic flux field during transport. This field has been shown to possess significant protection from death for isolated cells and organs in the laboratory.

L. Protection from Cell Injury and Death Following Neuronal Cell Insults Such as Contusion. Hypoxia, Stroke and Infection.

This application further reveals a method and technique for placement of the devices on the external body area overlying neuronal tissue such as brain, spinal cord and peripheral nerves following cell insults such as contusion, hypoxia, stroke, bleeding and infection.

This application of the present invention relates to magnetic devices for therapeutic application to the human body, and more particularly to a quadripolar treatment device for placement on the human head, spinal cord or other accessible nervous tissue. to protect injured or insulted cells from cell death.

Cerebral ischemia can be either focal or global, employing hypoperfusion of a portion or all the entire brain. Ischemia is secondary to reduction of cerebral blood flow either locally or globally. Histologically selective neuronal necrosis may occur even after brief periods of global ischemia, and after focal ischemia there may be regions of pan necrosis in the territory of the affected artery. Progressing stroke is an observed deterioration after the initial insult that can occur for 48 to 96 hours. This phenomenon is likely related to a combination of evolving thrombosis and progressive cell death. Cell death occurs secondary to hypoxia, spillage of excitatory neurotransmitters, and spillage of calcium secondary to dying cells in the region.

It is the purpose of this invention to present animal data which demonstrates protection of brain and other nervous tissue from cell death in animals who have suffered ischemia or other insults to the nervous tissue. Data will also be presented which demonstrates protection from brain cell death following direct injection of toxic amino acids into the lateral ventricles.

A further purpose of this invention are planned clinical trials for protection from cell death and the reduction of edema in intracranial hemorrhage, strokes, infections, trauma and spinal cord injuries.

M. Magnetic Treatment Device for Treatment of Neurological Deficits Including Residual Encephalopathy Following Neurological Insults such as Strokes—For Protection from Cell Death and Dysfunction Following Hypoxic Injuries There is taught the methods, devices, techniques, and processes which relate specifically to protection from cell injury and death following neuronal cell insults such as contusion, hypoxia, stroke and infection. Also taught is application to the human body, and more particularly to a quadripolar treatment device for placement on the human dead, spinal cord or other accessible nervous tissue, to protect injured or insulted cells from cell death.

This application of the present invention relates to magnetic devices for therapeutic application to the human body and more particularly to a magnetic skull cap which utilizes appropriately placed quadripolar devices of the invention for placement on the human head for the application of several quadrilateral, steep, three dimensional magnetic flux field gradient devices.

This application further reveals a method and technique for placement of the devices on the external body area of the head using a skull cap and spine using a self containing adhesive strip. This will place the devices over neuronal tissue of the brain and spinal cord. When placed in these positions the devices of the invention will bring about neuroprotection alone and will augment therapies such as dilantin and other drugs and/or hyperbaric oxygen treatments utilizing various concentrations of oxygen and various pressures preferably but not limited to 100% oxygen and less that 3 atmospheres of pressure for varying timed intervals and varying number of treatments.

Cerebral ischemia can be either focal or global, implying hypoperfusion of the entire brain. Ischemia is secondary to reduction of cerebral blood flow either locally or globally. Histologically selective neuronal necrosis may occur even after brief periods of global ischemia, and after focal iscemia there may be regions of pan necrosis in the territory of the affected artery. Progressing stroke is an observed deterioration after the initial insult that can occur for at least 48 to 96 hours. This phenomenon is likely related to a combination of evolving thrombosis and progressive cell death. Cell death occurs secondary to hypoxia, spillage of excitalary neurotransmitters, and spillage of calcium secondary to dying cells in the region.

It is a purpose of this invention to demonstrate neuro protection of this device both alone and to augment other agents such as drugs and hyperbaric oxygen both in humans and animal modles.

It is a further purpose of this invention to bring about protection from cell death, reduction of edema and reactivation of live but poorly functioning neuronal tissue in intra-cranial hemorrhage, strokes, hypoxic ischemicencephalopathy, brain contusions, encephalits, radiation therapy and spinal cord injuries.

It is a further purpose of this invention to bring about protection from Vasopastic phenomenon secondary to sub arachnoid hemorrhage. The Vasospams results in delayed cerebral ischemia. The skull cap of the invention generates a magnetic flux field which blocks the vasospastic phenomenon.

Diagnostic Applications

A further object of the invention is to use the combination of selective skin conductance device for locating underlying pathology related to "pacemaker firing" of underlying excitable tissue with a confirmation head which contains a high frequency electrical stimulation and a quadripolar alternating magnetic flux generator which suppresses C-fiber firing and activates A-fiber firing in order to give instant confirmation of the correct location.

N. MagnaScan™ Device for Locating and Confirming the Placement of the Quadripolar Magnetic Device in the Treatment of Pain and Other Dysfunctions.

A diagnostic apparatus with self-contained therapeutic confirmation ability for the location of neuropathology in animals is provided. The device as represented here is designed to be useful for evaluation of local pain such as secondary to local injury and/or inflammation and/or evaluation of radicular pain. The device of the invention allows one to detect changes in selective tissue conductance in the skin as compared to background. It then allows an electrical stimulation of the receptor field. The stimulus is modulated by a quadripolar magnetic flux generator of the invention such that C-fibers are suppressed and A-fibers are stimulated. When the magnetic flux generator of the invention is placed over the area of maximum conductance in a receptor field which corresponds to the local pain pattern, the C-fiber discharge is suppressed. Therefore, pain fiber impulse is blocked at the area of the dorsal root entry zone. Once the area of maximum conductance is located, a second head will be rotated into place (on a turrent) against the skin. This head, which contains a quadripolar, alternating pole, steep gradient magnetic flux generator and electrical stimulating means to stimulate electrically and magnetically. The magnetic gradient suppresses C-fiber firing and the electrical stimulator activates a-delta, thereby blocking pain entry into the central nervous system, thereby providing instant confirmation of the correct location.

An object of this invention to present a method and technique for locating the proper point for application of the magnetic treatment device in a variety of pain syndromes.

A further object of this invention is to reveal a diagnostic device for locating the area of C-fiber and/or A-fiber dysfunction and a method for confirming the location by immediate testing of the efficacy by magnetic and electrical stimulation. This invention as represented is designed to be useful for evaluation of local pain such as secondary to local injury and/or inflammation and/or evaluation of radicular pain.

There is taught the methods, devices, and techniques which relate specifically to the Magnascan™ device for locating and confirming the placement of the quadripolar magnetic device in the treatment of pain and other dysfunctions. Further taught is the method which provides for a diagnostic device for locating the area of C-fiber and/or A-fiber dysfunction and a method for confirming the location by immediate testing of the efficacy by magnetic and electrical stimulation.

There is further taught the method and technique which provides for locating the proper point for application of the magnetic treatment device in a variety of pain syndromes.

There is further taught the method which provides a device which is useful for evaluation of local pain such as secondary to local injury and/or inflammation and/or evaluation of radicular pain.

There is further taught the methods, devices, techniques, and processes which relate specifically to local pain and pain in the pattern of referral of nerves that can be treated locally.

There is further taught the method which provides for a device which when the magnetic flux generator of the invention is placed over the area of maximum conductance in a receptor field which corresponds to the local pain pattern, the C-fiber discharge is suppressed.

There is further taught the method where the pain fiber impulse is blocked distally.

There is further taught the method wherein the device head will contain a quadripolar, alternating pole steep gradient magnetic flux generator and wiring means to stimulate electrically and magnetically.

There is further taught the method wherein the magnetic gradient suppresses C-fiber firing and the electrical stimulator activates A-fiber firing in order to give instant confirmation of the correct location.

There is further taught the methods, devices, techniques, and processes which relate specifically to radicular pain.

There is further taught the method wherein when an area of conductance increases twice background is located, a second head of the device will be rotated into place against the skin.

There is further taught the method wherein the device head will contain a quadripolar, alternating pole, steep gradient magnetic flux generator and wiring means to stimulate electrically and magnetically the magnetic gradient suppresses C-fiber firing and the electrical stimulator activates A-firing in order to give instant confirmation of the correct location.

There is further taught the device wherein the magnetic flux generator will suppress C-fiber firing directly and thereby reduce pain.

There is further taught the device wherein the electrical stimulator will block C-fiber input into the central nervous system in the area of the substantiation.

There is further taught the method wherein the technology also provides for plastic containment means.

1. Local Pain

Local pain is generated in the receptor field of the C-fibers which conduct painful impulses into the dorsal root entry zone and to higher centers where the impulse is interpreted as pain. C-fiber sympathetic efferent fibers are activated at the cord level and these fibers innervate the receptor field where the pain originates. These C-fiber efferents sensitize the somatic afferents. This sympathetic C-fiber efferent discharge into the receptor field brings about an increase of electrolyte and therefore increases the tissue conductance and decreases the resistance. This increased conductance in the skin, if properly interpreted, will allow the practitioners to determine the most effective locations for the quadipolar magnetic flux generator to be placed. When the magnetic flux generator of the invention is placed over the area of maximum conductance in a receptor field which corresponds to the local pain pattern, the C-fiber discharge is suppressed. Therefore, pain fiber impulse is blocked distally. According to the present invention, once the area of maximum conductance is located, a second head will be rotated into place against the skin. This head will contain a quadripolar, alternating pole steep gradient magnetic flux generator and wiring means to stimulate electrically and magnetically. The magnetic gradient suppresses C-fiber firing and the electrical stimulator activates A-fiber firing in order to give instant confirmation of the correct location.

2. Radicular Pain

Radicular pain is generated by abnormal C-fiber discharge within the dorsal root. The symptoms are many such as compression, inflammation, hypoxia, contusion, and neuroproxia.

The dorsal division of the dorsal root is a small remnant in humans and only innervates a narrow strip of tissue on either side of the spinal cord. This dorsal division of the dorsal root contains sympathetic efferent fibers in addition to somatic afferents. These efferent fibers discharge into the receptor field, thereby increasing skin conductance. Therefore, in this instance areas of increased conductance of the skin superficial to the root are compatible with compression, radiculitis or other malfunction of the dorsal root. According to the invention, when an area of conductance increases twice background is located, a second head of the device will be rotated into place against the skin. This head will contain a quadripolar, alternating pole, steep gradient magnetic flux generator and wiring means to stimulate electrically and magnetically the magnetic gradient suppresses C-fiber firing and the electrical stimulator activates A-firing in order to give instant confirmation of the correct location (See FIG. Gate Control Theory). The magnetic flux generator will suppress C-fiber firing directly and thereby reduce pain. The electrical stimulator will block C-fiber input into the central nervous system in the area of the substantiation.

Another object of this invention is to present an electrical stimulator comprised of a pulse generator, controls for controlling the pulse frequency and morphology and an annular electrode system for both conductance reading and a second hear with an annular electrode for stimulation. The technology also provides for plastic containment means.

O. Potentiation of Pharmaceuticals and Focusing the Point of Maximum Therapy by Concentrating Drug to the Active Site.

The present invention relates to magnetic devices for therapeutic application to the human body, and more particularly to various sized magnetic devices for placement on the area of the human body in which drug potentiation is desired, such that the steep field gradient quadripolar field will interact with the drug, receptor or both.

There is taught the methods, devices, techniques, and processes which relate specifically to potentiation of pharmaceuticals and focusing the point of maximum therapy by concentrating drug to the active site.

There is further taught the methods, devices, techniques, and processes which relate specifically to magnetic devices for therapeutic application to the human body particularly to various sized magnetic devices for placement on the area of the human body in which drug potentiation is desired, such that the steep field gradient quadripolar field will interact with the drug and/or receptor.

There is further taught the methods which provides for potentiate the therapeutic effects at the receptor site.

There is further taught the methods which provides for use of magnetically compliant drugs which are thereby concentrated at the receptor area.

There is further taught the methods which potentiate the onset and intensity and duration of local anesthetics such as lidocaine when used as a dermally applied gel underneath the magnetic device for the purpose of bringing about rapid local anesthesia for minor procedures.

There is further taught the methods which place an intracranial quadripolar micro implant near an irritable focus to potentiate the effects of dilantin in the control of seizures which are drug resistant.

The use of pharmaceutical agents in medicine is at an all time high. Along with the desired effects, many drugs have significant side effects (undesirable effects) at the doses needed for the desired therapeutic effects. It is an object of this invention to potentiate the therapeutic effects at the receptor site, and in some instances in which magnetically compliant drugs are involved, the technology of this invention will concentrate the drug at the receptor area.

It is a further object of this invention to potentiate the onset and intensity and duration of local anesthetics such as lidocaine when used as a dermally applied gel underneath the magnetic device for the purpose of bringing about rapid local anesthesia for minor procedures.

It is a further object of this invention to place an intracranial quadripolar micro implant near an irritable focus to potentiate the effects of dilantin in the control of seizures which are drug resistant.

Other Applications

P. Magnetic Placebo.

There is taught the method which provides a magnetic placebo for use in clinical trials. Further taught is a device which provides no biological ability yet is magnetic and has all of the appearance and physical characteristics of the authentic device except there are no alternating poles and it has no significant field gradient.

A therapeutic, static magnetic treatment placebo for placement against the bodies of living animals is provided in which each of three the poles is made of non-magnetizable aluminum. The fourth pole is made of a weak magnetized neodymium magnet with the negative pole facing the body of the animal. In addition, this invention provides a flux blocking plate made of 26 gauge galvanized steel. The plate is square and is located between the poles and the skin.

This application further reveals a method and technique for placement of the devices on the external body in an area of the body in place of an authentic device in a double blinded fashion.

It is a further purpose of this invention to present a magnetic placebo for use in clinical trials. The magnetic placebo has no biological ability yet it is magnetic and has all of appearance and physical characteristics of the authentic device except the alternating poles and it has no significant field gradient.

Another object of this invention is to present a magnetic treatment placebo which is designed to have minimal field gradient and all positive poles facing the animal body. This object is accomplished by forming a quadripolar array as in the authentic device. Three of the poles are non-magnetizable aluminum and the fourth pole is a magnetic pole which is about one half the strength of therapeutic poles of the authentic therapeutically active device. A square flux blocking plate made of galvanized steel is placed between the poles and the animal skin such that a weaker, diffuse magnetic flux field of all negative magnetic flux facing the animal skin.

Q. Control of Nausea and Vomiting Associated with Pregnancy Motion and Chemotherapy.

This application reveals a method and technique for placement of the invention on the external body area over the vestibules apparatus and the distal medial radius area for the control of nausea and vomiting associated with pregnancy, motion and chemotherapy.

There is further taught the methods, devices, techniques, and processes which specifically relates to nausea and vomiting associated with pregnancy, motion and chemotherapy and also secondary to a variety of external stimuli.

The present invention relates to magnetic devices for therapeutic application to the human body and more particularly to a static magnetic quadripolar treatment device for placement on the human body for control of nausea and/or vomiting associated with pregnancy, motion sickness and chemotherapy.

Nausea and vomiting associated with a variety of stimuli is controlled by the emetic center in the central nervous system. This technology of the present invention controls the nausea and vomiting secondary to a variety of underlying etiologies by modulating peripheral input into the CNS. This is accomplished by placing the device just proximal and lateral to the wrist on the palmar surface of both arms and/or placement over the vestibular apparatus (posterior to the external ear).

R. Prevention of Fertilization of the Ovum by the Sperm.

This application further reveals a method and technique for placement of the invention as part of a safe and effective intra-uterine device to prevent fertilization of the ovum by the sperm. The device will contain 6 quadripolar devices in a containment means to hold the device in a stable condition such that the entire uterus will respond to the flux and thereby prevent penetration of the ovum by the sperm.

It is a further object of the invention to provide a device that blocks the fertilization of the ovum by human or animal sperm.

Another object of the invention is to provide an apparatus for applying a symmetric quadripolar, three dimensional magnetic flux field which is focused and balanced to the human body to block penetration of the ovum by the sperm.

It is a further object of the invention to demonstrate that the primary mechanism is through calcium channel blockade.

A further object of the invention to provide a method for applying a therapeutic magnetic device to the human body to control fertilization of the human ovum by a sperm.

What is claimed is:

1. An apparatus for altering the charge distribution upon living membranes with functional stabilizational of the membrane's physical electrical integrity comprising a submicroscopic, quadripolar, circular, center charged, energy balanced magnetic implantable device including flux focusing and flux return ring in a four (4) magnet array of alternating polarity in which the magnetic poles are separated only by a distance which will allow a magnetic sphere of influence on all adjacent poles to suppress the firing of action potentials of mammalian sensory neurons.

2. The apparatus in claim 1, wherein the apparatus provides a static magnetic device for production of a magnetic field for treatment of various disorders.

3. The apparatus of claim 1, further providing a static magnetic device for production of a magnetic field for treatment of disorders wherein the device provides a static magnetic pole of like polarity on the outer surface of a flux focusing ring adjacent to each of the 4 poles of a focusing magnet such that the end on top of the focusing magnet is oriented to a geometric side of the pole such that an axis of two magnets to form a 45 to 90 degree angle.

4. The apparatus in claim 1, wherein the apparatus comprises a means to treat and transport human organs for donation.

5. The apparatus in claim 1, wherein the apparatus comprises a means to counteract the negative effects of pain and swelling while promoting wound healing.

6. The apparatus of claim 1, further defining a means for applying a symmetric quadripolar, three dimensional magnetic flux field which is focused and balanced to the human body to stabilize excitable membranes and thereby reduce pain and edema associated with acute injury, inflammation or surgical procedure and to decrease wound healing time.

7. The apparatus in claim 1, further providing an alternating, quadripolar array in which each of the poles is in the shape of two cones joined at the directrix of the cone with the vertex of the two cones lying in a perpendicular axis of a circular directrix.

8. The apparatus in claim 1, wherein the apparatus further provides a flux focusing ring surrounding 4 static magnetic poles on the outer perimeter stationed essentially midway between the top and bottom of the pole.

9. The apparatus in claim 1, further providing means for counteracting the negative effects of chronic pain while promoting wound healing.

10. A method for altering the charge distribution upon living membranes with functional stabiization of the membrane's physical electrical integrity which comprises the steps of applying a symmetric, and balanced magnetic field provided by a quadripolar center charge energy balance of magnetic device in a four (4) magnet array of alternating polarity containing flux focusing and a flux return ring, the device applied to the living membranes to stabilize excitable membranes and thereby reduce pain associated with the spontaneous pacemaker firing of chronically malfunctioning polymodal nociceptors (afferent C-fibers and A delta fibers).

* * * * *